United States Patent
Dollings et al.

[11] Patent Number: 6,121,271
[45] Date of Patent: *Sep. 19, 2000

[54] NAPHTHO[2,3-B]HETEROAR-4-YL DERIVATIVES

[75] Inventors: Paul J. Dollings, Newtown, Pa.; Arlene J. Dietrich, Delran; Jay E. Wrobel, Lawrenceville, both of N.J.

[73] Assignee: American Home Products Corporation, Madison, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/307,688

[22] Filed: May 10, 1999

Related U.S. Application Data

[60] Provisional application No. 60/108,157, May 12, 1998, abandoned.

[51] Int. Cl.$^7$ ............... A61K 31/505; C07D 409/00; C07D 405/00; C07D 401/00
[52] U.S. Cl. ............... 514/269; 514/269; 514/411; 514/443; 544/333; 549/458; 549/43; 548/427; 546/276.7; 546/284.1; 546/281.1
[58] Field of Search ............... 544/333; 546/276.7, 546/281.1, 284.1; 514/339, 337, 461, 411, 443, 369; 549/458, 43; 548/427

[56] References Cited

FOREIGN PATENT DOCUMENTS

| | | |
|---|---|---|
| 0568289 | 11/1993 | European Pat. Off. |
| 0693491 | 1/1996 | European Pat. Off. |
| 0416854 | 1/1992 | Japan. |
| 9429290 | 12/1994 | WIPO. |
| 9639401 | 12/1996 | WIPO. |
| 9708126 | 3/1997 | WIPO. |

OTHER PUBLICATIONS

Chen, H.–M. et al., Indian J. Chem., 35B, 1996, pp. 1304–1307.
Dryhurst, G. et al., J. Am. Chem. Soc., 111, 1989, pp. 719–726.
d'Ischia, M. et al., Tetrahedron, 43:2, 1987, pp. 431–434.
Molina, P. et al., Tetrahedron, 50:17, 1994, pp. 5027–5036.
Napolitano, A. et al., Tetrahedron, 45:21, 1989, pp. 6749–6760.
Konopelski, J. P., et al., Synlett, 1996, pp. 609–611.
Kuroda, T. et al., J. Org. Chem., 59, 1994, pp. 7353–7357.
Molina, P., Tetrahedron Letters, 34:17, 1993, pp. 2809–2812.
Guirguis, N. R. et al., Liebigs Ann. Chem., 1986, pp. 1003–1011.
Guirguis, N. R. et al., J. Prakt. Chemie., Band 332, Heft 3, 1990, pp. 414–418.
Hashem, A. I., J. Prakt. Chemie., Band 319, Heft 4, 1977, pp. 689–692.

Primary Examiner—Zinna Northington Davis
Assistant Examiner—Binta Robinson
Attorney, Agent, or Firm—Arnold S. Milowsky

[57] ABSTRACT

This invention provides compounds of Formula I having the structure

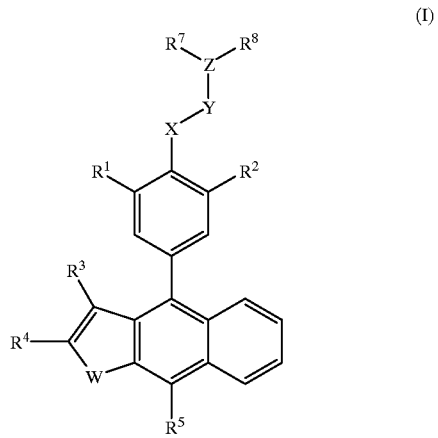

(I)

wherein
$R^1$, $R^2$, $R^3$, $R^4$, $R^5$, W, $R^9$, X, $R^6$, p, Y, Z, $R^7$, and $R_8$ are as defined in the specification, or a pharmaceutically acceptable salt thereof, which are useful in treating metabolic disorders related to insulin resistance or hyperglycemia.

37 Claims, No Drawings

NAPHTHO[2,3-B]HETEROAR-4-YL DERIVATIVES

This application claims the benefit of U.S. Provisional Application No. 60/108,157, which was converted from U.S. patent application Ser. No. 09/076,446, filed May 12, 1998, pursuant to a petition filed under 37 C.F.R. 1.53(c)(2)(i) on Aug. 17, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinernia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

B. Reidl, et al. (EP 693491A1) disclosed the oxazolodinone A as an antibacterial agent.

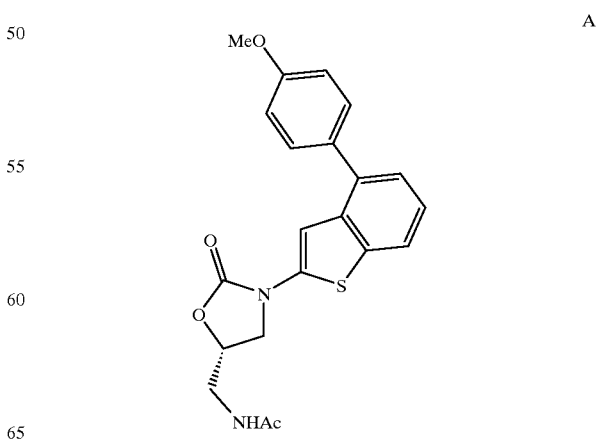

A

A. Bridges, et al. (EP 568289A2) disclosed the thienothiopheneamidine B as a urokinase inhibitor.

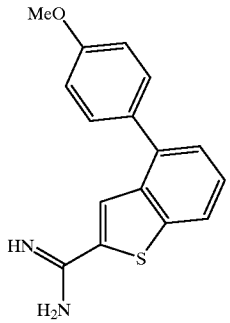

B

H.-M. Chen, et al., *Indian J. Chem.,Sect.* B: *Org. Chem. Include. Med. Chem.* 1996, 35B(12), 1304–1307 disclosed compound C.

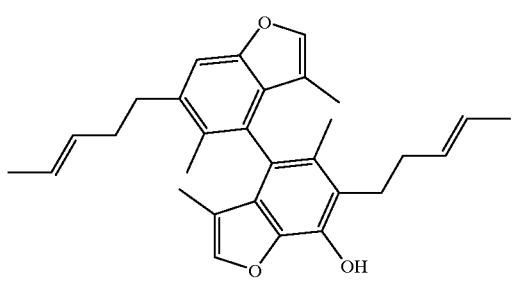

C

N. R. Guirguis, et al., *J. Prakt Chem.* 1990, 332(3), 414–418 disclosed compound D.

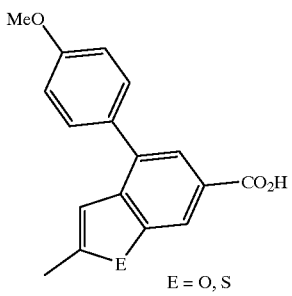

D

N. R. Guirguis, et al., *Liebigs Ann. Chem.* 1986, 1003–1011 disclosed benzothiophenes E. Also M. C. Dubroeucq et al., (EP 248734A1) disclosed E (R1=CO$_2$H) as an anxiolytic.

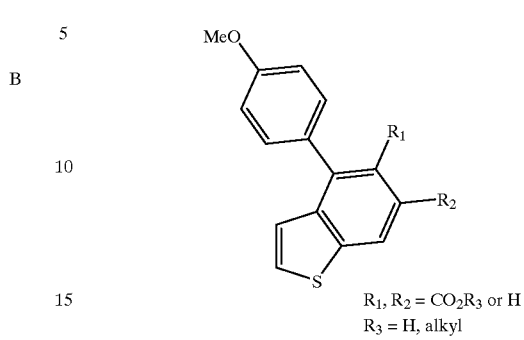

E $R_1, R_2 = CO_2R_3$ or H
$R_3 = H$, alkyl

T. Kuroda, et al., *J. Org. Chem.* 1994, 59, 7353–7357 and *J. Chem. Soc., Chem. Commun.* 1991, 1635–1636 disclosed benzothiophenes F.

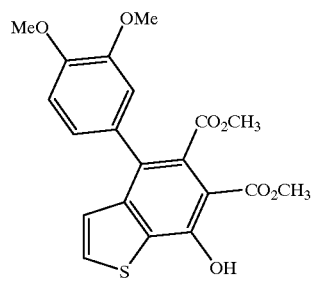

F

A.I. Hashem, *J. Prakt. Chem.* 1977, 319, 689–692 disclosed benzofuran G.

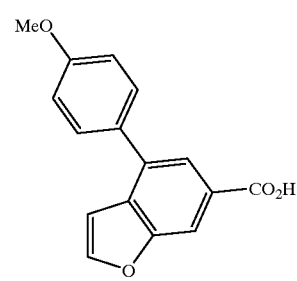

G

Y. Akao, et al., Jpn. Kokai Tokkyo Koho JP 04016854 A2(Japanese patent, CA: 117:36570) disclosed six compounds containing the 4-aryl-naphtho[2,3-b]thiophene ring system. These compounds were cyclobutenediylium dimers of that ring system made as electrophotographic photoreceptors. One typical example is shown by structure H below.

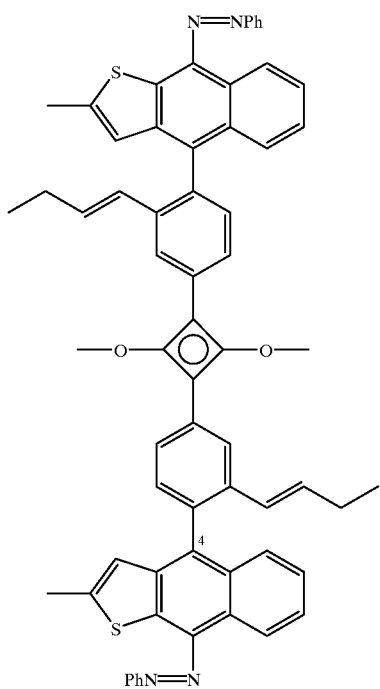

J. P. Konopelski, et al., *Synlett* 1996, 609–611 disclosed indole I.

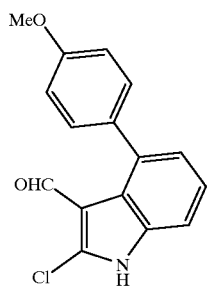

P. Molina, et al, *Tetrahedron*, 1994, 50, 5027–36 and *Tetrahedron Lett.*, 1993, 34, 2809–2812 disclosed indole derivatives J.

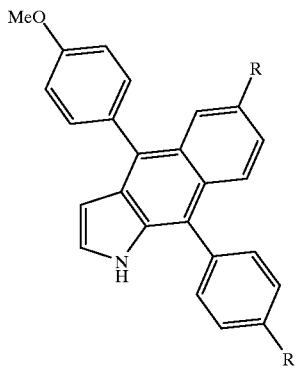

R = H or Me

A. Napolitano, et al., *Tetrahedron* 1989, 45, 6749–60 disclosed indole K.

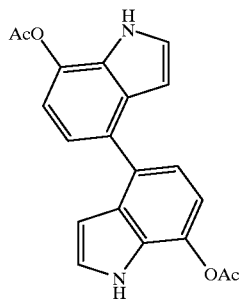

G. Dryhurst, et al., *J. Am. Chem. Soc.* 1989, 111, 719–726 disclosed compound L.

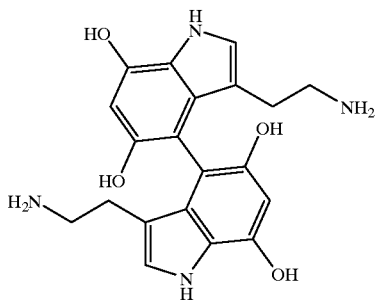

M. d'Ischia, et al., *Tetrahedron* 1987, 43, 431–434 disclosed compound M.

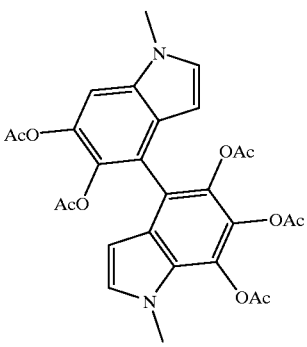

None of the above disclosures (A–M) contained the appropriate substitution necessary for in vitro PTPase inhibition activity or in vivo antidiabetic activity.

DESCRIPTION OF THE INVENTION

This invention provides compounds of Formula I having the structure

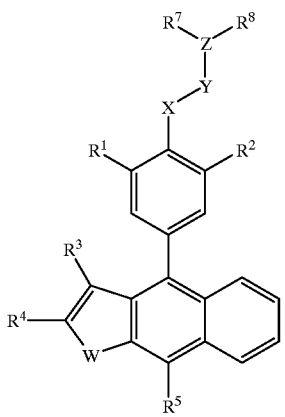

(I)

wherein

R$^1$ and R$^2$ are each, independently, hydrogen, nitrile, nitro, amino, alkylamino of 1–6 carbon atoms, dialkylamino of 1–6 carbon atoms per alkyl group, cycloalkylamino of 3–8 carbon atoms, alkyl of 1–6 carbon atoms, perfouroalkyl of 1–6 carbon atoms, halogen, cycloalkyl of 3–8 carbon atoms, thienyl, furyl, phenyl or phenyl mono-, di-, or tri- substituted with halogen, hydroxy, alkyl of 1–6 carbon atoms, perfluoroalkyl of 1–6 carbon atoms, alkoxy of 1–6 carbon atoms, or perfluoroalkoxy of 1–6 carbon atoms;

R$^3$ and R$^4$ are each, independently, hydrogen, alkyl of 1–6 carbon atoms, perfluoroalkyl of 1–6 carbon atoms, hydroxyalkyl of 1–6 carbon atoms, aminoalkyl of 1–6 carbon atoms, acyl of 2–7 carbon atoms;

R$^5$ is hydrogen, halogen, alkyl of 1–6 carbon atoms, perfluoroalkyl of 1–6 carbon atoms, nitrile, alkoxy of 1–6 carbon atoms, aryloxy, arylalkoxy of 6–12 carbon atoms, arylsulfanyl;

W is S, O, or NR$^9$;

R$^9$ is hydrogen or alkyl of 1–6 carbon atoms, X is O, —NR$^6$—, or —(CH$_2$)$_p$NR$^6$—;

R$^6$ is hydrogen, or alkyl of 1–6 carbon atoms;

p is 1 to 4;

Y is methylene, carbonyl, —SO$_2$—, or —SO—;

Z is phenyl, heteroaryl, or naphthyl;

R$^7$ and R$^8$ are each, independently, hydrogen, carboxyl, acyl of 2–7 carbon atoms, hydroxyl, hydroxyalkyl of 1–6 carbon atoms, hydroxyalkanoyl of 1–6 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aryl of 6–12 carbon atoms, aryloxycarbonyl of 7–13 carbon atoms, heteroaryloxycarbonyl, heteroaryl, tetrazolyl, mercapto, alkylsulfanyl of 1–6 carbon atoms, nitrile, amino, carbamoyl, aminoalkyl of 1–6 carbon atoms, alkylamino of 1–6 carbon atoms, dialkylamino of 1–6 carbon atoms per alkyl group, —NHSO$_2$CF$_3$, carboxyaldehyde, halogen, nitro, acylamino of 1–6 carbon atoms, 3-hydroxy-cyclobut-3-ene-4-yl-1,2-dione, or tetronic acid, —OCOR$^{10}$, —OR$^{10}$ R$^{10}$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms; or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The terms alkyl, alkoxy, alkanoyl used alone or in conjunction with another term are defined as branched or straight chained optionally substituted with fluorine. The term cycloalkyl may be optionally substituted with flourine. Halogen means bromine, chlorine, fluorine, and iodine.

It is preferred that the aromatic portion of the terms aryl, aralkyl, arylalkoxy, aryloxy, aroyloxy, or aryloxycarbonyl substituent is a phenyl, naphthyl or 1,4-benzodioxan-5-yl group, with phenyl being most preferred. The aryl moiety may be optionally mono-, di-, tri- substituted with a substituent selected from the group consisting of alkyl of 1–6 carbon atoms, alkylsulfanyl of 1–6 carbon atoms, alkoxy of 1–6 carbon atoms, trifluoromethyl, halogen, mercapto, alkoxycarbonyl of 2–7 carbon atoms, alkylamino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The heteroaromatic portion of the terms heteroaryl, heteroaralkyl and heteroaryloxycarbonyl are defined as a stable 5 to 10 member mono or bicyclic heterocyclic ring system which consists of carbon atoms and from 1 to 3 heteroatoms selected from N, O and S and selected from the group consisting of quinoline, isoquinoline, pyridine, indole, isoindole, pyrrole, quinazoline, oxazole, oxazine, isoxazole, isothiazole, pyrazine, pyridazine, pyrrolidinone, benzoxazole, benzpyrazzole, benzimidazole, benzoxadiazole, pyrazole, pyrrolidinone, benzoxazole, benzpyrazzole, benzisoxazole, thiazole, thiadiazole, triazole, isobenzothiophene and benzothiophene. The heteroaromatic group may be optionally mono-, di-, or tri- substituted with a substituent selected from the group consisting of alkyl of 1–6 carbon atoms, alkylsulfanyl of 1–6 carbon atoms, alkoxy of 1–6 carbon atoms, trifluoromethyl, halogen, mercapto, alkoxycarbonyl of 2–7 carbon atoms, alkylamino of 1–6 carbon atoms, dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and disastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The compounds of this invention may be atropisomers by virtue of possible restricted or slow rotation about the aryl-tricyclicycle single bond. This restricted additional chiral center in the molecule, diasteriomers exist and can be seen in the NMR and via other analytical techniques. While shown without respect to atropisomer stereochemistry in Formula I, the present invention includes such atoropisomers (enantiomers and diastereomers; as well as the racemic, resolved, pure diastereomers and mixtures of diastereomers) and pharmaceutically acceptable salts thereof.

Preferred compounds of this invention are those compounds of Formula I in which:

$R^1$ and $R^2$ are each, independently, hydrogen, alkyl of 1–6 carbon atoms, perfluoroalkyl of 1–6 carbon atoms, bromo, iodo, cycloalkyl of 3–8 carbon atoms, phenyl or phenyl substituted with trifluoromethyl, chloro, methoxy, —$OCF_3$, thienyl, or furyl;

$R^3$ and $R^4$ are each, independently, alkyl of 1–6 carbon atoms, or perfluoroalkyl of 1–6 carbon atoms;

$R^5$ is hydrogen, halogen, alkyl of 1–6 carbon atoms, perfluoroalkyl of 1–6 carbon atoms, nitrile, alkoxy of 1–6 carbon atoms, aryloxy, arylalkoxy, or arylsulfanyl;

W is S, or O;

X is O, —$NR^6$—, or —$(CH_2)_pNR^6$—;

$R^6$ is hydrogen or, alkyl of 1–6 carbon atoms;

$R^6$ is hydrogen or, alkyl of 1–6 carbon atoms;

p is 1 to 4;

Y is methylene, carbonyl, —$SO_2$—, or —SO—;

Z is phenyl,pyridyl, naphtyl, thienyl, furyl, pyrroryl, pyrazolyl, isoxazolyl, or isothiazolyl;

$R^7$ and $R^8$ are, each independently, hydrogen, halogen, carboxyl, acyl of 1–6 carbon atoms, acylamino of 1–6 carbon atoms, hydroxyl, hydroxyalkyl of 1–6 carbon atoms, hydroxyalkanoyl of 1–6 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aryl of 6–12 carbon atoms, aryloxy of 7–13 carbon atoms, aryloxycarbonyl of 7–13 carbon atoms, heteroaryloxycarbonyl, pyridyl, tetrazolyl, pyrazolyl, oxazolyl, isoxazolyl, mercapto, alkylsulfanyl of 1–6 carbon atoms, nitrile, amino, —$NHSO_2CF_3$, carbamoyl, aminoalkyl of 1–6 carbon atoms, alkylamino of 1–6 carbon atoms, dialkylamino in which each of the alkyl groups is of 1–6 carbon atoms, carboxyaldehyde, halogen, nitro, or pyrimidyl or pyrimidyl substituted with alkylsulfanyl of 1–6 carbon atoms, 3-hydroxy-cyclobut-3-ene-4-yl-1,2-dione, —$OR^{10}$, —$OCOR^{10}$ or a pharmaceutically acceptable salt thereof.

More preferred compounds of this invention are those compounds of Formula I in which:

$R^1$ and $R^2$ are, each independently, hydrogen, alkyl of 1–6 carbon atoms, bromo, or cyclopentyl;

$R^3$ and $R^4$ are alkyl of 1–6 carbon atoms;

$R^5$ is hydrogen or bromine;

W is S, or O;

X is O, —$NR^6$—, or —$CH_2NR^6$—;

$R^6$ is hydrogen or alkyl of 1–6 carbon atoms;

Y is methylene, carbonyl, or —$SO_2$—;

Z is phenyl, thienyl, pyrazolyl, or thiazolyl;

$R^7$ and $R^8$ are each, independently, hydrogen, halogen, acyl of 1–6 carbon atoms, carboxyl, hydroxyl, alkoxycarbonyl of 2–7 carbon atoms, alkyl of 1–6 carbon atoms, pyridyl, isoxazolyl, nitrile, or pyrimidyl or pyrimidyl substituted with alkylsulfamyl of 1–6 carbon atoms, —$OCOR^{10}$, or $OR^{10}$;

$R^{10}$ is aryl of 6–12 carbon atoms, monocyclic heteroaryl, or alkyl of 1–6 carbon atoms; or a pharmaceutically acceptable salt thereof.

Even more preferred compounds of this invention are:

Example 1  4-[4-(9-Bromo-2,3-dimethyl-naphtho[2,3-b]thiophen-4-yl)-2-isopropyl-phenoxysulfonyl]-2-hydroxy-benzoic acid;

Example 2  4-[4-(9-Bromo-2,3-dimethyl-naphtho[2,3-b]thiophen-4-yl)-2,6-dimethyl-phenoxysulfonyl]-2-hydroxy-benzoic acid;

Example 3  4-[4-(9-Bromo-2,3-dimethyl-naphtho[2,3-b]thiophen-4-yl)-2-cyclopentyl-phenoxysulfonyl]-2-hydroxy-benzoic acid;

Example 4  4-[4-(9-Bromo-2,3-dimethyl-naphtho[2,3-b]thiophen-4-yl)-2,6-diisopropyl-phenoxysulfonyl]-2-hydroxy-benzoic acid;

Example 5  2-Acetoxy-4-[4-(9-bromo-2,3-dimethyl-naphtho[2,3-b]thiophen-4-yl)-2,6-dimethyl-phenoxysulfonyl]-benzoic acid;

Example 6  2-Acetoxy-4-[4-(9-bromo-2,3-dimethyl-naphtho[2,3-b]thiophen-4-yl)-2-cyclopentyl-phenoxysulfonyl]-benzoic acid;

Example 7  2-Butyryloxy-4-[4-(9-bromo-2,3-dimethyl-naphtho[2,3-b]thiophen-4-yl)-2,6-dimethyl-phenoxysulfonyl]-benzoic acid;

Example 8  2-Benzoyloxy-4-[4-(9-bromo-2,3-dimethyl-naphtho[2,3-b]thiophen-4-yl)-2,6-dimethyl-phenoxysulfonyl]-benzoic acid;

Example 9  2-Propionyloxy-4-[4-(9-bromo-2,3-dimethyl-naphtho[2,3-b]thiophen-4-yl)-2,6-dimethyl-phenoxysulfonyl]-benzoic acid;

Example 10  5-[4-(9-Bromo-2,3-dimethyl-naphtho[2,3-b]thiophen-4-yl)-2-cyclopentyl-phenoxysulfonyl]-4-methoxy-thiophene-3-carboxylic acid;

Example 11  5-[4-(9-Bromo-2,3-dimethyl-naphtho[2,3-b]thiophen-4-yl)-2-cyclopentyl-phenoxysulfonyl]-4-hydroxy-thiophene-3-carboxylic acid;

Example 12  4-[2-Cyclopentyl-4-(2,3-dimethyl-naphtho[2,3-b]thiophen-4-yl)-phenoxysulfonyl]-2-hydroxy-benzoic acid;

Example 13  4-[2-Cyclopentyl-4-(2,3-dimethyl-naphtho[2,3-b]furan-4-yl)-phenoxysulfonyl]-2-hydroxy-benzoic acid;

Example 14  4-[2-Bromo-4-(2,3-dimethyl-naphtho[2,3-b]furan-4-yl)-6-ethyl-phenoxysulfonyl]-2-hydroxy-benzoic acid;

Example 15  4-[4-(2,3-Dimethyl-naphtho[2,3-b]furan-4-yl)-2,6-diethyl-phenoxysulfonyl]-2-hydroxy-benzoic acid;

Example 16  4-[4-(9-Bromo-2,3-dimethyl-naphtho [2,3-b]thiophen-4-yl)-2,6-dimethyl-phenoxysulfonyl]-2-hydroxy-benzoic acid tert-butyl ester;

Example 17  2-(4-Methoxy-benzoyl)oxy-4-[4-(9-bromo-2,3-dimethyl-naphtho[2,3-b]thiophen-4-yl)-2,6-dimethyl-phenoxysulfonyl]-benzoic acid;

Example 18  5-[4-(2,3-dimethyl-naphtho[2,3-b]thiophen-4-yl)-2,6-diethyl-phenoxysulfonyl]-4-methoxy-thiophene-3-carboxylic acid;

Example 19  5-Pyridin-2-yl-thiophene-2-sulfonic acid 2-cyclopentyl-4-(2,3-dimethyl-naphtho[2,3-b]thiophen-4-yl)-phenyl ester;

Example 20  4-Benzoyloxy-5-[4-(2,3-dimethyl-naphtho[2,3-b]thiophen-4-yl)-2,6-diethyl-phenoxysulfonyl]-thiophene-3-carboxylic acid;

Example 21  3-[2-Cyclopentyl-4-(2,3-dimethyl-naphtho[2,3-b]thiophen-4-yl)-phenoxysulfonyl]-benzoic acid;

Example 22  5-(2-Methylsulfanyl-pyrimidin-4-yl)-thiophene-2-sulfonic acid 2-cyclopentyl-4-(2,3-dimethyl-naphtho[2,3-b]thiophen-4-yl)-phenyl ester;

Example 23  2-Benzoyloxy-4-[4-(2,3-dimethyl-naphtho[2,3-b]thiophen-4-yl)-2,6-dimethyl-phenoxysulfonyl]-benzoic acid;

Example 24 2-(4-Chloro-benzoyl)oxy-4-[4-(2,3-dimethyl-naphtho[2,3-b]thiophen-4-yl)-2,6-dimethyl-phenoxysulfonyl]-benzoic acid;

Example 25 Nicotinic acid 2-carboxy-5-[4-(2,3-dimethyl-naphtho[2,3-b]thiophen-4-yl)-2,6-dimethyl-phenoxysulfonyl]-phenyl ester;

Example 26 Nicotinic acid 2-carboxy-5-[4-(9-bromo-2,3-dimethyl-naphtho[2,3-b]thiophen-4-yl)-2,6-dimethyl-phenoxysulfonyl]-phenyl ester;

Example 27 4-[4-(9-Bromo-2,3-dimethyl-naphtho[2,3-b]thiophen-4-yl)-2,6-dimethyl-phenoxysulfonyl]-2-phenylacetoxy-benzoic acid;

Example 28 2-(4-Cyano-benzoyl)oxy-4-[4-(9-bromo-2,3-dimethyl-naphtho[2,3-b]thiophen-4-yl)-2,6-dimethyl-phenoxysulfonyl]-benzoic acid;

Example 29 2-(3-Methoxy-benzoyl)oxy-4-[4-(9-bromo-2,3-dimethyl-naphtho[2,3-b]thiophen-4-yl)-2,6-dimethyl-phenoxysulfonyl]-benzoic acid;

Example 30 Isonicotinic acid 5-[4-(9-bromo-2,3-dimethyl-naphtho[2,3-b]thiophen-4-yl)-2,6-dimethyl-phenoxysulfonyl]-2-carboxy-phenyl ester;

and the pharmaceutically acceptable salts thereof.

The compounds of this invention can be prepared according to the following schemes from commercially available starting materials or starting materials which can be prepared using to literature procedures. These schemes show the preparation of representative compounds of this invention.

Scheme 1

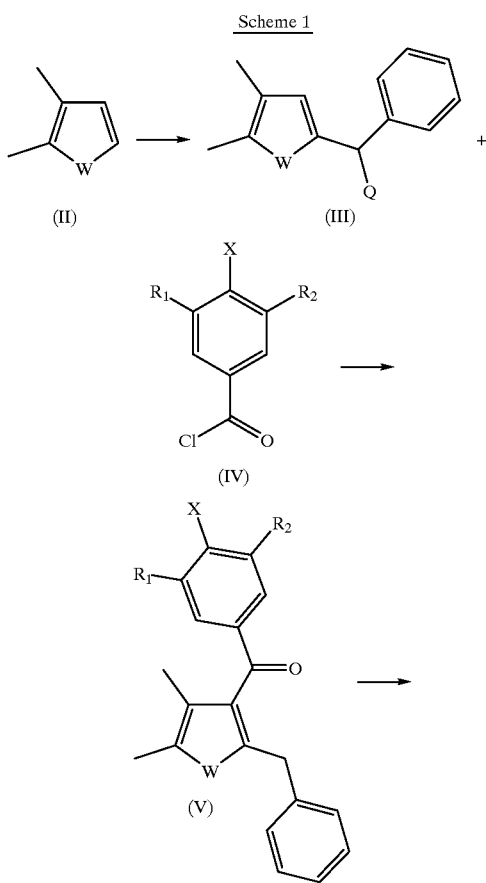

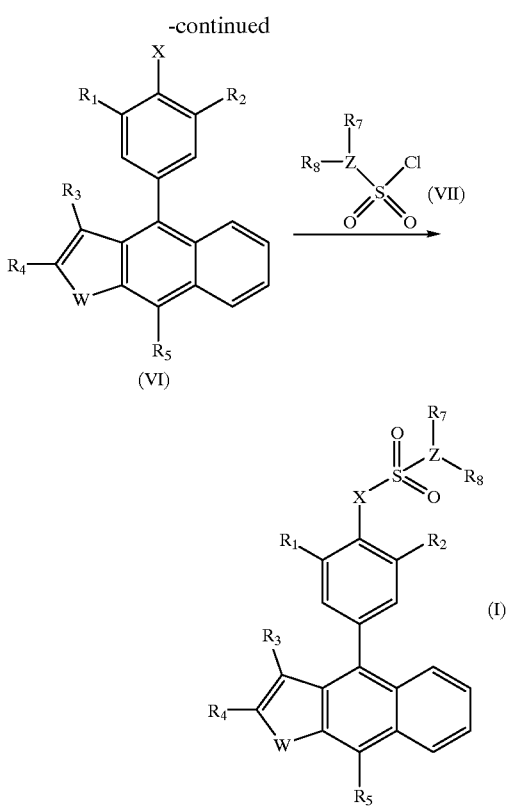

In Scheme 1, 2, 3-dimethyithiophene (II: W is S) is prepared from commercially available 3-methyl-thiophene-carboxaldehyde using Wolff-Kishner conditions (hydrazine followed by KOH/ethylene glycol reflux). Compound (II) is treated with one to 1.3 molar equivalents of an alkyl lithium reagent such as N-butyl lithium most preferably in a nonprotic solvent such as THF at temperatures ranging from −78° C. to room temperature under an inert atmosphere such as nitrogen or argon to provide the 2-lithiated-thiophene or furan derivative. This lithiated analog is reacted in situ with one or more molar equivalents of benzaldehyde, generally at −78° C. to room temperature for 5 min to 3 h to provide the compound of formula (III: Q=OH). The hydroxy group (Q=OH) of (III) can be removed by a number of reduction procedures such as hydrogenation using palladium catalysts to produce the compound of formula (III: Q=H) but is most conveniently removed using the method of Nutaitis, et. al. (*Org. Prep. and Proceed. Int*. 1991, 23, 403–411) in which (III: Q=OH; W is S or O) is stirred with one to ten molar equivalents of sodium borohydride in a suitable solvent such as ether, THF or dichloromethane at 0° C. to room temperature and one to fifty molar equivalents of trifluoroacetic acid is slowly added over a 15 min to 3 h period to produce the compound of formula (III: Q=H). Alternatively, the 2-lithiated analog of compound (II) in a nonprotic solvent such as THF can be reacted with onr or more molar equivalents of a benzyl halide such as benzyl bromide (PhCH₂Br) at −78° C. to room temperature to directly provide the compound of formula (III: Q=H; W is S or O).

The compounds of formula (III: Q=H) can be acylated with one or more molar equivalents of a commercially available benzoic acid chloride of formula (IV: X=—OMe) to produce the acylated derivative of formula (V: X=—OMe). This acylation is accomplished most readily using a one to five molar equivalents of a Lewis acid catalyst such as tin tetrachloride or aluminum chloride in an inert solvent such as dichloromethane, 1,2-dichloroethane or carbon disulfide, generally at temperatures such as −78° C. to room temperature. The benzoic acid chloride (IV: X=—OMe). is prepared from the corresponding benzoic acid by standard procedures using reagents such as oxalyl chloride and thionyl chloride. The starting benzoic acid of the benzoic acid chloride (IV: X=—OMe) is commercially available or can be easily prepared by known procedures. For example, the acid starting material for benzoic acid chloride (IV) can be prepared using a modification of the method of Schuster, et al., *J. Org. Chem.* 1988, 53, 5819. Thus commercially available 2,6-diisopropyl phenol is brominated in the 4-position (bromine/acetic acid), methylated (iodomethane/potassium carbonate/DMF), reacted with n-butyl lithium to effect lithium halogen exchange and the resultant organolithium species is reacted with carbon dioxide to provide 3,5-diisopropyl, 4-methoxy benzoic acid. Alternatively, the commercially available 2,6-(mono or disubstituted)phenols can be methylated (iodomethane/potassium carbonate/DMF), acylated in the 4-position with 2-chlorobenzoyl chloride in the presence of aluminum chloride in an inert solvent such as dichloromethane, generally at ambient temperature and reacted with potassium-t-butoxide in $H_2O$/ethylene glycol dimethyl ether at ambient temperature to give the desired 2,6-(mono or disubstituted) benzoic acid.

Cyclization of the compounds of formula (V: X=—OMe) is generally best accomplished using onto to ten molar equivalents of a strong Lewis acid such as a trihaloborane, most conveniently tribromoborane. The reaction is best performed at −78° C. with warming to room temperature or heating to 50° C. in a halocarbon solvent such as dichloromethane under an inert atmosphere such as nitrogen or argon. These procedures not only effect cyclization and aromatization with concomitant loss of water, but also result in demethylation of any pendant methoxy moieties and result in the production of compounds of formula (VI: X=—OH).

The compounds of formula (VI: X=—OH) can be sulfonylated on the phenolic oxygen using one or more molar equivaltents of suitable sulfonylating agent to provide the sulfonic acid esters of formula (I). The sulfonylating agent is generally a aryl or heteroaryl sulfonic acid chloride. The reaction is run under standard conditions using a suitable base such sodium hydride, pyridine or Tris base in an appropriate solvent such as dichloromethane, THF or $H_2O$ at temperatures from 0° C. to ambient temperature. The starting sulfonyl chloride is commercially available or can be easily prepared by known procedures. For example, the aryl or heteroaryl sulfonic acid chloride can be prepared by reacting the aryl or heteroaryl sulfonic acid with one or more molar equivalents of oxalyl chloride or thionyl chloride, in a suitable solvent such as dichloromethane, chloroform or diethyl ether, to afford the aryl or heteroaryl sulfonic acid chloride. This reaction is often catalyzed by adding small amounts (0.01 to 0.1 molar equivalents) of dimethylformamide. Alternatively, the sulfonyl chlorides can prepared using a modification of Barraclough, et al., *Arch. Pharm.* (Weinheim) 1990, 323, 507. Thus, the aniline of commercially available 4-aminosalicylic acid sodium salt dihydrate is diazotized with sodium nitrite in HOAc/HCl at −10° C. and the subsequent diazonium salt can be converted to the sulfonyl chloride by introduction of sulfur dioxide into the reaction in the presence of copper (I) chloride.

The groups $R^7$ and $R^8$ connected to Z can be further derivatized. For example, when $R^7$ or $R^8$ is an ester of a carboxylic acid or alcohol the compound can be transformed into the respective carboxylic acid or alcohol such as sodium hydroxide is one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Acidic conditions to effect the ester to acid conversion include using trifluoroacetic acid in a suitable solvent such as dichloromethane. When $R^7$ or $R^8$ is a carboxcylic acid or ester the compound can be reduced to the respective primary alcohol analog using standard conditions such as lithium aluminum hydride in ethyl ether. When $R^7$ or $R^8$ is an aldehyde or ketone the compound can be reduced to the respective primary alcohol analog using a metal catalyst, by sodium in alcohol, sodium borohydride and by lithium aluminum hydride. When $R^7$ or $R^8$ is an ether, the compound can be transformed to the free alcohol by using one to ten molar equivalents of a strong Lewis acid such as a trihaloborane, most conveniently tribromoborane in a halocarbon solvent such as dichloromethane. When $R^7$ or $R^8$ is an alcohol the compound can be oxidized to the respective aldehyde, carboxylic acid or ketone analog using a transition metal oxidant (chromium trioxide-pyridine, pyridinium chlorochromate, manganese dioxide) in an inert solvent such as ether, dichloromethane. Alcohols can also be oxidized using DMSO with a number of electrophilic molecules (dicyclohexylcarbodiimide, acetic anhydride, trifluoro acetic anhydride, oxalyl chloride and sulfur dioxide). When $R^7$ or $R^8$ is a carboxcylic acid the compound can be transformed into a carboxylic acid amide analog. This transformation can be accomplished using standard methods to effect carboxylic acid to carboxylic acid amide transformations. These methods include converting the acid to an activated acid and reacting with one or more molar equivalents of the desired amine. Amines in this category include ammonia in the form of ammonium hydroxide, hydroxyl arnine and 2-aminopropionitrile. Methods to activate the carboxylic acid include reacting said acid with one or more molar equivalents of oxalyl chloride or thionyl chloride to afford the carboxylic acid chloride in a suitable solvent such as dichloromethane, chloroform or diethyl ether. This reaction is often catalyzed by adding small amounts (0.01 to 0.1 molar equivalents) of dimethylformamide. Other methods to activate the carboxylic acid include reacting said acid with one or more molar equivalents dicyclohexylcarbodiimide with or without one or more molar equivalents of hydroxybenzotriazole in a suitable solvent such as dichloromethane or dimethylformamide at temperatures ranging from 0° C. to 60° C. When $R^3$ or $R^4$ is a carboxcylic acid, the compound can be esterified utilizing an alkyl or aryl trichloroacetimidate with or without a catalyst such as $BF_3 \cdot Et_2O$ or methanesulfonic acid in a suitable solvent such as dichloromethane, ethyl acetate or cyclohexane. When $R^7$ or $R^8$ is nitro, the compound can be reduced to the respective amino compound most readily using tin dichloride in ethyl acetate at 40 to 100° C. or with hydrazine and Montmorillinite clay in ethanol at 40 to 100° C. or by catalytic hydrogenation in the presence of a catalyst such as palladium on carbon. When $R^7$ or $R^8$ is an amino or an alcohol, the compound can be acylated using one or more molar equivalents of suitable acylating agent. The acylating agent is generally a lower alkyl or aryl carboxylic acid anhydride or a lower alkyl or aryl carboxylic acid chloride. The reaction is run under standard conditions, for example the use of pyridine as solvent with or without a co-solvent such as dichloromethane at 0° C. to room temperature. When $R^7$ or $R^8$ is an alcohol it can be acylated with a lower alkyl or aryl carboxylic acid anhydride in the presence of magnesium iodide in diethyl ether at ambient temperature to reflux. When $R^3$ or $R^4$ is an alcohol, the compound can be alkylated under the conditions of the Mitsunobu Reaction (for a review see Oyo Mitsunobu *Synthesis*. 1981, 1–27). The other co-reagents necessary to effect the Mitsunobu Reaction include one or more molar equivalents of a lower alkyl azodicarboxylate diester such as diethyl azodicarboxylate and one or more molar equivalents of triarylphosphine such as triphenylphosphine in a suitable solvent such as diethyl ether, THF, benzene or toluene at temperatures ranging from −20° C. to 120° C. When $R^7$ or $R^8$ is a nitrile it can be reduced to the aminoalkyl compound by tin (II) chloride in refluxing ethyl acetate or by catalytic hydrogenation in the presence of a catalyst such as Raney nickel or by lithium aluminum hydride in an inert solvent such as ether. When $R^7$ or $R^8$ is a nitrile it can be converted to a carboxylic acid amide using standard conditions such as $HCl/H_2O$ at ambient temperatures to reflux or a milder procedure involves the reaction of the nitrile with an alkaline solution of hydrogen peroxide. When $R^7$ or $R^8$ is halogen or trifluoromethanesulfonate it can be converted to a 3-hydroxy-cyclobut-3-ene-4-yl-1,2-dione by methodology of Liebeskind et. al. (*J. Org. Chem.* 1990, 55, 5359). When $R^7$ or $R^8$ is an alcohol can be alkylated with a suitable alkylating agent such as one or more molar equivalents of alkyl halide in the presence a base such as potassium carbonate or sodium hydroxide in a suitable solvent such as THF, DMF or DMSO at temperatures ranging from 0° C. to 60° C. When $R^3$ or $R^4$ is a carboxcylic acid, the compound can be coupled to tetronic acid with a coupling reagent such as 1-(3-dimethylaminopropyl)-3-ethylcarbodiimide in the presence of a base such as triethylamine or DMAP in a suitable solvent such as DMF.

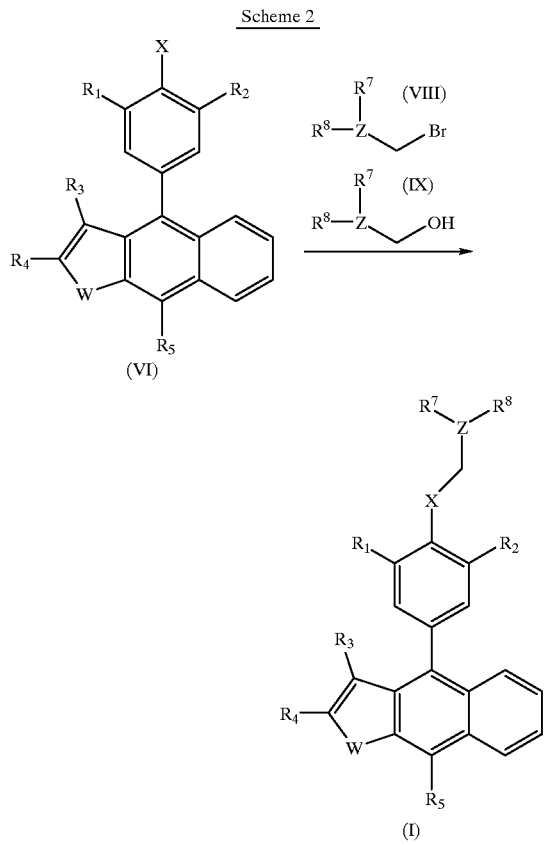

Scheme 2

Further derivatives of the compounds of formula (I) can be prepared by the following methods. The phenols and amines of formula (VI: X=NH₂, OH, —CH₂NH₂) can be alkylated with one or more molar equivalents of a haloalkylaryl or haloalkylheteroaryl of formula (VIII) and with one or more molar equivalents of an alkali metal carbonate such as potassium carbonate in a polar aprotic solvent such as DMF to afford the alkylated product of formula (I).

The phenols of formula (VI; X=OH) can be reacted with a hydroxyalkylaryl or hydroxyalkylheteroaryl of formula (IX) to afford the alkylated product of formula (I) under the conditions of the Mitsunobu Reactions (for a review see Oyo Mitsunobu *Synthesis.* 1981, 1–27). The other co-reagents necessary to effect the Mitsunobu Reaction include one or more molar equivalents of a lower alkyl azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The starting hydroxyalkylaryl or hydroxyalkylheteroaryl of formula (IX) is commercially available or can be prepared by standard synthetic methods. For example, an aryl or heteroaryl carboxcylic acid or ester can be reduced to the respective primary alcohol analog using standard conditions such as lithium aluminum hydride in ethyl ether. An aryl or heteroaryl aldehyde or ketone can be reduced to the respective primary alcohol analog using a metal catalyst, by sodium in alcohol, sodium borohydride and by lithium aluminum hydride.

The starting haloalkylaryl or haloalkylheteroaryl of formula (VIII) is commercially available or can be prepared by standard synthetic methods. For example, a hydroxyalkylaryl or hydroxyalkylheteroaryl of formula (IX) can be converted to the halo derivative with reagents such as thionyl chloride, phosphorous trihalides, triphenylphosphine dihalides or triphenylphosphine in the presence of carbon tetrachloride. Alternatively, the starting haloalkylaryl or haloalkylheteroaryl can be prepared by bromination of a alkylaryl or alkylheteroaryl with N-bromosuccinimide in the presence of AIBN in a solvent such as benzene with or without ultraviolet irradiation.

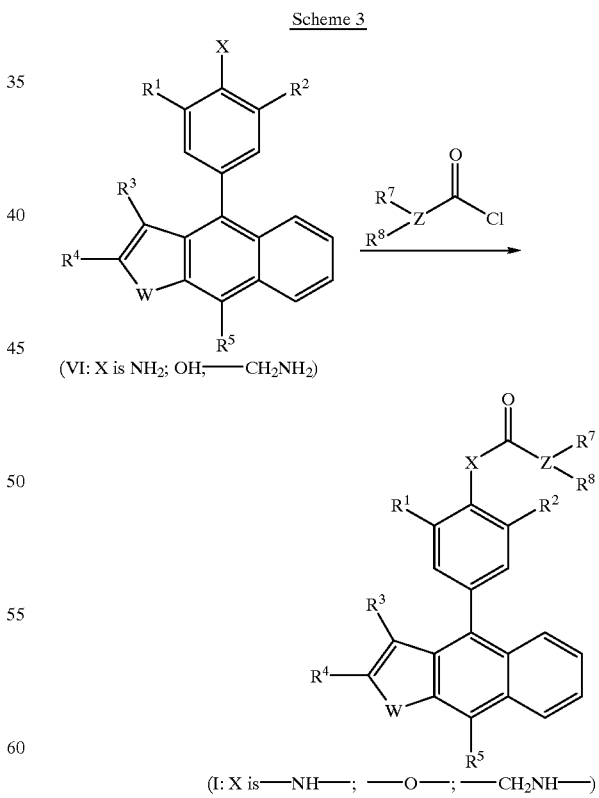

Scheme 3

Further derivatives of the compounds of formula (I) in Scheme 3 can be prepared by the following methods. The compounds of formula (VI: X=NH₂, OH, —CH₂NH₂) can be acylated on the phenolic oxygen or on the amino group using one or more molar equivalents of suitable acylating agent to provide the compounds of formula (I). The acylating agent is generally a aryl carboxylic acid anhydride or a aryl/heteroaryl carboxylic acid chloride. The reaction is run under standard conditions, for example the use of pyridine as solvent with or without a co-solvent such as dichloromethane at 0° C. to room temperature.

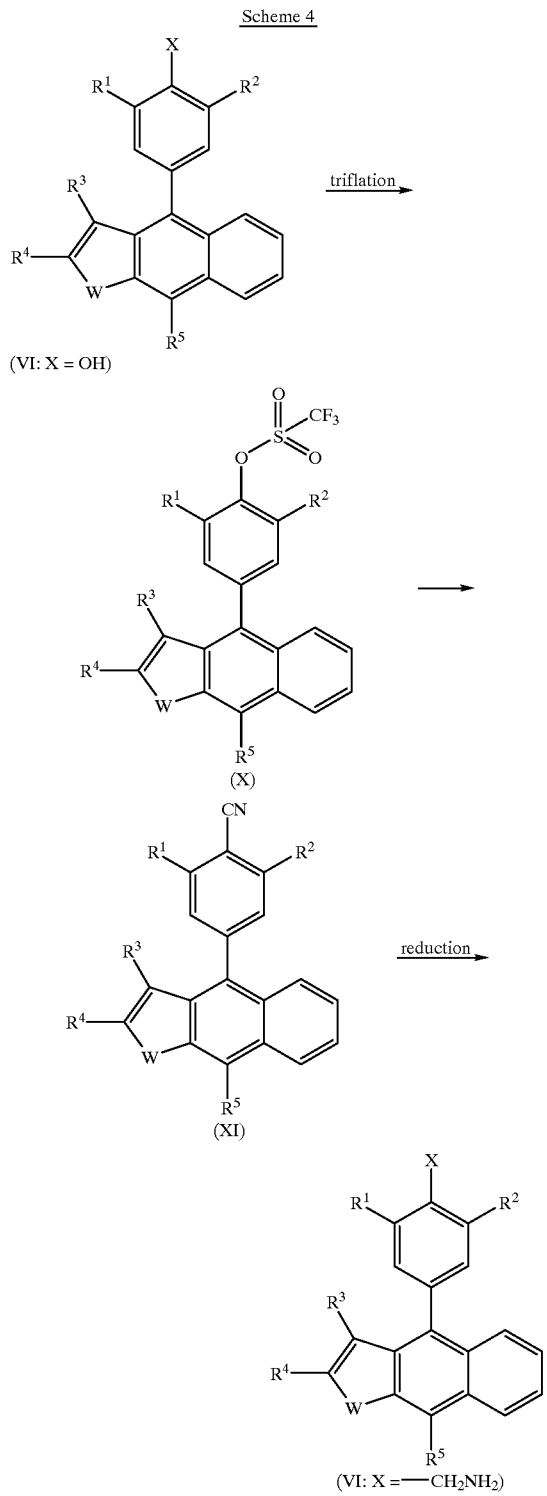

In a three step process (Scheme 4) compounds of formula (VI: X is OH) can be 5 converted to compounds of formula (VI: X=—CH$_2$NH$_2$). Reaction of compounds of formula (VI: X=OH) with trifluoromethanesulfonic anhydride or trifluoromethanesulfonic acid chloride in the presence of a organic base such as pyridine or triethylamnine in dichloromethane at 0° C. to ambient temperature provides compound (X). The triflate (X) can be converted to the carbonitrile (XI) with potassium cyanide or zinc cyanide in the presence of tetrakistriphenylphosphinenickel(0) which can be generated in situ from bistriphenylphosphinenickel (II) bromide and Zn/PPh$_3$. The nitrile (XI) can be reduced to the aminoalkyl compound (VI: X=—CH$_2$NH$_2$) by tin (II) chloride in refluxing ethyl acetate or by catalytic hydrogenation in the presence of a catalyst such as Raney nickel or by lithium aluminum hydride in an inert solvent such as ether.

The prepared compound (VI: X=—CH$_2$NH$_2$) can be used in Scheme 1 to prepared sulfonamides of formula (I: X=—CH$_2$NH—) or in Scheme 2 to prepare aminoalkyl derivatives of formula (I: X=—CH$_2$NH—) or in Scheme 3 to prepare amides of formula (I: X=—CH$_2$NH—).

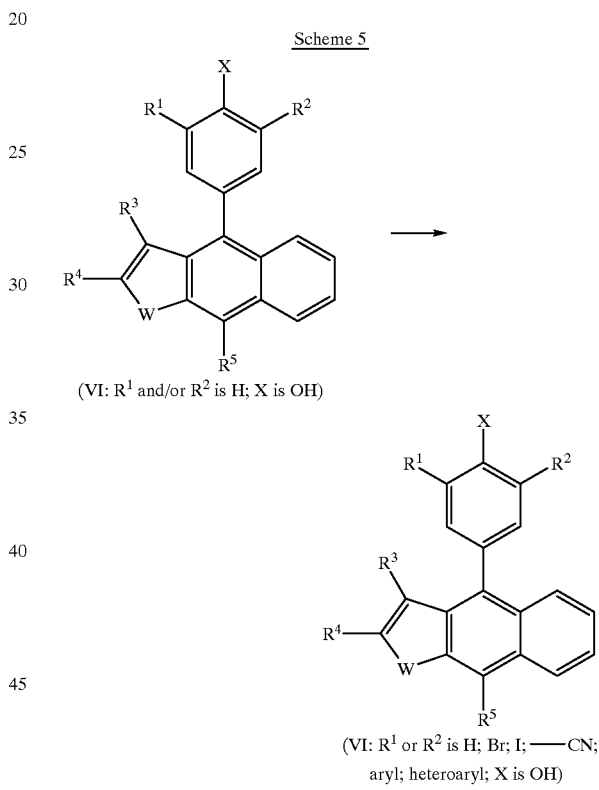

Further derivatives of the compounds of formula (VI) in Scheme 5 can be prepared by the following methods. The phenol of formula (VI: R$^1$ and R$^2$ is H; X is —OH) can be conveniently iodinated to the diiodophenol of formula (VI: R$^1$ and R$^2$ is I; X is —OH) using at least two molar equivalents of iodine in the presence of two or more molar equivalents of an alkali metal hydroxide such as NaOH in an alcohol solvent such as methanol at -20° C. to room temperature. Similarly the monoiodophenol (VI: R$^1$ or R$^2$ is I; X is —OH) can be prepared from the phenol of formula (VI: R$^1$ or R$^2$ is H; X is —OH) using one to 1.5 molar equivalents of iodine in the presence of at least one equivalent of an alkali metal hydroxide such as NaOH in a alcohol solvent such as methanol at -20° C. to room temperature. Either the monoiodophenol (VI: R$^2$ is I; X is —OH) or the diiodophenol (VI: R$^1$ and R$^2$ is I; X is —OH) can be converted to the respective methyl ether derivatives of formula (VI: R² is I; X is —OMe) or (VI: R¹ and R² is I; X is —OMe) by reacting the phenol moiety with a suitable methylating agent such as one or more molar equivalents of methyl iodide or dimethylsulfate employing a base such an alkali methyl carbonate or hydroxide such as potassium carbonate or sodium hydroxide in a suitable solvent such as THF, DMF or DMSO. The reaction is generally performed at temperatures ranging from 0° C. to 60° C. The mono or dibrominated derivatives of formula (VI: R¹ and/or R² is Br; X is —OMe) can be prepared in analogs fashion by substituting bromine for iodine in the sequence above.

The monoiodo methylether derivative of formula (VI: R² is I; X is —OMe) or the diiodo methylether of formula (VI: R¹ and R² is I; X is —OMe) can be reacted with one or more molar equivalents of copper (I) cyanide for the monoiodo analog or two or more molar equivalents of copper (I) cyanide for the diiodo derivative to produce the monocyanomethyl ether of formula (VI: R² is —CN; X is —OMe) or the dicyanomethyl ether of formula (VI: R¹ and R²is —CN; X is —OMe). The cyanation reaction is generally performed at temperatures ranging from 100° C. to 250° C. employing polar aprotic solvents such as DMF, 1-methyl-2-pyrrolidinone or HMPA. Quinoline or pyridine can also be used. The mono or dicyano methoxy analogs of formula (VI: R¹ and/or R² is —CN; X is —OMe); can be converted to the corresponding mono or dicyano phenol analogs of formula (VI: R¹ and/or R² is —CN; X is —OH) using standard demethylation procedures including one or more molar equivalents of boron tribromide or boron trichloride in dichloromethane at −78° C. to room temperature.

The mono or diiodo methylether derivative of formula (VI: R¹ and/or R²is I; X is —OMe) can be reacted with an arylboronic acid or heteroarylboronic acid to afford the product of formula (VI: R¹ and/or R² is aryl or heteroaryl; X is —OMe) under the conditions of the Suzuki Reaction (*Journal of the Chemical Society Chemical Communications* 1979 886 and *Synthetic Communications* 1981 11(7) 513). The other co-reagents necessary to effect the Suzuki Reaction include one or more molar equivalents of a metal catalyst such as tetrakis(triphenylphosphine)palladium or palladium (II) acetate and a base such as barium hydroxide octahydrate or sodium carbonate in a solvent such as benzene, toluene or DME/H₂O. The starting aryl or heteroaryl boronic acids are commercially available or can be prepared by standard synthetic methods. The mono or diaryl or mono or diheteroaryl methoxy analogs of formula (VI: R¹ and/or R² is aryl or heteroaryl; X is —OMe) can be converted to the corresponding mono or diaryl or mono or diheteroaryl phenol analogs of formula (VI: R¹ and/or R² is aryl or heteroaryl; X is OH) using standard demethylation procedures including one or more molar equivalents of boron tribromide or boron trichloride in dichloromethane at −78° C. to room temperature.

All the compounds prepared in Scheme 5 of formula (VI: R¹ and/or R²=H, I, Br, aryl, heteroaryl, nitrile) can be utilized in other schemes to prepared compounds of formula (I). For example, the prepared compound (VI: R¹ and/or R²=H, I, Br, aryl, heteroaryl, nitrile; X=OH) can be used in Scheme 1 to prepared sulfonyl esters of formula (I: R¹ and/or R²=H, I, Br, aryl, heteroaryl, nitrile) or in Scheme 2 to prepare —O-alkylated derivatives of formula (I: R¹ and/or R²=H, I, Br, aryl, heteroaryl, nitrile) or in Scheme 3 to prepare esters of formula (I: R¹ and/or R²=H, I, Br, aryl, heteroaryl, nitrile). All the compounds prepared in Scheme 5 of formula (VI: R¹ and/or R²=H, I, Br, aryl, heteroaryl, nitrile) can be utilized and further modified synthetically in Schemes 4, 6, 7 and 8.

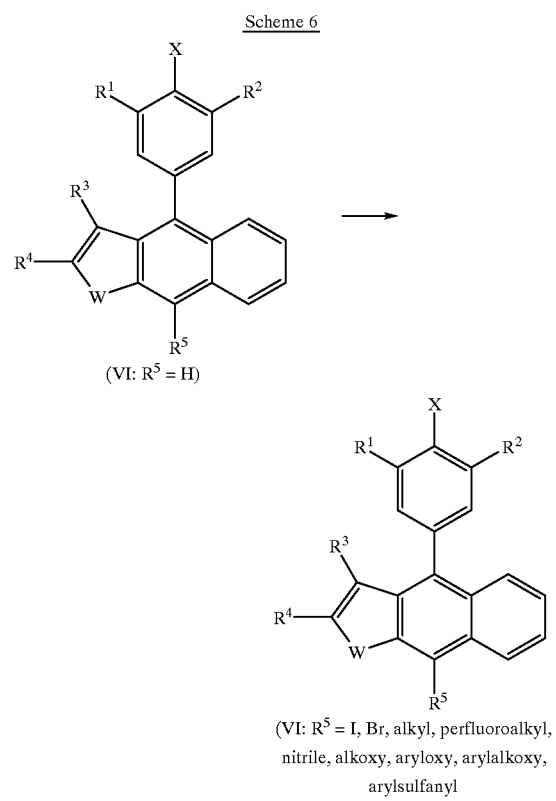

Scheme 6

Further derivatives of the compounds of formula (VI: X=OH; R⁵=H) in Scheme 6 can be prepared by the following methods. The compounds of formula (VI: X=OH; R⁵=H) can be acylated on the phenolic oxygen using one or more molar equivalents of suitable acylating agent to provide the compounds of formula (VI: X=O-acyl; R⁵=H). The acylating agent is generally a lower alkyl or aryl carboxylic acid anhydride or a lower alkyl or aryl carboxylic acid chloride. The reaction is run under standard conditions, for example the use of pyridine as solvent with or without a co-solvent such as dichloromethane at 0° C. to room temperature. The acylated phenols of formula (VI: X=O-acyl; R⁵=H) can then be brominated in the 9-position of the naphtho[2,3-b]thiophene or the naphtho[2,3-b]furan ring to form the acylated bromophenols of formula (VI: X=O-acyl; R⁵=Br). This bromination reaction is generally done using 1 to 1.3 molar equivalents of molecular bromine in the dark with a catalytic amount of iron (III) chloride in an inert solvent such as dichloromethane or carbon tetrachloride at temperatures ranging from −78° C. to room temperature.

Using a similar bromination reaction, the phenols of formula (VI: X=OH; R⁵=H) can then be brominated in the 9-position of the naphtho[2,3-b]thiophene or the naphtho[2, 3-b]furan ring to form the bromophenols of formula (VI: X=OH; R⁵=Br). This bromination reaction is generally done using 1 to 1.3 molar equivalents of molecular bromine in the dark with a catalytic amount of iron (III) chloride in an inert solvent such as dichloromethane or carbon tetrachloride at temperatures ranging from −78° C. to room temperature.

The acylated bromophenols of formula(VI: X=O-acyl; R⁵=Br) can be converted to the acylated cyanophenols of formula (VI: X=O-acyl; R⁵=—CN) by reaction with one or more molar equivalents of copper (I) cyanide. The cyanation reaction is generally performed at temperatures ranging from 100° C. to 250° C. employing polar aprotic solvents such as DMF, 1-methyl-2-pyrrolidinone or HMPA. Quinoline or pyridine can also be used.

The acyl group can then be removed from the prepared compounds of formula (VI: X=O-acyl; $R^5$=Br, CN) to provide compounds of formula (VI: X=OH; $R^5$=Br, CN) using standard conditions. These conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Acid conditions may also be employed in which the compound is reacted with one or more molar equivalents of a mineral acid such as HCl or sulfuric acid in water with or without a co-solvent such as THF at temperatures ranging from room temperature to 80° C.

The compounds of formula (VI: X=OH; $R^5$=H) can be sulfonylated on the phenolic oxygen using one or more molar equivalents of suitable sulfonylating agent to provide the sulfonic acid esters of formula (VI: X=—$OSO_2R'$; $R^5$=H). The sulfonylating (R') agent is generally a lower alkyl or aryl sulfonic acid anhydride or a lower alkyl or aryl sulfonic acid chloride. The reaction is run under standard conditions such as using pyridine as solvent with or without a co-solvent such as dichloromethane at 0° C. to room temperature.

The sulfonic acid esters of formula (VI: X=—$OSO_2R'$; $R^5$=H) can be treated with iodinating reagents to effect iodination at the 9-position of the naphtho[2,3-d]thiophene or the naphtho[2,3-d]furan ring to afford the iodo sulfonic acid esters of formula (VI: X=—$OSO_2R'$; $R^5$=I). A suitable iodinating reagent includes a mixture of 0.7 or more molar equivalents of molecular iodine and 0.25 or more molar equivalents of iodic acid in a mixture of THF and 80% aqueous acetic acid with a small amount of concentrated sulfuric acid at temperatures ranging from room temperature to 80° C.

The iodo sulfonic acid esters of formula (VI: X=—$OSO_2R'$; $R^5$=I) can be reacted with a reagent that catalyzes the exchange of the iodine atom in (VI) with a perfluoroalkyl group to afford the compound of formula (VI: X=—$OSO_2R'$; $R^5$=perfluoroalkyl). The reagent and conditions to effect this exchange include reacting (VI: X=—$OSO_2R'$; $R^5$=I) under anhydrous conditions with one to ten molar equivalents of a sodium perfluorocarboxylate ($RCO_2Na$: R is perfluoroalkyl) and one to five molar equivalents of copper (I) iodide in a high boiling inert solvent such as DMF, DMA or 1-methyl-2-pyrrolidinone at temperatures ranging from 140° C. to 200° C. Alternatively, the compound of formula (VI: X=—$OSO_2R'$; $R^5$=perfluoroalkyl) can be prepared from the compound of formula (VI: X=—$OSO_2R'$; $R^5$=I) by reacting the former with one to ten molar molar equivalents of a perfluoroalkyl iodide and one to five molar molar equivalents of activated $Cu^0$ in a high boiling inert solvent such as DMF, DMA or 1-methyl-2-pyrrolidinone at temperatures ranging from 140° C. to 200° C. Still, alternatively, the compound of formula (VI: X=—$OSO_2R'$; $R^5$=I) can be reacted with 0.5 to two molar equivalents of bis(trifluoromethyl)mercury and two to four molar equivalents of activated $Cu^0$ in a high boiling inert solvent such as DMF, DMA or 1-methyl-2-pyrrolidinone at temperatures ranging from 140° C. to 200° C. to produce the compound of (VI: X=—$OSO_2R'$; $R^5$=perfluoroalkyl).

Alkyl derivatives of the compound of formula (VI: X=—$OSO_2R'$; $R^5$=alkyl) can be prepared by reaction of (VI: X=—$OSO_2R'$; $R^5$=I) with three or more molar equivalents of lower tetra-alkyltin in the presence of a palladium catalyst such as 1 to 10 mole % of bis(triphenylphosphine)palladium II chloride in a suitable solvent such as DMF, DMA or 1-methyl-2-pyrrolidinone at temperatures ranging from 140° C. to 200° C.

The sulfonic ester group can then be removed from the sulfonic acid esters of formula (VI: X=—$OSO_2R'$; R5=alkyl, perfluoroalkyl) to provide the phenols of formula (VI: X=—OH; $R^5$ is alkyl, perfluoroalkyl) using standard conditions. These conditions include aqueous base in which one or more molar equivalents of alkali metal hydroxide such as sodium hydroxide is used in water with a co-solvent such as HF, dioxane or a lower alcohol such as methanol or mixtures of THF and a lower alcohol at temperatures ranging from room temperature to 110° C.

Alkoxy, arylalkoxy and aryloxy derivatives of the compound of formula (VI: X=OH; $R^5$=alkoxy, arylalkoxy, aryloxy) can be prepared by reaction of (VI: X=OH or —$OSO_2R'$; $R^5$=I) with three or more molar equivalents of lower alkali metal alkoxide such as sodium methoxide in the presence of a copper (I) or copper (II) catalyst such as 1 to 10 mole % copper (II) chloride in a suitable solvent such as DMF, DMA or 1-methyl-2-pyrrolidinone at temperatures ranging from 80° C. to 180° C. Under the reaction conditions, the sulfonic acid group is removed.

Alkylsulfanyl and arylsulfanyl derivatives of the compound of formula (VI: X=OH; $R^5$=alkylsulfanyl, arylsulfanyl) can be prepared by reaction of formula (VI: X=OH or —$OSO_2R'$; $R^5$=I) with one or more molar equivalents of the appropriate lower alkylthiol, arylthiol, thiopyridine or 2-N,N-dimethylamnoethyl-mercaptan, one or more molar equivalents of an alkali metal hydroxide such as sodium hydroxide, one or more molar equivalents of a copper (I) or copper (II) catalyst such as copper (I) oxide in a suitable solvent such as DMF, DMA or 1-methyl-2-pyrrolidinone at temperatures ranging from 100° C. to 180° C. Under the reaction conditions, the sulfonic acid group is removed.

The compounds of formula (VI: X=OH; $R^5$=I) can be converted to the respective methyl ether derivatives of formula (VI: X=—OMe; $R^5$=I) by reacting the phenol moiety with a suitable methylating agent such as one or more molar equivalents of methyl iodide or dimethylsulfate employing a base such an alkali methyl carbonate or hydroxide such as potassium carbonate or sodium hydroxide in a suitable solvent such as THF, DMF or DMSO. The reaction is generally performed at temperatures ranging from 0° C. to 60° C.

The iodo methylether derivative of formula (VI: X=—OMe; $R^5$=I) can be reacted with a arylboronic acid or heteroarylboronic acid to afford the product of formula (VI: $R^5$ is aryl or heteroaryl; X is —OMe) under the conditions of the Suzuki Reaction (*Journal of the Chemical Society Chemical Communications* 1979 886 and *Synthetic Communications* 1981 11(7) 513). The other co-reagents necessary to effect the Suzuki Reaction include one or more molar equivalents of a metal catalyst such as tetrakis (triphenylphosphine)palladium or palladium (II) acetate and a base such as barium hydroxide octahydrate or sodium carbonate in a solvent such as benzene, toluene or DME/$H_2O$. The starting aryl or heteroaryl boronic acids are commercially available or can be prepared by standard synthetic methods.

The methoxy analogs of formula (VI: $R^5$ is aryl or heteroaryl; X is —OMe) can be converted to the corresponding phenol analogs of formula (VI: $R^5$ is aryl or heteroaryl; X is OH) using standard demethylation procedures including one or more molar equivalents of boron tribromide or boron trichloride in dichloromethane at −78° C. to room temperature.

All the compounds prepared in Scheme 6 of formula (VI: X=OH; $R^5$=Br, I, alkyl, perfluoroalkyl, —CN, alkoxy, aryloxy, arylalkoxy, arylsulfanyl) can be utilized in other schemes to prepared compounds of formula (I). For example, the prepared compound (VI: X=OH; $R^5$=Br, I, alkyl, perfluoroalkyl, —CN, alkoxy, aryloxy, arylalkoxy, arylsulfanyl) can be used in Scheme 1 to prepared sulfonyl esters of formula (I: $R^5$=Br, I, alkyl, perfluoroalkyl, —CN, alkoxy, aryloxy, arylalkoxy, arylsulfanyl) or in Scheme 2 to prepare —O-alkylated derivatives of formula (I: $R^5$=Br, I, alkyl, perfluoroalkyl, —CN, alkoxy, aryloxy, arylalkoxy, arylsulfanyl) or in Scheme 3 to prepare esters of formula (I: $R^5$=Br, I, alkyl, perfluoroalkyl, —CN, alkoxy, aryloxy, arylalkoxy, arylsulfanyl). All the compounds prepared in Scheme 5 of formula (VI: $R^5$=Br, I, alkyl, perfluoroalkyl, —CN, alkoxy, aryloxy, arylalkoxy, arylsulfanyl) can be utilized and further modified synthetically in Schemes 4, 5, 7 and 8.

cycloamino compounds of formula (VI: $R^1$ or $R^2$=cycloamino).

All the compounds prepared in Scheme 7 of formula (VI: $R^1$ or $R^2$=$NO_2$, $NH_2$, alkylamino, dialkylamino, cycloalkylamino) can be utilized in other schemes to prepared compounds of formula (I). For example, the prepared compound (VI: $R^1$ or $R^2$=$NO_2$, $NH_2$, alkylamino, dialkylamino, cycloalkylamino; X=OH) can be used in Scheme 1 to prepared sulfonyl esters of formula (I: $R^1$ or $R^2$=$NO_2$, $NH_2$, alkylamino, dialkylamino, cycloalkylamino) or in Scheme 2 to prepare alkylated derivatives of formula (I: $R^1$ or $R^2$ =$NO_2$, $NH_2$, alkylamino, dialkylamino, cycloalkylamino) or in Scheme 3 to prepare esters of formula (I: $R^1$ or $R^2$=$NO_2$, $NH_2$, alkylamino, dialkylamino, cycloalkylamino). All the compounds prepared in Scheme 7 of formula (I: $R^1$ or $R^2$=$NO_2$, $NH_2$, alkylamino, dialkylamino, cycloalkylamino) can be utilized and further modified synthetically in Schemes 4, 5, 6 and 8.

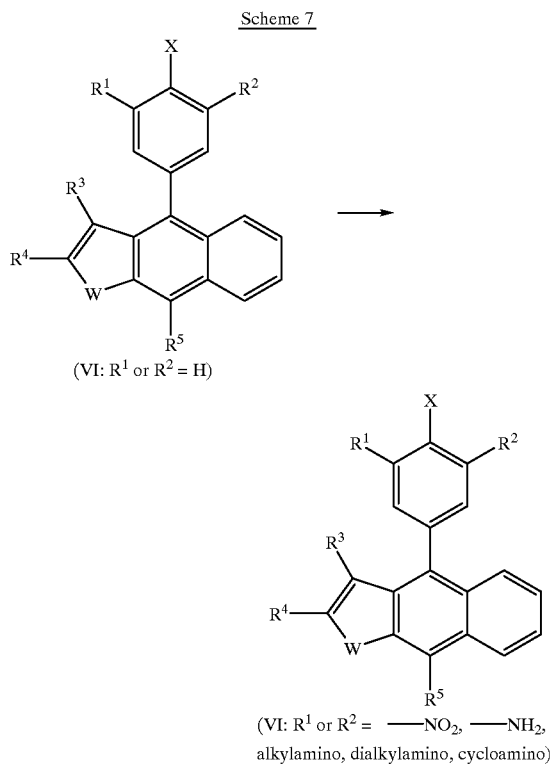

Scheme 7

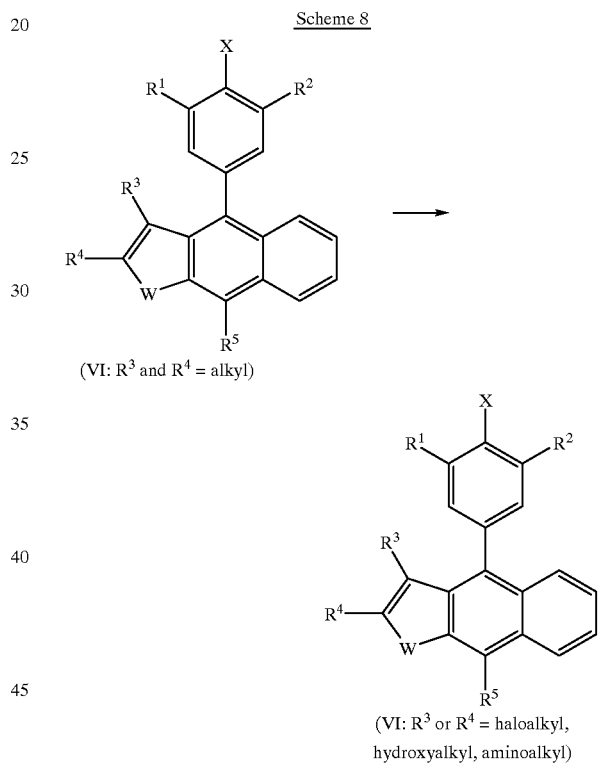

Scheme 8

The compounds of formula (VI: $R^1$ or $R^2$=H) can be mononitrated to the compounds of formula (VI: $R^1$ or $R^2$=$NO_2$) most conveniently using iron (III) trinitrate in a lower alcohol solvent.

The nitro compounds of formula (VI: $R^1$ or $R^2$=$NO_2$) can be reduced to the amino compounds of formula (VI: $R^1$ or $R^2$=$NH_2$) most readily using tin dichloride in ethylacetate at 40 to 100° C. or with hydrazine and Montmorillinite clay in ethanol at 40 to 100° C. or by catalytic hydrogenation in the presence of a catalyst such as palladium on carbon in a suitable solvent.

The amino compounds of formula (VI: $R^1$ or $R^2$=$NH_2$) can be mono or dialkylated with one or more molar equivalents of a haloalkyl and with one or more molar equivalents of an alkali metal carbonate such as potassium carbonate in a polar aprotic solvent such as DMF to afford the alkylated product of formula (VI). Using a dihaloalkyl reagent, such as commercially available 1,4-dibromobutane, can provide The acetates of formula (VI: X is O-acyl; $R^3$ and $R^4$ are alkyl) can be reacted with a halogenating agent, specifically one that causes benzylic type bromination or chlorination such as one or more molar equivalents of N-bromosuccinimide, N-chlorosuccinimide or sulfuryl chloride to provide the halo acetates of formula (VI: X is O-acyl; $R^3$ and/or $R^4$ are haloalkyl). This reaction is conveniently done in a suitable solvent such as dichloromethane or carbontetrachloride at temperatures ranging from 0° C. to room temperature.

The halo acetates of formula (VI: X is O-acyl; $R^3$ and/or $R^4$ are haloalkyl) can be reacted with one or more equivalents of nucleophiles such as amines (NHR"R'") (wherein R" and R'" is H, lower alkyl) in a suitable solvent such as THF, DMF or dichioromethane to provide the compounds of formula (VI: X is O-acyl; $R^3$ and/or $R^4$ are aminoalkyl).

The compounds of formula (VI: X is O-acyl; $R^3$ and/or $R^4$ are aminoalkyl) can be deacylated to produce the compounds of formula (VI: X is OH; $R^3$ and/or $R^4$ are aminoalkyl). The deacylation conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Acid conditions may also be employed in which the compound is reacted with one or more molar equivalents of a mineral acid such as HCl or sulfuric acid in water with or without a co-solvent such as THF at temperatures ranging from room temperature to 80° C.

All the compounds prepared in Scheme 8 of formula (VI: $R^3$ and/or $R^4$ are aminoalkyl, haloalkyl) can be utilized in other schemes to prepared compounds of formula (I). For example, the prepared compound (VI: $R^3$ and/or $R^4$ are aminoalkyl, haloalkyl; X=OH) can be used in Scheme 1 to prepared sulfonyl esters of formula (I: $R^3$ and/or $R^4$ are aminoalkyl, haloalkyl) or in Scheme 2 to prepare ether derivatives of formula (I: $R^3$ and/or $R^4$ are aminoalkyl, haloalkyl) or in Scheme 3 to prepare esters of formula (I: $R^3$ and/or $R^4$ are aminoalkyl, haloalkyl). All the compounds prepared in Scheme 8 of formula (VI: $R^3$ and/or $R^4$ are aminoalkyl, haloalkyl) can be utilized and further modified synthetically in Schemes 4, 5, 6 and 7.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedures which measure the inhibition of PTPase.

Inhibition of Tri-Phosphorylated Insulin Receptor Dodecaphosphopeptide Dephosphorylation by hPTP1B This standard pharmacological test procedure assesses the inhibition of recombinant, human protein tyrosine phosphatase (PTP) 1B activity. The substrate for the PTPase assay is a dodecaphosphopeptide corresponding to amino acids 1142–1153 of the insulin receptor (IR) kinase domain that was synthesized to contain phosphotyrosine at residues 1146, 1150 and 1151. The procedure used and results obtained are briefly described below.

Human, recombinant PTP1B (hPTP1B) was prepared as described by Goldstein (see Goldstein et al. *Mol. Cell Biochem.* 109, 107, 1992). The enzyme preparation used was stored in microtubes containing 4000–10000 μg/ml protein in 10mM Tris-HCl, 0.2 mM EDTA, 25 mM NaCl, 50% glycerol and 3 mM DTT.

Measurement of PTPase Activity.

The malachite green-ammonium molybdate method is used for the nanomolar detection of liberated phosphate by recombinant PTP1B as described (Lanzetta et al. *Anal. Biochem.* 100, 95, 1979). The assay was adapted for use with a 96-well microtiter platereader. The test procedure uses a dodecaphosphopeptide (TRDIpYETDpYpYRK) custom synthesized by AnaSpec, Inc. (San Jose, Calif.) corresponding to amino acids 1142–1153 of the insulin receptor β-subunit. Phosphotyrosine is incorporated at residues 1146, 1150, and 1151 as indicated. The recombinant hPTP1B is diluted to 1 μg/ml with buffer containing 10 mM Tris-HCl pH 7.4, 10 mM β-mercaptoethanol, and 30% Glycerol yielding an approximate activity of 10000–20000 nmoles inorganic phosphate released/min/mg protein. The diluted enzyme (166.5 μl) is added to 621 μl of reaction buffer containing 81.83 mM HEPES pH 7.4, 1.1 mM β-mercaptoethanol and then preincubated for 5 min at 37° C. with 2.51 μl of either test compound or DMSO as control. The dephosphorylation reaction is initiated by adding an aliquot (39.5 μl) of the recombinant hPTP1B:inhibitor pre-incubation mixture to the appropriate wells of a 96-well microtiter plate containing 10.5 μl of IR triphosphopeptide substrate pre-equilibrated to 37° C. A final concentration of 50 mM HEPES, 8.46 mM β-mercaptoethanol and 50 μM IR triphosphopeptide is achieved in the well. After 5 min at 37° C., the reaction is terminated by the addition of 200 μl of malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 μl MG/AM/Tw to wells containing 10.5 μl of IR triphosphopeptide substrate followed by the addition of 39.5 μl of the recombinant enzyme preincubated with either DMSO or drug. The colored product is allowed to develop at room temperature for 25 min. Sample absorbance is determined at 650 nm using a 96-well microtiter platereader (Bio-Tek). Samples and blanks are prepared in quadruplicates.

Calculations:

PTPase activity, expressed as nmoles of inorganic phosphate released/min/mg protein, is quantified by extrapolation from a standard curve using known quantities of potassium phosphate. Inhibition of recombinant hPTP1B by test compounds is calculated as a percentage of control (i.e. activity achieved in the presence of DMSO alone). A four parameter, non-linear logistic regression of PTPase activities using SAS release 6.08, PROC NLIN, is used for determining $IC_{50}$ values of test compounds. The following results were obtained.

| Example | $IC_{50}$ (μM) |
| --- | --- |
| 1 | 0.048 |
| 2 | 0.106 |
| 3 | 0.028 |
| 4 | 0.033 |
| 5 | 0.081 |
| 6 | 0.056 |
| 7 | 0.049 |
| 8 | 0.021 |
| 9 | 0.042 |
| 10 | 0.039 |
| 11 | 0.028 |
| 12 | 0.080 |
| 13 | 0.125 |
| 14 | 0.083 |
| 15 | 0.079 |
| 16 | 0.380 |
| 17 | 0.015 |
| 18 | 0.121 |
| 19 | 20% inhibition @ 1 (μM) |
| 20 | 0.193 |
| 21 | 0.196 |
| 22 | 17% inhibition @ 1 (μM) |
| 23 | 0.033 |
| 24 | 0.083 |
| 25 | 0.049 |
| 26 | 0.072 |
| 27 | 0.062 |
| 28 | 0.024 |
| 29 | 0.038 |
| 30 | 0.037 |

| Example | IC$_{50}$ ($\mu$M) |
| --- | --- |
| Phenylarsine oxide (reference standard) | 39.7 |
| Sodium orthovanadate (reference standard) | 244.8 |
| Ammonium molybdate tetrahydrate (reference standard) | 8.7 |

Based on the results obtained in the standard pharmacological test procedures, representative compounds of this invention have been shown to inhibit PTPase activity and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

4-[4-(9-Bromo-2,3-dimethyl-naghtho[2,3-b]thiophen-4-yl)-2-isopropyl-phenoxysulfonyl]-2 -hydroxy-benzoic acid Step 1

4-Chlorosulphonyl-2-hydroxybenzoic acid

At ambient temperature, to a stirred solution of commercial 4-aminosalicylic acid sodium salt dihydrate (50.25 g, 0.2379 mol) in H$_2$O (119 mL) was added a solution of 10% aq. NaOH (3.40 mL) and sodium nitrite (18.06 g, 0.2617 mol) in H$_2$O (44 mL). This solution was added to a vigorously stirred mixture of conc. HCL (153 mL) and glacial HOAc (76 mL) while maintaining the reaction temperature at −10° C. After 5 min., the dark orange suspension was added to a vigorously stirred mixture of copper (I) chloride (2.355 g, 0.02379 mol) in HOAc (128 mL) which had been previously cooled to 0° C. The reaction was saturated with sulfur dioxide for 0.5 h. The ice bath was removed and the reaction was stirred for 18 h. The reaction was quenched into crushed ice (2 L), allowed to warm to ambient temperature and filtered. The crude product was slurried in 20% THF/ether (1L), dried (MgSO$_4$), filtered and concentrated to give 36.32 g (64%) of the title compound as a red solid, mp 170–185° C.; $^1$H NMR (DMSO-d6) δ 7.11–7.16 (m, 2 H), 7.76 (d, 1 H), 13.2–14.4 (br. s, 2 H).

Step 2

2,3-Dimethylthiophene

A stirred mixture of commercial 3-methylthiophenecarboxaldehyde (20 g, 0.159 mol), hydrazine hydrate (31 mL) and diethylene glycol (72 mL) was refluxed for 20 min. After cooling below 100° C., potassium hydroxide (22.9 g, 0.408 mol) was slowly added and the reaction mixture was heated at 125 –130° C. for 1.5 h. The reaction mixture was cooled to ambient temperature, quenched with H$_2$O and extracted with ether. The combined ethereal extracts were washed with 5% aqueous HCl, brine, dried (MgSO$_4$) and concentrated. Purification on silica gel eluting with pentane provided the title compound as an oil (15.81 g, 89%): $^1$H NMR (CDCl3) δ 6.97 (d, 1H, J=8 Hz), 6.77 (d, 1 H, J=8 Hz), 2.35 (s, 3 H), 2.14 (s, 3 H).

Step 3

2-Benzyl-4,5-dimethylthiophene

At −78° C., to a stirred solution of 2,3-dimethylthiophene (5.00 g, 44.6 mmol) in THF (89.3 mL) was added dropwise 2.5M BuLi/hexanes (17.9 mL, 44.6 mmol). After the addition was complete, the dry ice/acetone bath was replaced with a water ice bath and the reaction was stirred for 0.75 h. At −78° C., to the reaction was added a solution of benzyl bromide (5.30 mL, 44.6 mmol) in THF (44.6 mL) that had been previously cooled to −78° C. After the addition was complete, the reaction was stirred for 18 h eventually warming to ambient temerature. The reaction was filtered through a silica gel pad eluting with 1% EtOAc/pet ether and the filtrate was concentrated. Purification on Biotage KP-Sil eluting with 1% EtOAc/pet ether gave 6.960 g (77%) of the title compound as an oil. $^1$H NMR (DMSO-d6) δ 2.01 (s, 3 H), 2.21 (s, 3 H), 3.98 (s, 2 H), 6.58 (s, 1 H), 7.18–7.37 (m, 5 H).

Step 4
(2-Benzyl-4,5-dimethylthiophen-3-yl)-(4-methoxy-3-isopropyl-phenyl)-methanone At ambient temperature, to a stirred solution containing 3-isopropyl-4-methoxybenzoic acid (27.00 g, 0.139 mol, RN-33537-78-9) and oxalyl chloride (13.3 mL, 0.153 mol) in $CH_2Cl_2$ (460 mL) was added N,N-DMF (5 drops). After 2 h, the reaction was cooled to −78° C. To the reaction was added tin (IV) chloride (17.89 mL, 0.153 mol) followed by a solution of 2-benzyl-4,5-dimethylthiophene (28.12 g, 0.139 mol) in $CH_2Cl_2$ (120 mL) that had been previously cooled to −78° C. After the addition was complete, the dry ice/acetone bath was removed and the reaction was stirred for 18 h, eventually warming to ambient temperature. The reaction was quenched into $H_2O$ (2 L) and extracted with ether. The combined ethereal extracts were sequentially washed with 1N HCl (3×500 mL), $H_2O$ (2×500 mL), $NaHCO_3$ (2×500 mL), brine (1×500 mL), dried ($MgSO_4$) and concentrated. Purification on silica gel, eluting with 5% EtOAc/pet. ether, gave 43.65 g (83%) of the title compound as an oil. $^1$H NMR (DMSO-d6) δ 1.13 (s, 3 H), 1.15 (s, 3 H), 1.81 (s, 3 H), 2.26 (s, 3 H), 3.23 (q, 1 H), 3.85 (s, 2 H), 3.88 (s, 3 H), 7.04–7.24 (m, 6 H), 7.55 (dd, 1 H), 7.63 (d, 1 H).

Step 5
4-(2,3-dimethyl-naphtho[2,3-b]thiophen-4-yl)-2-isopropyl-phenol

At −78° C., to a stirred solution of (2-benzyl-4,5-dimethylthiophen-3-yl)-(4-methoxy-3-isopropyl-phenyl)-methanone (6.48 g, 0.0178 mol) in $CH_2Cl_2$ (75 mL) was added dropwise boron tribromide (9.4 mL, 0.099 mol). After the addition was complete the dry ice/acetone bath was removed and the reaction was stirred for 2 h. The reaction was quenched into $KH_2PO_4$ (100 mL), extracted with $CH_2Cl_2$ and concentrated. Purification on silica gel, eluting with 5% EtOAc/pet. ether, gave 1.67 g (27%) of the title compound as a yellow solid. $^1$H NMR (DMSO-d6) β 9.49 (s, 1 H), 8.42 (s, 1 H), 7.94 (d, 1 H), 7.47–7.32 (m, 3 H), 7.01 (s, 1 H), 6.93 (s, 2 H), 3.32 (m, 1 H), 2.39 (s, 3 H), 1.59 (s, 3 H), 1.19 (d, 6 H).

Step 6
Acetic acid 2-isopropyl-4-(2,3-dimethyl-naphtho[2,3-b]thiophen-4-yl)-phenyl ester At 5° C., to a stirred solution of 4-(2,3-dimethyl-naphtho[2,3-b]thiophen-4-yl)-2-isopropyl-phenol (0.500 g, 1.44 mmol) in pyridine (3.5 mL) was added acetic anhydride (0.167 mL, 1.78 mmol). After 5.5 h, the reaction was quenched with $H_2O$, acidified and extracted with ether. The combined ethereal extracts were sequentially washed with $H_2O$, brine and concentrated. Purification on silica gel, eluting with 5 & 7% EtOAc/pet. ether, step gradient gave 0.384 g (69%) of the title compound as a white solid. $^1$H NMR (DMSO-d6) δ 8.49 (s, 1 H), 8.00–7.96 (d, 1 H), 7.48–7.31 (m, 4 H), 7.20 (s, 2 H), 3.10 (septet, 1 H), 2.40 (s, 3 H), 2.37 (s, 3 H), 1.56 (s, 3 H), 1.16 (d, 6 H).

Step 7
Acetic acid 2-isopropyl-4-(9-bromo-2,3-dimethyl-naphtho[2,3-b]thiophen-4-yl)-phenyl ester At −78° C., in the absence of light, to a stirred solution containing acetic acid 2-isopropyl-4-(2,3-dimethyl-naphtho[2,3-b]thiophen-4-yl)-phenyl ester (0.484 g, 1.25 mmol) and iron (III) chloride (0.011 g, 0.0662 mmol) in $CH_2Cl_2$ (11 mL) was added a solution of brornine (0.071 mL, 1.38 mmol) in $CH_2Cl_2$ (2 mL). After 40 min, the reaction was quenched with diluted aq. $NaHCO_3$, diluted with $H_2O$ (100 mL) and extracted with ether. The combined ethereal extracts were washed with $H_2O$ and concentrated. Purification on Biotage KP-Sil, eluting with 5% EtOAc/pet. ether, gave 0.321 g (55%) of the title compound as a pale yellow solid. $^1$H NMR (DMSO-d6) δ 8.20 (d, 1 H), 7.67–7.62 (m, 1 H), 7.52–7.43 (m, 2 H), 7.34 (d, 1 H), 7.22 (m, 2 H), 3.09 (septet, 1 H), 2.43 (s, 3 H), 2.37 (s, 3 H), 1.54 (s, 3 H), 1.16 and 1.15 (two doublets, 6 H, rotational isomers). MS(EI), [M+], 1 bromine isotope pattern, 466/468; Anal. Calc. for $C_{25}H_{23}BrO_2S$: C, 64.24, H, 4.96, N, 0.00. Found: C, 63.84, H, 4.90, N, 0.06.

Step 8
4-(9-Bromo-2,3-dimethyl-naphtho[2,3-b]thiophen-4-yl)-2-isoprol-phenol

At ambient temperature, to a stirred solution of acetic acid 2-isopropyl-4-(9-bromo-2,3-dimethyl-naphtho[2,3-b]thiophen-4-yl)-phenyl ester (0.315 g, 0.674 mmol)in THF:MeOH (11:7, 18 mL) was added 1N KOH (0.81 mL). After 1.5 h, the reaction was concentrated, slurried in $H_2O$ (50 mL), acidified with 10% HCl and extracted with ether. The combined ethereal extracts were washed with $H_2O$ (2×50 mL), concentrated and dried to give 0.340 g, of the title compound as an off white solid. $^1$H NMR (DMSO-d6) δ 9.56 (s, 1 H), 8.17 (d, 1 H), 7.64–7.60 (ddd, 1 H), 7.53–7.52 (d, 1 H), 7.46–7.42 (ddd, 1 H), 7.03 (d, 1 H), 6.97–6.91 (m, 2 H), 3.31–3.28 (m,1 H), 2.42 (s, 3 H), 1.58 (s, 3 H), 1.16 (d, 6 H). MS(EI), [M+], 1 bromine isotope pattern, 424/426; Anal. Calc. for $C_{23}H_{21}$,BrOS: C, 64.94, H, 4.98, N, 0.00. Found: C, 64.11, H, 4.99, N, 0.03.

Step 9
4-[4-(9-Bromo-2,3-dimethyl-naphtho[2,3-b]thiophen-4-yl)-2-isopropyl-phenoxysulfonyl]-2-hydroxy-benzoic acid At ambient temperature, to a stirred suspension of 4-(9-bromo-2,3-dimethyl-naphtho[2,3-b]thiophen-4-yl)-2-isopropyl-phenol (0.306 g, 0.744 mmol) in 0.05 M Tris buffer pH 9: THF (10:3, 3.56 mL, 0.2 M) was added 2.5N NaOH (0.285 mL, 0.713 mmol) followed by a minimal amount of THF to form a solution. After 0.5 h, the reaction was cooled to 5° C. To the reaction was added dropwise, a solution of 4-chlorosulphonyl-2-hydroxybenzoic acid (0.338 g, 1.43 mmol) in THF (2.85 mL, 0.5M) while maintaining the pH at 10 with the simultaneous addition of 2N NaOH. After the addition was completed, the reaction was allowed to warm to ambient temperature and stirred for 1.5 h. At 5° C. additional 4-chlorosulphonyl-2-hydroxybenzoic acid (0.338 g, 1.43 mmol) in THF (2.85 mL, 0.5 M) was added in the exact same manner as above and the reaction was stirred for 1.5 h. The reaction was quenched with 2N HCl (40 mL) and extracted with EtOAc. The combined organic extracts were washed with 2N HCl (3×), dried ($MgSO_4$) and concentrated. Purification on 2% $H_3PO_4$/MeOH treated Biotage KP-Sil eluting with a 15 & 25% EtOAc/Hexane step gradient gave 0.294 g, (66%) of the title compound as a yellow solid, mp >225° C.; $^1$H NMR (DMSO-d6): δ 0.96 (d, 3 H), 1.02 (d, 3 H), 1.48 (s, 3 H), 2.50 (s, 3 H), 3.08 (heptet, 1 H), 7.26–7.39 (m, 5 H), 7.43 (dd, 1 H), 7.50 (t, 1 H), 7.66 (t, 1 H), 8.05 (d, 1 H), 8.21 (d, 1 H). IR (KBr) 3425, 2950, 1675, 1400 and 1190 cm$^{-1}$. mass spectrum (−ESI), m/z 623/625 (M−H). Anal. Calcd. for $C_{30}H_{25}BrO_6S_2$: C, 57.60; H, 4.03; N, 0.00. Found: C, 57.88; H, 4.29 N, 0.09.

EXAMPLE 2
4-[4-(9-Bromo-2,3-dimethyl-naphtho[2,3-b]thiophen-4-yl)-2,6-dimethyl-phenoxysulfonyl]-2-hydroxy-benzoic acid Step 1
(2-Benzyl-4,5-dimethyl-thiophen-3-yl)-(4-methoxy-3,5-dimethyl-phenyl)-methanone To a suspension of 3,5-dimethyl-p-anisic acid (15.2 g, 84.4 mmol, RN-21553-46-8) in anhydrous methylene chloride (200 mL) at room temperature under nitrogen was added oxalyl chloride (9.6 mL, 110 mmol) and N,N-dimethylformamide (5 drops). After two hours the solvent was removed. The resulting residue was dissolved in anhydrous methylene chloride (200 mL), and added to 2,3-dimethyl-5-benzylthiophene (17.1 g, 84.4 mmol) under nitrogen. The resulting mixture was, cooled to −78° C., and tin(IV) chloride (10.8 mL, 92.8 mmol) was added quickly. The −78° C. bath was removed and the mixture was stirred at room temperature for 2 h. The reaction mixture was then poured onto ice water (1 L), and the resulting mixture was extracted once with diethyl ether (700 mL), and a second time with diethyl ether (400 mL). The combined diethyl ether extracts were washed with ice water(500 mL), dilute sodium bicarbonate (500 mL), water (500 mL), brine (1L), and then dried (Na2SO$_4$). Concentration under reduced pressure gave the title compound as a yellow oil (25.2 g, 82%): NMR (DMSO-d6) δ 7.40 (s, 2 H), 7.24–7.15 (m, 3 H), 7.06 (d, 2 H), 3.83 (s, 2 H), 3.70 (s, 3 H), 2.28 (s, 3 H), 2.26 (s, 6 H), 1.83 (s, 3 H).

Step 2

4-(2,3-Dimethyl-naphtho[2,3-b]thiophen-4-yl)-2,6-dimethyl-phenol (2-Benzyl-4,5-dimethyl-thiophen-3-yl)-(4-methoxy-3,5-dimethyl-phenyl)-methanone (25.2 g, 69.2 mmol) in anhydrous methylene chloride (420 mL) was placed under nitrogen and cooled to −78° C. Boron tribromide (20.9 mL, 221 mmol) was added dropwise over a period of 16 min, and the resulting mixture was stirred at −78° C. for 1.5 h. The −78° C. bath was removed and the reaction mixture was stirred at room temperature for 4 h. The reaction mixture was then poured onto ice water (1L) containing some sodium bisulfite, and the resulting mixture was extracted once with diethyl ether (1 L), and a second time with diethyl ether (300 mL). The combined diethyl ether extracts were washed twice with water (1 L), brine (1L), and then dried (Na2SO4). Concentration under reduced pressure afforded a dark residue which was combined with a second run done on (2-benzyl-4,5-dimethyl-thiophen-3-yl)-(4-methoxy-3,5-dimethyl-phenyl)-methanone (13.9 g, 38.1 mmol) and boron tribromide (11.5 mL, 122 mmol). Adsorption onto silica gel and chromatography with petroleum ether:ethyl acetate (90:10) gave a thick foamy amber residue identified as 4-(2,3-dimethyl-naphtho[2, 3-b]thiophen-4-yl)-2,6-dimethyl-phenol (24.0 g, 67%): NMR (DMSO-d6) δ 8.41 (s, 2 H), 7.93 (d, 1 H), 7.49–7.39 (m, 2 H), 7.34–7.28 (m, H), 6.87 (s, 2 H), 2.38 (s, 3 H), 2.23 (s, 6 H), 1.62 (s, 3 H). MS(EI), [M+] 332.

Step 3

Acetic acid 4-(2,3-dimethyl-naphtho[2,3-b]thiophen-4-yl)-2,6-dimethyl-phenyl ester To a solution of 4-(2,3-dimethyl-naphtho[2,3-b]thiophen-4-yl)-2,6-dimethyl-phenol (24.0 g, 72.2 mmol) in pyridine (200 mL) at 0° C. under nitrogen was added dropwise acetic anhydride (8.9 mL, 93.9 mmol) over a period of 10 min. After 45 min at 0° C., the reaction mixture was placed in the freezer for 18 h, then removed and stirred for 2 h in an ice bath that was allowed to warm to room temperature. The reaction mixture was poured onto water (1 L) and acidified with 10% hydrochloric acid to a pH of 1. The resulting mixture was extracted with diethyl ether (1 L), which was washed with 10% hydrochloric acid (1 L), twice with water (1 L), brine (700 mL), and dried (MgSO4). Concentration under reduced pressure and chromatography with petroleum ether:ethyl acetate (97:3) gave the title compound as a cream solid (22.4 g, 79%): NMR (CDCl3) δ 8.26 (s, 1 H), 7.87 (d, 1 H), 7.58 (d, 1 H), 7.44–7.40 (m, 1 H), 7.33–7.29 (m, 1 H), 7.07 (s, 2 H), 2.42 (s, 3 H), 2.41 (s, 3 H), 2.23 (s, 6 H), 1.67 (s, 3 H). MS(EI), [M+] 374. Anal. Calc. for C24H22O2S: C, 76.97, H, 5.92, N, 0.00. Found: C, 76.17, H, 5.75, N, 0.22.

Step 4

Acetic acid 4-(9-bromo-2,3-dimethyl-nophtho[2,3-b]thiophen-4-yl)-2,6-dimethyl-phenyl ester A solution of acetic acid 4-(2,3-dimethyl-naphtho[2,3-b]thiophen-4-yl)-2,6-dimethyl-phenyl ester (10.0 g, 26.7 mmol) and ferric chloride (0.23 g, 1.4 mmol) in anhydrous methylene chloride (231 mL) was placed at −78° C. under nitrogen. The reaction mixture was protected from light and a solution of bromine (1.5 mL, 29.4 mmol) in anhydrous methylene chloride (38 mL) was added dropwise over a period of 50 min. After 30 min the reaction was quenched with dilute sodium bisulfite, diluted with water, and the resulting mixture was extracted with diethyl ether. The diethyl ether layer was washed twice with water, brine, and then dried (MgSO4). Concentration under reduced pressure and chromatography with petroleum ether:ethyl acetate (97:3, then 95:5) gave the title compound as a white solid (6.7 g, 55%): NMR (DMSO-d6) δ 8.27 (d, 1 H), 7.60 (d, 1 H), 7.56–7.52 (ddd, 1 H), 7.38–7.34 (ddd, 1 H), 7.06 (s, 2 H), 2.43 (s, 3 H), 2.41 (s, 3 H), 2.22 (s, 6 H), 1.64 (s, 3 H). MS(EI), [M+], 1 bromine isotope pattern, 452/454. Anal. Calc. for C24H21BrO2S: C, 63.58, H, 4.67, N, 0.00. Found: C, 63.41, H, 4.45, N, 0.08.

Step 5

4-(9-Bromo-2,3-dimethyl-naphtho[2,3-b]thiophen-4-yl)-2,6-dimethyl-phenol

To a solution of acetic acid 4-(9-bromo-2,3-dimethyl-naphtho[2, 3-b]thiophen-4-yl)-2,6-dimethyl-phenyl ester (6.5 g, 14.3 mmol) in tetrahydrofuran (240 mL) and methanol (80 mL) at room temperature was added dropwise aqueous potassium hydroxide (17.2 mL of a 1N solution, 17.2 mmol). After 4 h at room temperature the reaction mixture was placed in the freezer for 18 h. The reaction was removed from the freezer and allowed to stir at room temperature. More aqueous potassium hydroxide (41.5 nL of a 1N solution, 41.5 mmol), tetrahydrofuran (50 mL), and methanol (10 mL) were added. The mixture was diluted with water (500 mL), acidified with 1N aqueous solution of hydrochloric acid, and extracted with diethyl ether. The diethyl ether layer was washed twice with water (500 mL), and dried (MgSO4). Concentration under reduced pressure gave a residue which was adsorbed onto silica gel. Chromatography with petroleum ether:ethyl acetate (97:3, then 95:5) gave the title compound as a white foamy solid (5.5 g, 93%): NMR (CDCl3) δ 8.41 (s, 1 H), 8.16 (d, 1 H), 7.64–7.54 (m, 2 H), 7.46–7.40 (m, 1 H), 6.89 (s, 2 H), 2.41 (s, 3 H), 2.23 (s, 6 H), 1.60 (s, 3 H). MS(-ESI), [M-H], 1 bromine isotope pattern, 409/411.

Step 6

4-[4-(9-Bromo-2,3-dimethyl-naphtho[2,3-b]thiophen-4-yl)-2,6-dimethyl-phenoxysulfonyl]-2-hydroxy-benzoic acid Using 4-(9-bromo-2,3-dimethyl-naphtho[2,3-b]thiophen-4-yl)-2,6-dimethyl-phenol (0.302 g, 0.744 mmol) and 4-chlorosulphonyl-2-hydroxybenzoic acid (1.09 g, 4.61 mmol) the title compound was prepared according to the procedure in Example 1, step 9. Purification on Dynamax C18 eluting with 85% CH$_3$CN/H$_2$O (0.1% TFA added) gave 0.20 g (44%) of the title compound as a yellow solid, mp >225° C.; $^1$H NMR (DMSO-d6) δ 1.59 (s, 3 H), 2.16 (s, 6 H), 2.45 (s, 3 H), 7.19 (S, 2 H), 7.46–7.52 (m, 4 H), 7.65–7.69 (m, 1 H), 8.07 (d, 1 H), 8.21 (d, 1 H). IR (KBr) 3450, 2900, 1675, 1385 and 1185 cm$^{-1}$. mass spectrum (−ESI), m/z 609/611 (M−H). Anal. Calcd. for C$_{29}$H$_{23}$BrO$_6$S$_2$.0.7H$_2$O: C, 55.81; H, 3.94 N, 0.00. Found: C, 55.93; H, 4.23 N, 0.12.

EXAMPLE 3

4-[4-(9-Bromo-2,3-dimethyl-naphtho[2,3-b]thiophen-4-yl)-2-cyclopentyl-phenoxysulfonyl]-2-hydroxy-benzoic acid Step 1

(2-Benzyl-4,5-dimethyl-thiophen-3-yl)-(3-cyclopgntyl-4-methoxy-phenyl)-methanone To a slurry of 3-cyclopentyl-p-anisic acid (5.0 g, 22.7 mmol, RN-59216-82-9) in anhydrous methylene chloride (60 mL) was added oxalyl chloride (2.4 mL, 27.2 mmol) and N,N-dimethylformamide (2 drops) at room temperature under nitrogen. After stirring for 1.5 h the reaction mixture was concentrated under reduced pressure. The residue was dissolved in carbon disulfide (32 mL) and the resulting solution was added to 2,3-dimethyl-5-benzylthiophene (5.1 g, 25.0 mmol). At −78° C. under nitrogen, tin(IV) chloride (2.9 mL, 25.0 mmol) was added, and the reaction mixture was then stirred at room temperature for 4 h. The solution was poured onto a mixture of ice and water (200 mL) and extracted with diethyl ether (200 mL). The diethyl ether layer was washed twice with sodium bicarbonate (50 mL) and once with brine (50 mL). Concentration under reduced pressure and chromatography with petroleum ether:ethyl acetate (95:5) gave the title compound as an amber oil (4.8 g, 52%): (DMSO-d6) δ 7.61–7.54 (m, 2 H), 7.24–7.14 (m, 3 H), 7.08–7.02 (m, 3 H), 3.87 (s, 3 H), 3.84 (s, 2 H), 3.42–3.30 (m, 1 H), 2.26 (s, 3 H), 2.00–1.85 (m, 2 H), 1.81 (s, 3 H), 1.74–1.58 (m, 4 H), 1.48–1.36 (m, 2 H). MS(EI), [M+] 404. Anal. Calc. for C26H28O2S: C, 77.19, H, 6.98, N, 0.00. Found: C, 76.26, H, 7.24, N, 0.04.

Step 2

2-Cyclopentyl-4-(2,3-dimethyl-naphtho[2,3-b]thiophen-4-yl)-phenol

To (2-benzyl4,5-dimethyl-thiophen-3-yl)-(3-cyclopentyl-4-methoxy-phenyl)-methanone (4.8 g, 11.7 mmol) in anhydrous methylene chloride (70 mL) at −78° C. under nitrogen was added dropwise over a period of 20 min boron tribromide (3.6 mL, 37.6 mmol). The reaction mixture was then allowed to stir at room temperature for 22 h. The solution was poured onto a mixture of ice and water (600 mL) and extracted with diethyl ether (800 mL). The diethyl ether layer was washed twice with water (500 mL) and once with brine (500 mL). Concentration under reduced pressure and chromatography with petroleum ether:ethyl acetate (97:3) gave the title compound as a white solid (3.4 g, 78%): mp 156–158° C.; (DMSO-d6) δ 9.48 (s, 1 H), 8.42 (s, 1 H), 7.93 (d, 1 H), 7.46–7.41 (m, 2 H), 7.35–7.30 (m, 1 H), 7.00 (s, 1 H), 6.95–6.90 (m, 2 H), 3.38–3.28 (m, 1 H), 2.39 (s, 3 H), 1.99–1.90 (m, 2 H), 1.68–1.47 (m, 6 H), 1.60 (s, 3 H). MS(EI): [M+] 372. Anal. Calc. for C25H24OS: C, 80.60, H, 6.49, N, 0.00. Found: C, 80.39, H, 6.43, N, 0.04.

Step 3

Acetic acid 2-cyclopentyl-4-(2,3-dimethyl-naphtho[2,3-b]thiophen-4-yl)-phenyl ester To 2-cyclopentyl-4-(2,3-dimethyl-naphtho[2,3-b]thiophen-4-yl)-phenol (2.8 g, 7.5 mmol) in anhydrous pyridine (20 mL) at room temperature under nitrogen was added dropwise acetic anhydride (0.92 mL, 9.8 mmol). The reaction mixture was placed in the refrigerator. After 41 h the reaction was diluted and acidified with 10% aqueous hydrochloric acid to a pH of 1. The mixture was extracted with diethyl ether (500 mL), and the diethyl ether layer was washed with 5% aqueous hydrochloric acid (100 mL), twice with water (100 mL), brine (100 mL), and then dried (MgSO4). Concentration under reduced pressure gave the title compound as a white solid (3.1 g, 98%): (DMSO-d6) δ 8.48 (s, 1 H), 7.97 (d, 1 H), 7.47–7.43 (m, 1 H), 7.38–7.36 (m, 2 H), 7.28 (s, 1 H), 7.19 (d, 2 H), 3.14 (quintet, 1 H), 2.40 (s, 3 H), 2.37 (s, 3 H), 1.99–1.91 (m, 2 H), 1.69–1.40 (m, 6 H), 1.56 (s, 3 H). MS(EI), [M+] 414. Anal. Calc. for C27H26O2S: C, 78.23, H, 6.32, N, 0.00. Found: C, 77.68, H, 6.39, N, 0.04.

Step 4

Acetic acid 2-cyclopentyl-4-(9-bromo-2,3-dimethyl-naphtho[2,3-b]thiophen-4-yl)-phenyl ester To acetic acid 2-cyclopentyl-4-(2,3-dimethyl-naphtho[2,3-b]thiophen-4-yl)-phenyl ester (2.9 g, 7.7 mmol) in anhydrous methylene chloride (68 mL) was added ferric chloride (66 mg, 0.41 mmol). The reaction mixture was placed under nitrogen and cooled to −78° C. The reaction mixture was protected from light and a solution of bromine (0.44 mL, 8.5 mmol) in anhydrous methylene chloride (11 mL) was added dropwise over a period of 15 min. After stirring at −78° C. for 45 min the reaction was quenched with dilute sodium bisulfite, and then poured into water (200 ML). The resulting mixture was extracted with diethyl ether (300 mL), and the diethyl ether layer was washed with water and then brine. Concentration under reduced pressure and chromatography with petroleum ether:ethyl acetate (95:5) gave the title compound as a white solid (2.7 g, 79%): (CDCl3): δ 8.28 (d, 1 H), 7.58–7.52 (m, 2 H), 7.39–7.34 (m, 1 H), 7.29 (d, 1 H), 7.18 (dd, 1 H), 7.14 and 7.13 (d, 1 H), 3.18 (quintet, 1 H 2.44 (s, 3 H), 2.40 (s, 3 H), 2.06–2.02 (m, 2 H), 1.75–1.45 (m containing a singlet at δ 1.60, 9 H). MS(EI), [M+], 1 bromine isotope pattern, 492/494; Anal. Calc. for C27H25BrO2S: C, 65.72, H, 5.11, N, 0.00. Found: C, 63.18, H, 4.96, N, 0.00.

Step 5

4-(9-Bromo-2,3-dimethyl-naphthol[2,3-b]thiophen-4-yl)-2-cyclopentyl-phenol

To acetic acid 2-cyclopentyl-4-(9-bromo-2,3-dimethyl-naphtho[2,3-b]thiophen-4-yl)-phenyl ester (2.7 g, 5.4 mmol) in tetrahydrofuran (88 mL) and methanol (30 mL) at room temperature was added dropwise potassium hydroxide (6.5 mL of a 1N solution, 6.5 mmol). After 1.5 h the reaction mixture was concentrated under reduced pressure. The resulting residue was combined with water (200 mL) and acidified with 10% aqueous hydrochloric acid to a pH of 1. The solution was extracted with diethyl ether (300 mL) and the diethyl ether layer was washed twice with water and dried (Na2SO4). Concentration under reduced pressure gave 2.4 g, (100%) of the title compound as a white solid; (DMSO-d6) δ 9.54 (s, 1 H), 8.16 (d, 1 H), 7.61 (m, 1 H), 7.52 (s, 1 H), 7.43 (m, 1 H), 7.03 (s, 1 H), 6.93 (m, 2 H), 3.32 (m, 1 H), 2.41 (s, 3 H), 1.94 (m, 2 H), 1.58 (s, 3 H), 1.72–1.42 (m, 6 H). MS(EI), [M+], 1 bromine isotope pattern, 450/452. Anal. Calc. for $C_{25}H_{23}BrOS$: C, 66.52 H, 5.13, N, 0.00. Found: C, 67.17, H, 5.25, N, 0.04.

Step 6

4-[4-(9-Bromo-2,3-dimethyl-naphtho[2,3-b]thiophen-4-yl)-2-cyclopentyl-phenoxysulfonyl]-2-hydroxy-benzoic acid Using 4-(9-bromo-2,3-dimethyl-naphtho[2,3-b]thiophen-4-yl)-2-cyclopentyl-phenol (0.289 g, 0.641 mmol) and 4-chlorosulphonyl-2-hydroxybenzoic acid (0.717 g, 3.03 mmol) the title compound was prepared according to the procedure in Example 1, step 9. Purification on Dynamax C18 eluting with 100% $CH_3CN$ (0.1% TFA added) gave 0.25 g (60%) of the title compound as a yellow solid, mp >225° C.; $^1H$ NMR (DMSO-d6) δ 1.31–1.36 (m, 2 H), 1.49–1.59 (m, 5 H), 1.61–1.63 (m, 3 H), 1.78–1.82 (m, 1 H), 2.44 (s, 3 H), 3.04–3.10 (m, 1 H), 7.25–7.31 (m, 3 H), 7.34–7.37 (m, 3 H), 7.50 (t, 1 H), 7.66 (t, 1 H), 8.02 (d, 1 H), 8.21 (d, 1 H). IR (KBr): 3425, 2900, 1650, 1400 and 1175 $cm^{-1}$. mass spectrum (−ESI), m/z 649/651 (M−H). Anal. Calcd. for $C_{32}H_{27}BrO_6S_2 \cdot 0.6H_2O$: C, 58.02; H, 4.29 N, 0.00. Found: C, 57.98; H, 4.35 N, 0.10.

EXAMPLE 4

4-[4-(9-Bromo-2,3-dimethyl-naphtho[2,3-b]thigphen-4-yl)-2,6-diisopropyl-phenoxysulfonyl]-2-hydroxy-benzoic acid Step 1

(2-Benzyl-4,5-dimethyl-thiophen-3-yl)-(3,5-diisopropyl-4-methoxy-phenyl)-methanone Using 3,5-diisopropyl-p-anisic acid (5.0 g, 21.2 mmol, RN-117439-59-5), oxalyl chloride (2.2 mL, 25.4 mmol), N,N-dimethylformamide (2 drops), 2,3-dimethyl-5-benzylthiophene (4.3 g, 21.2 mmol), tin(IV) chloride (5.0 mL, 42.7 mmol), and anhydrous methylene chloride (82 mL) the title compound was prepared according to the procedure in Example 2, step 1 to give 4.1 g (45%) NMR (DMSO-d6) δ 7.47 (s, 2 H), 7.23–7.12 (m, 3 H), 7.02–6.99 (m, 2 H), 3.86 (s, 2 H), 3.73 (s, 3 H), 3.31–3.20 (m, 2 H), 2.27 (s, 3 H), 1.82 (s, 3 H), 1.15 (d, 12 H). MS(EI), [M+] 420.

Step 2

4-(2,3-Dimethyl-naphtho[2,3-b]thiophen-4-yl)-2,6-diisopropyl-phenol

Using (2-benzyl-4,5-dimethyl-thiophen-3-yl)-(3,5-diisopropyl-4-methoxy-phenyl)-methanone (4.3 g, 10.1 mmol), boron tribromide (3.1 mL, 32.4 mmol), and methylene chloride (60 mL) the title compound was prepared according to the procedure in Example 2, step 2 to give 1.2 g (30%) as a yellow foam; NMR (DMSO-d6) δ 8.42 (s, 1 H), 8.24 (s, 1 H), 7.94 (d, 1 H), 7.48–7.32 (m, 3 H), 6.90 (s, 2 H), 3.45–3.35 (m, 2 H), 2.38 (s, 3 H), 1.57 (s, 3 H), 1.15 (d, 12 H). MS(-ESI), [M–H] 387.

Step 3

Acetic acid 4-(2,3-dimethyl-naphtho[2,3-b]thiophen-4-yl)-2,6-diisopropyl-phenyl ester Using 4-(2,3-dimethyl-naphtho[2,3-b]thiophen-4-yl)-2,6-diisopropyl-phenol (5.0 g, 13.7 mmol), acetic anhydride (1.68 mL, 17.8 mmol), and pyridine (85 mL) the title compound was prepared according to the procedure in Example 2, step 3 to give 5.37 g (91%) as a white solid, mp 243–245° C.; NMR (DMSO-d6) δ 8.49 (s, 1 H), 7.98 (d, 1 H), 7.49–7.39 (m, 3 H), 7.16 (s, 2 H), 3.01 (septet, 2 H), 2.43 (s, 3 H), 2.41 (s, 3 H), 1.56 (s, 3 H), 1.16 (d, 12 H). MS(EI), [M+] 430; Anal. Calc. for $C_{28}H_{30}O_2S$: C, 78.10, H, 7.02, N, 0.00. Found: C, 77.95, H, 7.04, N, 0.07.

Analytical HPLC indicates a major component (99.3%).

Step 4

Acetic acid 4-(9-bromo-2,3-dimethyl-nahtho[2,3-b]thiophen-4-yl)-2,6-diisopropyl-phenyl ester Using acetic acid 4-(2,3-dimethyl-naphtho[2,3-b]thiophen-4-yl)-2,6-diisopropyl-phenyl ester (0.80 g, 18.5 mmol), ferric chloride (16 mg, 0.1 mmol), bromine (0.13 mL, 2.6 mmol), and methylene chloride (19 mL) the title compound was prepared according to the procedure in Example 2, step 4 to give 0.53 g (56%) as a white solid; NMR (DMSO-d6) δ 8.21 (d, 1 H), 7.68–7.62 (m, 1 H), 7.60–7.42 (m, 2 H), 7.18 (s, 2 H), 3.00 (septet, 2 H), 2.42 (s, 6 H), 1.53 (s, 3 H), 1.14 (d, 12 H).

Step 5

4-(9-Bromo-2,3-dimethyl-naphtho[2,3-b]thiophen-4-yl)-2,6-diisorol-phenol

Using acetic acid 4-(9-bromo-2,3-dimethyl-naphtho[2,3-b]thiophen-4-yl)-2,6-diisopropyl-phenyl ester (0.52 g, 1.0 mmol), aqueous potassium hydroxide (1.64 mL of a 1 N solution, 1.6 mmol), tetrahydrofuran (18.5 mL), and methanol (11.5 nmL) the title compound was prepared according to the procedure in Example 2, step 5 to give 0.45 g (95%) as an off white solid, mp 212–216° C.; NMR (DMSO-d6) δ 8.30 (s, 1 H), 8.17 (d, 1 H), 7.61 (ddd, 1 H), 7.53 (d, 1 H), 7.44 (ddd, 1 H), 6.92 (s, 2 H ), 3.41 (septet, 2 H), 2.41 (s, 3 H), 1.55 (s, 3 H), 1.15 (d, 12 H). MS(EI), [M+], 1 bromine isotope pattern, 466/468. Anal. Calc. for $C_{26}H_{27}BrOS$: C, 66.80, H, 5.82, N, 0.00. Found: C, 66.17, H, 5.63, N, 0.06.

Step 6

4-[4-(9-Bromo-2,3-dimethyl-naphtho[2,3-b]thiophen-4-yl)-2,6-diisopropyl-phenoxysulfonyl]-2-hydroxy-benzoic acid Using 4-(9-bromo-2,3-dimethyl-naphtho[2,3-b]thiophen-4-yl)-2,6-diisopropyl-phenol (0.291 g, 0.623 mmol) and 4-chlorosulphonyl-2-hydroxybenzoic acid (0.768 g, 3.24 mmol) the title compound was prepared according to the procedure in Example 1, step 9. Purification on Dynamax C18 eluting with 100% $CH_3CN$ (0.1% TFA added) gave 0.09 g (22%) of the title compound as a white solid, mp >225° C.; $^1H$ NMR (DMSO-d6) δ 1.09 (t, 12 H), 1.54 (s, 3 H), 2.45 (s, 3 H), 3.14–3.22 (m, 2 H), 7.27 (s, 2 H), 7.41–7.46 (m, 2 H), 7.50–7.53 (m, 2 H), 7.65–7.69 (m, 1 H), 8.09 (d, 1 H), 8.21–8.23 (m, 1 H). IR (KBr) 3400, 2950, 1700, 1375 and 1180 $cm^{-1}$. mass spectrum (–ESI), m/z 665/667 (M–H). Anal. Calcd. for $C_{33}H_{31}BrO_6S_2 \cdot 1.7H_2O$: C, 56.76; H, 4.97 N, 0.00. Found: C, 56.73; H, 4.81 N, 0.12.

EXAMPLE 5

2-Acetoxy-4-[4-(9-bromo-2,3-dimethyl-naphtho[2,3-b]thiophen-4-yl)-2,6-dimethyl-phenoxysulfonyl]-benzoic acid A stirred suspension containing 4-[4-(9-bromo-2,3-dimethyl-naphtho[2,3-b]thiophen-4-yl)-2,6-dimethyl-phenoxysulfonyl]-2-hydroxy-benzoic acid (0.350 g, 0.572 mmol), acetic anhydride (4.55 mL) and magnesium iodide (0.159 g, 0.572 mmol) in anhydrous ethyl ether (10.0 mL, 0.05M) was refluxed for 0.5 h. The reaction was cooled to ambient temperature, quenched with $H_2O$ (150 mL), extracted with ether and concentrated. The crude product was dissolved in $THF:H_2O$ (1:1, 10 mL) and refluxed for 1 h. The reaction was cooled to ambient temperature, diluted with $H_2O$ (50 mL) and extracted with ether and EtOAc. The combined organic extracts were concentrated and purified on 2% $H_3PO_4$/MeOH treated silica gel, eluting with a 20 & 25% EtOAc/pet. ether step gradient to give 0.298 g (76%) of the title compound as a white solid; $^1H$ NMR (DMSO-d6) δ 1.58 (s, 3 H), 2.15 (s, 6 H), 2.30 (s, 3 H), 2.45 (s, 3 H), 7.20 (s, 2 H), 7.46–7.54 (m, 2 H), 7.67 (t, 1 H), 7.94 (d, 1 H), 8.05 (dd, 1 H), 8.20–8.25 (m, 2 H), 13.75–13.95 (br.s., 1 H). mass spectrum (–ESI), m/z 651/653 (M–H).

EXAMPLE 6

2-Acetoxy-4- [4-(9-bromo-2,3-dimethyl-naphtho[2,3-b]thiophen-4-yl)-2-cyclopentyl-phenoxysulfonyl]-benzoic acid Using 4-[4-(9-Bromo-2,3-dimethyl-naphtho[2,3-b]thiophen-4-yl)-2-cyclopentyl-phenoxysulfonyl]-2-hydroxy-benzoic acid (0.293 g, 0.450 mmol), acetic anhydride (3.6 mL, 38.2 mmol) and magnesium iodide (0.125 g, 0.450 mmol) the tidle compound was prepared according to the procedure in Example 5. Purification on 2% $H_3PO_4$/MeOH treated silica gel, eluting with a 10 & 30% EtOAc/pet. ether step gradient gave 0.245 g (79%) of the title compound as a colorless solid, mp 155–167° C.; $^1H$ NMR (DMSO-d6) δ 1.32–1.38 (m, 2 H), 1.49–1.53 (m, 5 H), 1.58–1.63 (m, 3 H), 1.78–1.80 (m, 1 H), 2.30 (s, 3 H), 2.45 (s, 3 H), 3.00–3.28 (m, 1 H), 7.25–7.29 (m, 2 H), 7.36–7.39 (m, 2 H), 7.50 (t, 1 H), 7.67 (t, 1 H), 7.83 (d, b 1 H), 7.93 (dd, 1 H), 8.19–8.22 (m, 2 H), 13.6–13.8 (br. s, 1 H). mass spectrum (–ESI), m/z 691/693 (M–H). Anal. Calcd. for $C_{34}H_{29}BrO_7S_2 \cdot 0.3H_2O$: C, 58.42; H, 4.27 N, 0.00. Found: C, 58.38; H, 4.55 N, 0.10.

EXAMPLE 7

2-Butyryloxy-4-[4-(9-bromo-2,3-dimethyl-naphtho[2,3-b]thiophen-4-yl)-2,6-dimethyl-phenoxysulfonyl]-benzoic acid Using 4-[4-(9-bromo-2,3-dimethyl-naphtho[2,3-b]thiophen-4-yl)-2,6-dimethyl-phenoxysulfonyl]-2-hydroxybenzoic acid (0.325 g, 0.531 mmol), butyric anhydride (4.23 mL) and magnesium iodide (0.148 g, 0.531 mmol) the title compound was prepared according to the procedure in Example 5. Purification on 2% $H_3PO_4$/MeOH treated Biotage KP-Sil, eluting with 20% EtOAc/pet. ether gave 0.164 g (45%) of the title compound as a white solid, mp 110–115° C.; $^1$H NMR (DMSO-d6) δ 0.97 (t, 3 H), 1.58 (s, 3 H), 1.66 (sextet, 2 H), 2.15 (s, 6 H), 2.45 (s, 3 H), 2.60 (t, 2 H), 7.19 (s, 2 H), 7.46–7.53 (m, 2 H), 7.67 (t, 1 H), 7.92 (d, 1 H), 8.05 (dd, 1 H), 8.23 (t, 2 H), 13.80–13.95 (br.s, 1 H). mass spectrum (−ESI), m/z 679/681 (M−H). Anal. Calcd. for $C_{33}H_{29}BrO_7S_2$: C, 58.15; H, 4.29 N, 0.00. Found: C, 57.83; H, 4.61 N, 0.04.

EXAMPLE 8

2-Benzoyloxy-4-[4-(9-bromo-2,3-dimethyl-naghtho[2,3-b]thiophen-4-yl)-2,6-dimethyl-phenoxysulfonyl]-benzoic acid Using 4-[4-(9-bromo-2,3-dimethyl-naphtho[2,3-b]thiophen-4-yl)-2,6-dimethyl-phenoxysulfonyl]-2-hydroxybenzoic acid (0.300 g, 0.491 mmol), benzoic anhydride (3.33 g) and magnesium iodide (0.137 g, 0.491 mmol) the title compound was prepared according to the procedure in Example 5. Purification on 2% $H_3PO_4$/MeOH treated silica gel, eluting with a 10 & 15% EtOAc/pet. ether step gradient gave 0.144 g (41%) of the title compound as a white solid, mp 172–185° C.; $^1$H NMR (DMSO-d6) δ 1.53 (s, 3 H), 2.15 (s, 6 H), 2.32 (s, 3 H), 7.18 (s, 2 H), 7.45–7.47 (m, 2 H), 7.59–7.66 (m, 3 H), 7.77 (t, 1 H), 8.05 (d, 1 H), 8.10–8.13 (m, 3 H), 8.19 (d, 1 H), 8.28 (d, 1 H). mass spectrum (−ESI), m/z 713/715 (M−H). Anal. Calcd. for $C_{36}H_{27}BrO_7S_2 \cdot 0.75H_2O$: C, 59.30; H, 3.94 N, 0.00. Found: C, 59.27; H, 3.83 N, 0.08.

EXAMPLE 9

2-Prolpionyloxy-4-[4-(9-bromo-2,3-dimethyl-naphtho[2,3-b]thiophen-4-yl)-2,6-dimethyl-phenoxysulfonyl]-benzoic acid Using 4-[4-(9-bromo-2,3-dimethyl-naphtho[2,3-b]thiophen-4-yl)-2,6-dimethyl-phenoxysulfonyl]-2-hydroxybenzoic acid (0.300 g, 0.491 mmol), propionic anhydride (1.80 mL) and magnesium iodide (0.137 g, 0.491 mmol) the title compound was prepared according to the procedure in Example 5. Purification on 2% $H_3PO_4$/MeOH treated silica gel, eluting with 20% EtOAc/pet. ether gave 0.228 g (70%) of the title compound as a white solid, mp 182–185° C.; $^1$H NMR (DMSO-d6) δ 1.14 (t, 3 H), 1.58 (s, 3 H), 2.15 (s, 6 H), 2.45 (s, 3 H), 2.63 (q, 2 H), 7.20 (s, 2 H), 7.48 (m, 2 H), 7.67 (t, 1 H), 7.93 (d, 1 H), 8.05 (dd, 1 H), 8.20–8.25 (m, 2 H). mass spectrum (+APCI), m/z 667/669 (M+H). Anal. Calcd. for $C_{32}H_{27}BrO_7S_2 \cdot 0.6H_2O$: C, 56.65; H, 4.19 N, 0.00. Found: C, 56.67; H, 4.29 N, 0.12.

EXAMPLE 10

5-[4-(9-Bromo-2,3-dimethyl-naphtho[2,3-b]thiophen-4-yl)-2-cyclopentyl-phenoxysulfonyl]-4-methoxy-thiophene-3-carboxylic acid Step 1

5-[4-(9-Bromo-2,3-dimethyl-naphtho[2,3-b]thiophen-4-yl)-2-cyclopentyl-phenoxysulfonyl]-4-methoxy-thiophene-3-carboxylic acid methyl ester At ambient temperature, to a stirred solution of 4-(9-bromo-2,3-dimethyl-naphtho[2,3-b]thiophen-4-yl)-2-cyclopentyl-phenol (0.308 g, 0.683 mmol) in N,N-DMF (3.41 mL) was added in one portion 60% NaH/mineral oil (27.3 mg, 0.683 mmol). After 0.5 h, to the reaction was added a solution of commercial 3-methoxy-4-(methoxycarbonyl)thiophene-2-sulphonylchloride (0.204 g, 0.751 mmol) in N,N-DMF (1.37 mL). After 1 h, the reaction was quenched with 1 N HCl (50 mL) combined with product from an identical experiment and extracted with 25% $CH_2Cl_2$/EtOAc. The combined organic extracts were washed with brine (3×), dried (MgSO$_4$) and concentrated. Purification on Biotage KP-Sil eluting with 15% EtOAc/pet. ether gave 0.593 g, (64%) of the title compound as a colorless solid. $^1$H NMR (DMSO-d6) δ 1.20–1.41 (m, 2 H), 1.43–1.83 (m, 9H), 2.44 (s, 3 H), 3.24 (quintet, 1 H), 3.85 (s, 3 H), 3.99 (s, 3 H), 7.24–7.38 (m, 4 H), 7.50 (t, 1 H), 7.66 (t, 1 H), 8.21 (d, 1 H), 8.81 (s, 1 H).

Step 2

5-[4-(9-Bromo-2,3-dimethyl-naphtho[2,3-b]thiophen-4-yl)-2-cyclopentyl-phenoxysulfonyl]-4-methoxy-thiophene-3-carboxylic acid At ambient temperature, to a stirred solution of 5-[4-(9-bromo-2,3-dimethyl-naphtho[2,3-b]thiophen-4-yl)-2-cyclopentyl-phenoxysulfonyl]-4-methoxy-thiophene-3-carboxylic acid methyl ester (0.722 g, 1.05 mmol) in THF:MeOH (3:2, 10 mL) was added 1N KOH (5.26 mL). After 1.5 h, the reaction was quenched with 1N HCl (40 mL) and extracted with EtOAc. The combined organic extracts were dried (MgSO$_4$) and concentrated. Purification on 2% $H_3PO_4$/MeOH treated Biotage KP-Sil, eluting with 25% EtOAc/hexane gave 0.596 g (85%) of the title compound as a white solid, mp >225° C.; $^1$H NMR (DMSO-d6) δ 1.34–1.39 (m, 2 H), 1.49–1.54 (m, 5 H), 1.62–1.73 (m, 3 H), 1.79–1.83 (m, 1 H), 2.43 (s, 3 H), 3.23 (quintet, 1 H), 3.97 (s, 3 H), 7.24 (dd, 1 H), 7.30 (d, 1 H), 7.34–7.36 (m, 2 H), 7.49 (t, 1 H), 7.64 (t, 1 H), 8.19 (d, 1 H), 8.72 (s, 1 H), 13.34 (br. s, 1 H). IR (KBr) 3400, 2950, 1690, 1375 and 860 cm$^{-1}$. mass spectrum (−ESI), m/z 669/671 (M−H). Anal. Calcd. for $C_{31}H_{27}BrO_6S_3$: C, 55.44; H, 4.05 N, 0.00. Found: C, 55.25; H, 4.11 N, 0.01.

EXAMPLE 11

5-[4-(9-Bromo-2,3-dimethyl-naphtho[2,3-b]thiophen-4-yl)-2-cyclopentyl-phenoxysulfonyl]-4-hydroxy-thiophene-3-carboxylic acid At −78° C., to a stirred suspension of 5-[4-(9-bromo-2,3-dimethyl-naphtho[2,3-b]thiophen-4-yl)-2-cyclopentyl-phenoxysulfonyl]-4-methoxy-thiophene-3-carboxylic acid (0.286 g, 0.426 mmol) in $CH_2Cl_2$ (2.86 mL) was added 1M $BBr_3$/$CH_2Cl_2$ (1.32 mL, 1.32 mmol). After the addition was complete the dry ice/acetone bath was replaced with an ice water bath and the reaction was stirred for 1 h. The reaction was quenched with crushed ice, diluted with $H_2O$ (40 mL) and extracted with EtOAc. The combined organic extracts were combined with product from an identical experiment and concentrated. Purification on 2% $H_3PO_4$/MeOH treated Biotage KP-Sil, eluting with 35% EtOAc/hexane gave 0.273 g (95%) of the title compound as a pale yellow solid, mp >230° C.; $^1$H NMR (DMSO-d6) δ 1.31–1.40 (m, 2 H), 1.47 (s, 3 H), 1.50–1.67 (m, 5 H), 1.80–1.83 (m, 1 H), 2.42 (s, 3 H), 3.32 (quintet, 1 H), 7.22 (dd, 1 H), 7.31–7.37 (m, 3 H), 7.48 (t, 1 H), 7.64 (t, 1 H), 8.19 (d, 1 H), 8.64 (s, 1 H). IR (KBr) 3400, 2950, 1650, 1375 and 1150 cm$^{-1}$. mass spectrum (−ACPI), n/z 665 (M−H). Anal. Calcd. for $C_{30}H_{25}BrO_6S_3 \cdot 0.5H_2O$: C, 54.05; H, 3.93 N, 0.00. Found: C, 54.09; H, 3.98 N, 0.05.

EXAMPLE 12
4-[2-Cyclopentyl-4-(2,3-dimethyl-naphtho[2,3-b]thiophen-4-yl)-phenoxysulfonyl]-2-hydroxy-benzoic acid Using 4-(2,3-dimethyl-naphtho[2,3-b]thiophen-4-yl)-2-cyclopentyl-phenol and 4-chlorosulphonyl-2-hydroxybenzoic acid the title compound was prepared according to the procedure in Example 1, step 9. Purification on 2% $H_3PO_4$/MeOH treated silica gel eluting with a 0 & 10% EtOAc/hexane step gradient gave 0.66 g of the title compound as a pale yellow solid, mp 230–237° C.; $^1$H NMR (DMSO-d6) δ 1.30–1.35 (m, 2 H), 1.45–1.52 (m, 5 H), 1.58–1.63 (m, 3 H), 2.40 (s, 2 H), 3.05 (q, 1 H), 7.21–7.29 (m, 4 H), 7.35–7.47 (m, 4 H), 7.97 (d, 1 H), 8.03 (d, 1 H), 8.49 (s, 1 H). IR (KBr) 2950, 1675, 1390, 1190 and 850 $cm^{-1}$. mass spectrum (-ESI), m/z 571 (M-H). Anal. Calcd. for $C_{32}H_{28}O_6S_2 \cdot 0.2H_2O$: C, 66.69; H, 4.97 N, 0.00. Found: C, 66.69; H, 5.01 N, 0.03.

EXAMPLE 13
4-[2-Cyclopentyl-4-(2,3-dimethyl-naphtho[2,3-b]furan-4-yl)-phenoxysulfonyl]-2-hydroxy-benzoic acid

Step 1
2-Benzyl-4,5-dimethylfuran

At -78° C., to a stirred solution of commercial 2,3-dimethylfuran (50 g, 0.520 mol) in THF (2.6 L) was added dropwise 1.6M n-BuLi/hexanes (325 mL, 0.520 mol). After the addition was complete, the dry ice/acetone bath was removed and the reaction was stirred for 1 h. At -78° C., to the reaction was added dropwise commercial benzyl bromide (62 mL, 0.520 mol). After the addition was complete the reaction was stirred at -78° C. for 6 h, the dry ice/acetone bath was removed and the reaction was stirred for 7 days. The reaction was concentrated in vacuo and purified on silica gel eluting with hexane to give 75.70 g (78%) of the title compound as a clear oil. $^1$H NMR (DMSO-d6) δ 1.83 (s, 3 H), 2.08 (s, 3 H), 3.83 (s, 2 H), 5.83 (s, 1 H), 7.16–7.30 (m, 5 H). mass spectrum (EI), m/z 186 (M+).

Step 2
(2-Benzyl-4,5-dimethyl-furan-3 -yl)-(3-cyclopentyl-4-methoxy-phenyl)-methanone The title compound was prepared according to the procedure in Example 1, step 4 using 3-cyclopentyl-4-methoxy-benzoic acid (10.00 g, 45.4 mmol, RN-59216-82-9), oxalyl chloride (4.4 mL, 50.4 mmol), N,N-DMF (5 drops), tin(IV) chloride (5.8 mL, 49.7 mmol) and 2-benzyl-4,5-dimethylfuran (10.1 g, 54.3 mmol) in $CH_2Cl_2$. The final organic extracts were concentrated to give 18.8 g of the title compound, synthetically pure. $^1$H NMR: consistent.

Step 3
4-(2,3-Dimethyl-naphtho[2,3-b]furan-4-yl)-2-cyclopentyl-phenol

The title compound was prepared according to the procedure in Example 1, step 5 using (2-benzyl-4,5-dimethyl-furan-3-yl)-(3-cyclopentyl-4-methoxy-phenyl)-methanone (18.8 g, 48.4 mmol) boron tribromide (34.8 mL, 0.367 mol) in $CH_2Cl_2$. Purification on silica gel eluting with a 2, 5, 10 and 20% EtOAc/hexane step gradient gave 1.55 g (10%) of the title compound. $^1$H NMR (DMSO-d6)δ 1.56–1.69 (m, 9 H), 1.96–1.97 (m, 5 H), 2.37 (s, 3 H), 3.33 (q, 1 H, masked by $H_2O$), 6.91–7.00 (m, 2 H), 7.06 (d, 1 H), 7.30 (t, 1 H), 7.41 (t, 1 H), 7.56 (d, 1 H), 7.91 (s, 1 H), 7.98 (d, 1 H), 9.48 (s, 1 H).

Step 4
4-[2-Cyclolentyl-4-(2,3-dimethyl-naphtho[2,3-b]furan-4-yl)-phenoxysulfonyl]-2-hydroxy-benzoic acid The title compound was prepared according to the procedure in Example 1, step 9, using 4-(2,3-dimethyl-naphtho[2,3-b]furan-4-yl)-2-cyclopentyl-phenol (0.663 g, 1.86 mmol) and 4-chlorosulphonyl-2-hydroxybenzoic acid (1.10 g, 4.66 mmol). Purification on 2% $H_3PO_4$/MeOH treated silica gel eluting with 20% EtOAc/hexane followed by recrystallization (ether/pet. ether) gave 0.66 g of the title compound as a pale yellow solid, mp 258–266° C. $^1$H NMR (DMSO-d6) δ 1.06–1.39 (m, 2 H), 1.42–1.55 (m, 5 H), 1.59–1.62 (m, 3 H), 1.75–1.82 (m, 1 H), 2.37 (s, 3 H), 3.04 (quintet, 1 H), 7.23–7.44 (m, 8 H), 7.97–8.03 (m, 3 H). IR (KBr) 3400, 2950, 1675, 1390 and 1190 $cm^{-1}$. mass spectrum (-ESI), m/z 555 (M-H). Anal. Calcd. for $C_{32}H_{28}O_7S \cdot 0.7H_2O$: C, 67.52; H, 5.21; N, 0.00. Found: C, 67.48; H, 4.94; N, 0.07.

EXAMPLE 14
4-[2-Bromo-4-(2,3-dimethyl-naphtho[2,3-b]furan-4-yl)-6-ethyl-phenoxysulfonyl]-2-hydroxy-benzoic acid

Step 1
4-(2-Chlorobenzoyl)-2-ethylanisole

At ambient temperature, to a stirred solution containing aluminum chloride (20 g, 0.150 mol), 2-chlorobenzoylchloride (19 mL, 0.150 mol) in $CH_2Cl_2$ (100 mL) was added dropwise 2-ethylanisole (20.4 g, 0.150 mol). After 4 h, the reaction was diluted with $CH_2Cl_2$ (400 mL) washed with aq. $KH_2PO_4$ (2×200 mL), brine (1×200 mL), filtered though Celite and concentrated to give 38.82 g (94%) of the title compound. $^1$H NMR: consistent.

Step 2
4-(2-Chlorobenzoyl)-2-ethylphenol

At -78° C., to a stirred solution of 4-(2-chlorobenzoyl)-2-ethylanisole (18 g, 65.5 mmol) in $CH_2Cl_2$ (295 mL) was added boron tribromide (12.4 mL, 0.131 mol). After the addition was complete, the reaction was allowed to warm to ambient temperature and stirred for 48 h. The reaction was slowly poured into crushed ice (200 g) and extracted with $CH_2Cl_2$. The organic extracts were washed with sat. aq. $KH_2PO_4$ (1×) and extracted with 2.5N NaOH. The aqueous extracts were washed with $CH_2Cl_2$ (1×), acidified with 2N HCl and extracted with $CH_2Cl_2$, dried ($Na_2SO_4$) and concentrated to give 14.48 g (85%) of the title compound. $^1$H NMR: consistent. mass spectrum (+ESI) m/z 261 (M+H). Anal. Calcd. for $C_{15}H_{13}ClO_2 \cdot 0.2H_2O$: C, 68.16; H, 5.11; N, 0.00. Found: C, 68.18; H, 5.15; N, 0.00.

Step 3
2-Bromo-4-(2-chlorobenzoyl)-6-ethylphenol

At ambient temperature, to a stirred solution containing 4-(2-chlorobenzoyl)-2-ethylphenol (13.62 g, 52.24 mmol) and pyridine (0.25 mL, 3.23 mmol) in $CH_2Cl_2$ (870 mL) was added dropwise bromine (3.3 mL, 62.29 mmol). After 48 h, the reaction was washed with 10% aq. $Na_2SO_4$ (1×180 mL), $H_2O$ (2×350 mL), brine (1×300 mL), dried ($Na_2SO_4$) and concentrated to give 16.50 g (93%) of the title compound. $^1$H NMR: consistent.

Step 4
2-Bromo-4-(2-chlorobenzoyl)-6-ethylanisole

At ambient temperature, to a stirred mixture containing 2-bromo-4-(2-chlorobenzoyl)-6-ethylphenol (14.56 g, 42.82 mmol) and $K_2CO_3$ (8.90 g, 64.5 mmol) in N,N-DMF (11.6 mL) was added iodomethane (3.98 mL, 64.4 mmol). After 48 h, the reaction was quenched with $H_2O$ (300 mL) and extracted with hexane. The organic extracts were washed with $H_2O$ (2×100 mL), brine (1×100 mL), dried ($Na_2SO_4$) and concentrated. Purification on Biotage KP-Sil eluting with a 0, 2.5 & 5% EtOAc/hexane step gradient gave 10.0 g (66%) of the title compound. $^1$H NMR: consistent. mass spectrum (EI) m/z 352 (M+). Anal. Calcd. for $C_{16}H_{14}BrClO_2 \cdot 0.2H_2O$: C, 53.79; H, 4.06; N, 0.00. Found: C, 53.89; H, 3.91; N, 0.08.

Step 5
3-Bromo-5-ethyl-4-methoxybenzoic acid

At ambient temperature, to a stirred mixture containing 2-bromo-4-(2-chlorobenzoyl)-6-ethylanisole (10.0 g, 28.2 mmol) and potassium t-butoxide (31.7 g, 0.283 mol) in ethylene glycol dimethyl ether (157 mL) was added $H_2O$ (1.52 mL). After 6 h, the reaction solids were collected by filtration and washed with ether (2×). The crude product was dissolved in $H_2O$ (200 mL), acidified with 2N HCl (pH <2) and stirred for 7 h. The precipitate was collected by filtration, washed with $H_2O$ (2×) and dried to give 5.37 g (73%) of the title compound. 1H NMR: consistent. mass spectrum (EI) m/z 258 (M+).

Step 6
(2-Benzyl-4,5-dimethyl-furan-3-yl)-(3-bromo-5-ethyl-4-methoxy-phenyl)-methanone The title compound was prepared according to the procedure in Example 1, step 4, using 3-bromo-5-ethyl-4-methoxybenzoic acid (4.95 g, 19.1 mmol), oxalyl chloride (1.8 mL, 20.7 mmol), N,N-DMF (2 drops), tin(IV) chloride (2.50 mL, 21.4 mmol) and 2-benzyl-2,3-dimethylfuran (4.30 g, 23.1 mmol) to give 7.85 g (96%) of the title compound. $^1$H NMR: consistent.

Step 7
2-Bromo-4-(2,3-dimethyl-naphtho[2,3-b]furan-4-yl)-6-ethyl-phenol

The title compound was prepared according to the procedure in Example 1, step 5, using (2-benzyl-4,5-dimethyl-furan-3-yl)-(3-bromo-5-ethyl-4-methoxy-phenyl)-methanone (7.85 g, 18.4 mmol) and boron tribromide (13.2 mL, 0.139 mol). Purification on silica gel eluting with 2% EtOAc/hexane, followed by trituration with hexane gave 0.85 g (12%) of the title compound as a white solid. $^1$H NMR (DMSO-d6) δ 1.15 (t, 3 H), 1.59 (s, 3 H), 2.37 (s, 3 H), 2.64–2.77 (m, 2 H), 7.09 (d, 1 H), 7.31 –7.35 (m, 2 H), 7.42 (d of t, 1 H), 7.52 (d, 1 H), 7.95 (s, 1 H), 7.99 (d, 1 H), 9.17 (s, 1 H). mass spectrum (EI) m/z 394 (M+). Anal. Calcd. for $C_{22}H_{19}BrO_2$: C, 66.85; H, 4.84; N, 0.00. Found: C, 67.07; H, 4.85, N, 0.05.

Step 8
4-[2-Bromo-4-(2,3-dimethyl-naphtho[2,3-b]furan-4-yl)-6-ethyl-phenoxysulfonyl]-2-hydroxy-benzoic acid The title compound was prepared according to the procedure in Example 1, step 9, using 2-bromo-4-(2,3-dimethyl-naphtho[2,3-b]furan-4-yl)-6-ethyl-phenol (0.458 g, 1.16 mmol) and 4-chlorosulphonyl-2-hydroxybenzoic acid (0.994 g, 4.19 mmol). Purification on 2% $H_3PO_4$/MeOH treated silica gel eluting with a 0 & 10% EtOAc/hexane step gradient gave 0.165 g of the title compound as a white solid, mp 238–243° C. $^1$H NMR (DMSO-d6) δ 1.13 (t, 3 H), 1.56 (s, 3 H), 2.39 (s, 3 H), 2.65–2.70 (m, 2 H), 7.37–7.60 (m, 7 H), 8.01–8.08 (m, 3 H). mass spectrum (–ESI) m/z 593 (M–H). Anal. Calcd. for $C_{29}H_{23}BrO_7S$: C, 58.50; H, 3.89; N, 0.00. Found: C, 58.91; H, 4.02; N, 0.05.

EXAMPLE 15
4-[4-(2,3-Dimethyl-naphtho[2,3-b]furan-4-yl)-2,6-diethyl-phenoxsulfonyl]-2-hydroxy-benzoic acid Step 1
4-Bromo-2,6-diethylbenzenediazonium tetrafluoroborate At 0° C., to a stirred solution of commercial 4-bromo-2,6-diethylaniline (10.0 g, 43.9 mmol) in absolute ethanol (219 mL) was added 48% aq. fluoboric acid (17.2 mL), followed by tert-butyl nitrite (5.7 mL, 48.0 mmol). After 0.5 h, the reaction was poured into ice cold ether (877 mL). The resulting precipitate was washed with cold ether and dried to give 9.39 g (66%) of the title compound. $^1$H NMR: consistent.

Step 2
4-Bromo-2,6-diethylanisole

A stirred solution containing 4-bromo-2,6-diethylbenzenediazonium tetrafluoroborate (17.25 g, 52.77 mmol) and freshly ground anhydrous zinc chloride (7.2 g, 52.9 mmol) in methanol (1.06 L) was refluxed for 6 h. The reaction was cooled to ambient temperature, quenched with $H_2O$ (1.2 L), saturated with solid sodium chloride and extracted with hexane. The combined organic extracts were washed with sat. aq. $NaHCO_3$ (1×100 mL), with $H_2O$ (1×100 mL), with brine (1×100 mL), dried ($Na_2SO_4$) and concentrated to give 12.0 g (94%) of title compound. $^1$H NMR: consistent. mass spectrum (EI) m/z 242 (M+).

Step 3
3,5-Diethyl-4-methoxybenzoic acid

At –78° C., to a stirred solution of 4-bromo-2,6-diethylanisole (12.0 g, 49.4 mmol) in THF (329 mL) was added dropwise n-butyllithium (27.2 mL, 43.5 mmol). After 3 h, the reaction was poured into crushed dry ice and allowed to warm to ambient temperature. The reaction mixture was diluted with EtOAc, concentrated, suspended in $H_2O$, acidified (pH 1), filtered and the collected solids washed with $H_2O$. The crude product was slurried in hexane (15 mL), collected by filtration and dried to give 6.76 g (66%) of the title compound. $^1$H NMR: consistent. IR (KBr): consistent. mass spectrum (EI) m/z 208 (M+). Anal. Calcd. for $C_{12}H_{16}O_3$: C, 69.21; H, 7.74; N, 0.00. Found: C, 69.28; H, 7.49; N, 0.07.

Step 4
(2-Benzyl-4,5-dimethyl-furan-3-yl)-(3,5-diethyl-4-methoxy-phenyl)-methanone The title compound was prepared according to the procedure in Example 1, step 4, using 3,5-diethyl-4-methoxybenzoic acid (10.66 g, 51.3 mmol), oxalyl chloride (4.90 mL, 56.3 mmol), N,N-DMF (2 drops), tin(IV) chloride (6.60 mL, 56.3 mmol) and 2-benzyl-4,5-dimethylfuran (11.4 g, 61.3 mmol) to give 22.0 g, of the title compound. $^1$H NMR δ1.13 (t, 6 H), 1.83 (s, 3 H), 2.19 (s, 3 H), 2.61 (q, 4 H), 3.74 (s, 3 H), 3.82 (s, 2 H), 7.05 (d, 2 H), 7.23–7.27 (m, 3 H), 7.42 (s, 2 H). mass spectrum (EI) m/z 376 (M+).

Step 5
4-(2,3-Dimethyl-naphtho[2,3-b]furan-4-yl)-2,6-diethyl-phenol

The title compound was prepared according to the procedure in Example 1, step 5, using (2-benzyl-4,5-dimethyl-furan-3-yl)-(3,5-diethyl-4-methoxy-phenyl)-methanone (22.0 g, 58.4 mmol) and boron tribromide (36.8 mL, 0.389 mol). Purification on Biotage KP-Sil, eluting with a 0, 2 & 5% EtOAc/hexane step gradient followed by trituration with hexane gave 1.34 g (8%), of the title compound as an off white solid. $^1$H NMR (DMSO-d6) δ 1.15 (t, 6 H), 1.59 (s, 3 H), 2.37 (s, 3 H), 2.59–2.72 (m, 4 H), 6.89 (s, 2 H), 7.29 (d of t, 1 H), 7.39 (d of t, 1 H), 7.56 (d, 1 H), 7.90 (s, 1 H), 7.96 (d, 1 H), 8.29 (s, 1 H). IR (KBr) 3540, 2960, 1475, 1180 and 1140 cm$^{-1}$. mass spectrum (EI) m/z 344 (M+). Anal. Calcd. for $C_{24}H_{24}O_2 \cdot 0.3H_2O$: C, 82.39; H, 7.09; N, 0.00. Found: C, 82.53; H, 7.11; N, 0.05.

Step 6
4-[4-(2,3-Dimethyl-naphtho[2,3-b]furan-4-yl)-2,6-diethyl-phenoxysulfonyl]-2-hydroxy-benzoic acid At ambient temperature, to a stirred suspension containing 4-(2, 3-dimethyl-naphtho[2,3-b]furan-4-yl)-2,6-diethyl-phenol (0.317 g, 0.919 mmol) and 0.01M aq. Borax (6 mL) in THF (9 mL) was added 2.5N NaOH (0.397 mL). To the reaction was added dropwise a solution of 4-chlorosulphonyl-2-hydroxybenzoic acid (0.653 g, 2.76 mmol) in THF (12 mL) while maintaining the pH at 10 with the simultaneous addition of 2.5N NaOH. After 48 h, additional 4-chlorosulphonyl-2-hydroxybenzoic acid (0.440 g, 1.86 mmol) in THF (12 mL) was added dropwise while maintaining the pH at 10 with the simultaneous addition of 2.5N NaOH and the reaction was stirred for an additional 48 h. The reaction was quenched with 1N HCl and extracted with ether. The combined ethereal extracts were washed with brine (1×), dried ($Na_2SO_4$) and concentrated. Purification on 2% $H_3PO_4$/MeOH treated silica gel eluting with 2% EtOAc/hexane followed by recrystallization (EtOAc/hexane) gave 95 mg (19%) of the title compound as an off white solid, mp 222–227° C. $^1$H NMR (DMSO-d6) δ 1.09 (t, 6 H), 1.55 (s, 3 H), 2.40 (s, 3 H), 2.55–2.60 (m, 4 H), 7.21 (s, 2 H), 7.37–7.39 (m, 1 H), 7.43–7.49 (m, 3 H), 7.53 (d of d, 1 H), 7.99 (s, 1 H), 8.01–8.04 (m, 1 H), 8.08 (d, 1 H). mass spectrum (−ESI) m/z 543 (M−H). Anal. Calcd. for $C_{31}H_{28}O_7S\cdot0.5H_2O$: C, 67.25; H, 5.28; N, 0.00. Found: C, 67.14; H, 5.21; N, 0.08.

EXAMPLE 16

4-[4-(9-Bromo-2,3-dimethyl-naphtho[2,3-b]thiophen-4-yl)-2, 6-dimethyl-phenoxysulfonyl]-2-hydroxy-benzoic acid tert-butyl ester At ambient temperature, to a stirred suspension of 4-[4-(9-bromo-2, 3-dimethyl-naphtho[2,3-b]thiophen-4-yl)-2,6-dimethyl-phenoxysulfonyl]-2-hydroxy-benzoic acid (1.033 g, 1.689 mmol) in EtOAc (16.89 mL) was added a solution of t-butyl 2,2,2-trichloroacetimidate (0.7690 g, 3.379 mmol) in cyclohexane (3.379 mL). After 24 h, the reaction was concentrated in vacuo, suspended in $CH_2Cl_2$ (10 mL), filtered through a 1"silica gel pad and eluted with 10% acetone/hexane. The filtrate was concentrated to give 0.778 g (69%) of the title compound as an off white solid, mp 168–172° C. $^1$H NMR (DMSO-d6) δ 1.57 (s, 12 H), 2.15 (s, 6 H), 2.43 (s, 3 H), 7.18 (s, 2 H), 7.45–7.55 (m, 4 H), 7.65 (t, 1 H), 7.96 (d, 1 H), 8.19 (d, 1 H), 10.75 (s, 1 H). IR (KBr) 3400, 2900, 1680, 1380 and 1140 cm$^{-1}$. mass spectrum (−ESI) m/z 665/667 (M−H). Anal. Calcd. for $C_{33}H_{31}BrO_6S_2$: C, 59.37; H, 4.68; N, 0.00. Found: C, 59.33; H, 4.44; N, 0.10.

EXAMPLE 17

2-(4-Methoxy-benzoyl)oxy-4-[4-(9-bromo-2,3-dimethyl-nahtho[2,3-b]thiohen-4-yl)-2,6-dimethyl-phenoxysulfonyl]-benzoic acid Step 1

2-(4-Methoxy-benzoyl)oxy-4-[4-(9-bromo-2,3-dimethyl-naphtho[2,3-b]thiophen-4-yl)-2,6-dimethyl-phenoxysulfonyl]-benzoic acid tert-butyl ester At ambient temperature, to a stirred solution containing 4-[4-(9-bromo-2, 3-dimethyl-naphtho[2,3-b]thiophen-4-yl)-2,6-dimethyl-phenoxysulfonyl]-2-hydroxy-benzoic acid tert-butyl ester (0.402 g, 0.602 mmol) and pyridine (0.292 mL, 3.61 mmol) in $CH_2Cl_2$ (6.02 mL) was added a solution of p-anisoyl chloride (0.208 g, 1.20 mmol) in $CH_2Cl_2$ (1.20 mL). After 18 h, the reaction was quenched with $H_2O$ (30 mL) and extracted with ether. The combined ethereal extracts were washed with sat. aq. $NaHCO_3$ (3×), with sat. aq. $CuSO_4$ (3×), with brine (3×), dried ($MgSO_4$) and concentrated. The crude product was purified on Biotage KP-Sil eluting with 15% acetone/hexane to give 0.354 g (73%) of the title compound. $^1$H NMR (DMSO-d6) δ 1.33 (s, 9 H), 1.54 (s, 3 H), 2.16 (s, 6 H), 2.34 (s, 3 H), 3.90 (s, 3 H), 7.13–7.19 (m, 4 H), 7.46–7.48 (m, 2 H), 7.60–7.70 (m, 1 H), 8.08–8.13 (m, 4 H), 8.20 (d, 2 H).

Step 2

2-(4-Methoxy-benzoyl)oxy-4-[4-(9-bromo-2,3-dimethyl-naghtho[2,3-b]thiophen-4-yl)-2,6-dimethyl-phenoxysulfonyl]-benzoic acid At ambient temperature, to a stirred solution of 2-(4-methoxy-benzoyl)oxy-4-[4-(9-bromo-2,3-dimethyl-naphtho[2,3-b]thiophen-4-yl)-2,6-dimethyl-phenoxysulfonyl]-benzoic acid tert-butyl ester (0.348 g, 0.434 mmol) in $CH_2Cl_2$ (3.48 mL) was added trifluoroacetic acid (3.48 mL). After 1.5 h, the reaction was quenched with $H_2O$ (50 mL) and extracted with EtOAc. The combined organic extracts were dried ($MgSO_4$) and concentrated. The crude product was purified on 2% $H_3PO_4$/MeOH treated Biotage KP-Sil eluting with a 15 & 25% EtOAc/hexane step gradient to give 0.296 g (91%) of the title compound as an off white solid, mp 174–177° C. $^1$H NMR (DMSO-d6) δ 1.53 (s, 3 H), 2.14 (s, 6 H), 2.32 (s, 3 H), 3.87 (s, 3 H), 7.12 (d, 2 H), 7.18 (s, 2 H), 7.44–7.49 (m, 2 H), 7.62–7.66 (m, 1 H), 7.98 (d, 1 H), 8.05–8.11 (m, 3 H), 8.19 (d, 1 H), 8.26 (d, 1 H), 13.5–14.0 (br s, 1 H). IR (KBr) 3400, 2900, 1740, 1360 and 1180 cm$^{-1}$. mass spectrum (−ESI) tn/z 743/745 (M−H). Anal. Calcd. for $C_{37}H_{29}BrO_8S_2\cdot 0.5H_2O$: C, 58.89; H, 4.01; N, 0.00. Found: C, 58.85; H, 3.89; N, 0.03.

EXAMPLE 18

5-[4-(2,3-Dimethyl-naphtho[2,3-b]thiophen-4-yl)-2,6-diethyl-phenoxysulfonyl]-4-methoxy-thiophene-3-carboxylic acid Step 1

(2-Benzyl-4,5-dimethylthiophen-3-yl)-(3.5-diethyl-4-methoxy-phenyl)-methanone

The title compound was prepared according to the procedure in Example 1, step 4, using 3,5-diethyl-4-methoxybenzoic acid (9.45 g, 45.5 mmol), oxalyl chloride (4.35 mL, 50.0 mmol), N,N-DMF (2 drops), tin(IV) chloride (5.85 mL, 50.0 mmol) and 2-benzyl-4,5-dimethylthiophene (11.0 g, 54.6 mmol) to give 17.67 g (99%) of the title compound. $^1$H NMR δ 1.13 (t, 6 H), 1.83 (s, 3 H), 2.27 (s, 3 H), 2.64 (q, 4 H), 3.73 (s, 3 H), 3.85 (s, 2 H), 7.04 (d, 2 H), 7.12–7.24 (m, 3 H), 7.43 (s, 2 H).

Step 2

4-(2,3-Dimethyl-naphtho[2,3-b]thiophen-4-yl)-2,6-diethyl-phenol

The title compound was prepared according to the procedure in Example 1, step 5, using (2-benzyl-4,5-dimethylthiophen-3-yl)-(3,5-diethyl-4-methoxy-phenyl)-methanone (17.67 g, 45.0 mmol) and boron tribromide (12.8 mL, 0.135 mol) to give 16.63 g, of the title compound. $^1$H NMR (DMSO-d6) δ 1.15 (t, 6 H), 1.61 (s, 3 H), 2.40 (s, 3 H), 2.59–2.73 (m, 4 H), 6.86 (s, 2 H), 7.32 (ddd, 1 H), 7.42 (ddd, 1 H), 7.47 (d, 1 H), 7.93 (d, 1 H), 8.31 (s, 1 H), 8.41 (s, 1 H). mass spectrum (+ESI) m/z 360 (M+).

Step 3

5-[4-(2,3-Dimethyl-naphtho[2,3-b]thiophen-4-yl)-2,6-diethyl-phenoxysulfonyl]-4-methoxy-thiophene-3-carboxylic acid methyl ester The title compound was prepared according to the procedure in Example 10, step 1, using 4-(2,3-dimethyl-naphtho[2,3-b]thiophen-4-yl)-2,6-diethyl-phenol (0.604 g, 1.67 mmol), 60% sodium hydride/mineral oil (0.0669 g, 1.67 mmol) and 3-methoxy-4-(methoxycarbonyl)thiophene-2-sulphonylchloride (0.499 g, 1.84 mmol) to give 0.629 g (63%) of the title compound. $^1$H NMR (DMSO-d6) δ 1.10 (t, 6 H), 1.59 (s, 3 H), 2.42 (s, 3 H), 2.57–2.68 (m, 4 H), 3.86 (s, 3 H), 4.02 (s, 3 H), 7.20 (s, 2 H), 7.38–7.50 (m, 3 H), 7.98 (d, 1 H), 8.50 (s, 1 H), 8.81 (s, 1 H).

Step 4
5-[4-(2,3-Dimethyl-naphtho[2,3-b]thiophen-4-yl)-2,6-diethyl-phenoxysulfonyl]-4-methoxy-thiophene-3-carboxylic acid The title compound was prepared according to the procedure in Example 10, step 2, using 5-[4-(2,3-dimethyl-naphtho[2,3-b]thiophen-4-yl)-2,6-diethyl-phenoxysulfonyl]-4-methoxy-thiophene-3-carboxylic acid methyl ester (0.608 g, 1.02 mmol) and 1N KOH (5.11 mL). Purification on 2% $H_3PO_4$/MeOH treated Biotage KP-Sil eluting with a 25, 40 & 60% EtOAc/hexane step gradient to give 0.390 g (66%) of the title compound as a white solid, mp >230° C. $^1$H NMR (DMSO-d6) δ 1.09 (t, 6 H), 1.58 (s, 3 H), 2.41 (s, 3 H), 2.57–2.69 (m, 4 H), 4.01 (s, 3 H), 7.18 (s, 2 H), 7.35–7.41 (m, 2 H), 7.44–7.48 (m, 1 H), 7.96 (d, 1 H), 8.49 (s, 1 H), 8.74 (s, 1 H), 13.39 (s, 1 H). IR (KBr) 2950, 1700, 1540, 1360 and 860 cm$^{-1}$. mass spectrum (−ESI) m/z 579 (M−H). Anal. Calcd. for $C_{30}H_{28}O_6S_3$: C, 62.05; H, 4.86; N, 0.00. Found: C, 25 62.15; H, 5.09; N, 0.06.

EXAMPLE 19

5-Pyridin-2-yl-thiophene-2-sulfonic acid 2-cyclopentyl-4-(2,3-dimethyl-naphtho[2,3-b]thiophen-4-yl)-phenyl ester The title compound was prepared according to the procedure in Example 10, step 1, using 4-(2,3-dimethyl-naphtho[2,3-b]thiophen-4-yl)-2-cyclopentyl-phenol (0.300 g, 0.805 mmol), 60% sodium hydride/mineral oil (0.032 g, 0.805 mmol) and commercial 5-(pyrid-2-yl)thiophene-2-sulphonyl chloride (0.243 g, 0.935 mmol). Purification on Biotage KP-Sil eluting with a 5 & 10% EtOAc/pet. ether step gradient gave 0.10 g (21%) of the title compound as a white solid, mp 141–142° C. $^1$H NMR (DMSO-d6) δ 1.29–1.38 (m, 2 H), 1.46–1.68 (m, 8 H), 1.82–1.85 (m, 1 H), 2.35 (s, 3 H), 3.16 (quintet, 1 H), 7.25–7.34 (m, 4 H), 7.39 (d, 1 H), 7.42–7.46 (m, 2 H), 7.92–7.97 (m, 3 H), 8.02 (d, 1 H), 8.13 (d, 1 H), 8.48 (s, 1 H), 8.62 (d, 1 H). mass spectrum (+ESI) m/z 596 (M+H). Anal. Calcd. for $C_{34}H_{29}NO_3S_3$ $0.4H^2O$: C, 67.72; H. 4.98; N, 2.32. Found: C, 67.79; H, 4.93; N, 2.35.

EXAMPLE 20

4-Benzoyloxy-5-[4-(2,3-dimethyl-naphtho[2,3-b]thiolphen-4-yl)-2,6-diethyl-phenoxysulfonyl]-thiophene-3-carboxylic acid Step 1

5-[4-(2,3-Dimethyl-naphtho[2,3-b]thiophen-4-yl)-2,6-diethyl-phenoxysulfonyl]-4-hydroxy-thiophene-3-carboxylic acid At −78° C., to a stirred solution of 5-[4-(2,3-dimethyl-naphtho[2,3-b]thiophen-4-yl)-2,6-diethyl-phenoxysulfonyl]-4-methoxy-thiophene-3-carboxylic acid (0.374 g, 0.644 mmol) in $CH_2Cl_2$ (3.74 mL) was added 1M boron tribromide/$CH_2Cl_2$ (2.00 mL). After the addition was complete, the dry ice/acetone bath was replaced with an ice water bath and the reaction was stirred for 1.5 h. The reaction was carefully quenched into crushed ice, diluted with $H_2O$ and extracted with EtOAc. The combined organic extracts were dried ($MgSO_4$) and concentrated. The crude product was purified on Biotage KP-Sil eluting with 40% EtOAc/hexane to give 0.300 g (82%) of the title compound as an off white solid. $^1$H NMR (DMSO-d6) δ 1.09 (t, 6 H), 1.59 (s, 3 H), 2.41 (s, 3 H), 2.62–2.73 (m, 4 H), 7.16 (s, 2 H), 7.38–7.47 (m, 3 H), 7.98 (d, 1 H), 8.49 (s, 1 H), 8.68 (s, 1 H).

Step 2

4-Benzoyloxy-5-[4-(2,3-dimethyl-nahtho[2,3-b]thiophen-4-yl)-2,6-diethyl-phenoxysulfonyl]-thiophene-3-carboxylic acid The title compound was prepared according to the procedure in Example 5, using 5-[4-(2,3-dimethyl-naphtho[2,3-b]thiophen-4-yl)-2,6-diethyl-phenoxysulfonyl]-4-hydroxy-thiophene-3-carboxylic acid (0.288 g, 0.508 mmol), benzoic anhydride (3.44 g) and magnesium iodide (0.141 g, 0.508 mmol). Purification on 2% $H_3PO_4$/MeOH treated Biotage KP-Sil, eluting with 25% EtOAc/hexane gave 0.199 g (58%) of the title compound as a white solid, mp 135–145° C. $^1$H NMR (DMSO-d6) δ 1.07 (t, 6 H), 1.54 (s, 3 H), 2.41 (s, 3 H), 2.58–2.70 (m, 4 H), 7.22 (s, 2 H), 7.35–7.37 (m, 2 H), 7.44–7.48 (m, 1 H), 7.64 (t, 2 H), 7.80 (t, 1 H), 7.98 (d, 1 H), 8.12 (d, 2 H), 8.50 (s, 1 H), 8.93–8.94 (m, 1 H), 13.4–13.7 (br s, 1 H). IR (KBr) 3400, 2950, 1760, 1700 and 1240 cm$^{-1}$. mass spectrum (−ESI), m/z 669 (M−H). Anal. Calcd. for $C_{36}H_{30}O_7S_3$: C, 64.46; H, 4.51; N, 0.00. Found: C, 64.19; H, 4.54; N, 0.17.

EXAMPLE 21

3-[2-Cyclopentyl-4-(2,3-dimethyl-naphtho[2,3-b]thiophen-4-yl)-phenoxysulfonyl]-benzoic acid The title compound was prepared according to the procedure in Example 1, step 9, using 4-(2,3-dimethyl-naphtho[2,3-b]thiophen-4-yl)-2-cyclopentyl-phenol (0.300 g, 0.805 mmol) and commercial 3-chlorosulphonylbenzoic acid (0.600 g, 2.71 mmol). Purification on 2% $H_3PO_4$/MeOH treated Biotage KP-Sil, eluting with 20% EtOAc/hexane followed by trituration with hexane gave 0.154 g (20%) of the title compound as a white solid, mp 120–128° C. $^1$H NMR (DMSO-d6) δ 1.23–1.36 (m, 2 H), 1.42–1.52 (m, 6 H), 1.55–1.69 (m, 3 H), 2.42 (s, 3 H), 2.96 (quintet, 1 H), 7.23–7.29 (m, 3 H), 7.33 (d, 1 H), 7.39 (ddd, 1 H), 7.47 (ddd, 1 H), 7.90 (t, 1 H), 7.97 (d, 1 H), 8.23 (dd, 1 H), 8.27–8.29 (m, 1 H), 8.37–8.39 (dt, 1 H), 8.50 (s, 1 H), 13.6–13.9 (br s, 1 H). IR (KBr) 3400, 2950, 1700, 1380 and 1190 cm$^{-1}$. mass spectrum (−ESI) m/z 555 (M−H). Anal. Calcd. for $C_{32}H_{28}O_5S_2 \cdot 0.65H_2O$: C, 67.62; H, 5.20; N, 0.00. Found: C, 67.60; H, 4.90; N, 0.09.

EXAMPLE 22

5-(2-Methylsulfanyl-pyrimidin-4-yl)-thiophene-2-sulfonic acid 2-cyclopentyl-4-(2,3-dimethyl-naphtho[2,3-b]thiophen-4-yl)-phenyl ester The title compound was prepared according to the procedure in Example 10, step 1, using 4-(2,3-dimethyl-naphtho[2,3-b]thiophen-4-yl)-2-cyclopentyl-phenol (0.300 g, 0.805 mmol), 60% sodium hydride/mineral oil (0.032 g, 0.805 mmol) and commercial 5-[2-(methylthio)pyrimidin-4-yl]thiophene-2-sulphonyl chloride (0.272 g, 0.886 mmol). Purification on Biotage KP-Sil eluting with 25% EtOAc/pet. ether gave 0.299 g (58%) of the title compound as a yellow solid, mp 100–110° C. $^1$H NMR (DMSO-d6) δ 1.32–1.37 (m, 2 H), 1.45–1.65 (m, 8 H), 1.84–1.90 (m, 1 H), 2.37 (s, 3 H), 2.55 (s, 3 H), 3.15 (quintet, 1 H), 7.25–7.38 (m, 5 H), 7.44 (ddd, 1 H), 7.90 (d, 1 H), 7.96 (d, 1 H), 8.08 (d, 1 H), 8.27 (d, 1 H), 8.48 (s, 1 H), 8.77 (d, 1 H). mass spectrum (+APCI) m/z 643 (M+H). $C_{34}H_{30}N_2O_3S_4$: C, 63.52; H, 4.70; N, 4.36. Found: C, 63.18; H, 4.46; N, 4.19.

EXAMPLE 23

2-Benzoyloxy-4-[4-(2,3-dimethyl-naphtho[2,3-b]thiophen-4-yl)-2,6-dimethyl-phenoxysulfonyl]-benzoic acid Step 1

4-[4-(2,3-Dimethyl-naphtho[2,3-b]thiophen-4-yl)-2,6-dimethyl-phenoxysulfonyl]-2-hydroxy-benzoic acid The title compound was prepared according to the procedure in Example 1, step 9, using 4-(2,3-dimethyl-naphtho

[2,3-b]thiophen-4-yl)-2,6-dimethyl-phenol (2.052 g, 6.171 mmol) and 4-chlorosulphonyl-2-hydroxybenzoic acid (5.840 g, 24.68 mmol). Purification on 2% $H_3PO_4$/MeOH treated Biotage KP-Sil, eluting with a 15 & 25% EtOAc/hexane step gradient gave 2.05 g (62%) of the title compound. $^1$H NMR (DMSO-d6) δ 1.60 (s, 3 H), 2.16 (s, 6 H), 2.42 (s, 3 H), 7.17 (s, 2 H), 7.38–7.40 (m, 2 H), 7.47–7.56 (m, 3 H), 7.98 (d, 1 H), 8.09 (d, 1 H), 8.50 (s, 1 H).

Step 2
4-[4-(2,3-dimethyl-naphtho[2,3-b]thiolphen-4-yl)-2,6-dimethyl-phenoxysulfonyl]-2-hydroxy-benzoic acid tert-butyl ester The title compound was prepared according to the procedure in Example 16, using 4-[4-(2,3-dimethyl-naphtho[2,3-b]thiophen-4-yl)-2,6-dimethyl-phenoxysulfonyl]-2-hydroxy-benzoic acid (0.100 g, 0.188 mmol) and t-butyl 2,2,2-trichloroacetimidate (0.0822 g, 0.375 mmol) to give 86 mg (78%) of the title compound. $^1$H NMR (DMSO-d6) δ 1.58 (s, 9 H), 1.60 (s, 3 H), 2.17 (s, 6 H), 2.42 (s, 3 H), 7.17 (s, 2 H), 7.38–7.40 (m, 2 H), 7.46–4.47 (m, 1 H), 7.54–7.57 (m, 2 H), 7.98 (d, 2 H), 8.50 (s, 1 H), 11.05 (s, 1 H).

Step 3
2-Benzoyloxy-4-[4-(2,3-dimethyl-naphtho[2,3-b]thiophen-4-yl)-2,6-dimethyl-phenoxysulfonyl]-benzoic acid tert-butyl ester The title compound was prepared according to the procedure in Example 17, step 1, using 4-[4-(2,3-dimethyl-naphtho[2,3-b]thiophen-4-yl)-2, 6-dimethyl-phenoxysulfonyl]-2-hydroxy-benzoic acid tert-butyl ester (0.072 g, 0.131 mmol), pyridine (63.4 μL, 0.784 mmol) and benzoyl chloride (30.5 μL, 0.262 mmol) to give a quantitative yield of the title compound. $^1$H NMR (DMSO-d6) δ 1.33 (s, 9 H), 1.57 (s, 3 H), 2.17 (s, 6 H), 2.31 (s, 3 H), 7.17 (s, 2 H), 7.36–7.48 (m, 3 H), 7.62–7.68 (m, 3 H), 7.78–7.82 (m, 1 H), 7.96 (t, 1 H), 8.10–8.24 (m, 4 H), 8.49 (s, 1 H).

Step 4
2-Benzoyloxy-4-[4-(23-dimethyl-naphtho[23-b]thiophen-4-yl)-2,6-dimethyl-phenoxysulfonyl]-benzoic acid The title compound was prepared according to the procedure in Example 17, step 2, using 2-benzoyloxy-4-[4-(2,3-dimethyl-naphtho[2,3-b]thiophen-4-yi)-2,6-dimethyl-phenoxysulfonyl]-benzoic acid tert-butyl ester to give 0.138 g of the title compound as a 15 white solid, mp 183–185° C. $^1$H NMR (DMSO-d6) δ 1.55 (s, 3 H), 2.16 (s, 6 H), 2.30 (s, 3 H), 7.15 (s, 2 H), 7.34–7.40 (m, 2 H), 7.45 (ddd, 1 H), 7.63 (t, 2 H), 7.76 (ddd, 1 H), 7.96 (d, 1 H), 8.05 (d, 1 H), 8.10–8.14 (m, 3 H), 8.28 (d, 1 H), 8.48 (s, 1 H), 13.7–13.9 (br s, 1 H). mass spectrum (+APCI) m/z 637 (M+H). Anal. Calcd. for $C_{36}H_{28}O_7S_2.0.4H_2O$: C, 67.15; H, 4.51; N, 0.00. Found: C, 67.23; H, 4.40; N, 0.10.

EXAMPLE 24

2-(4-Chloro-benzoyl)oxy-4-[4-(2,3-dimethyl-naphtho[2,3-b]thiophen-4-yl)-2,6-dimethyl-phenoxysulfonyll-benzoic acid Step 1
2-(4-Chloro-benzoyl)oxy-4-[4-(2,3 -dimethyl-naphtho[2,3-b]thiophen-4-yl)-2,6-dimethyl-phenoxysulfonyl]-benzoic acid tert-butyl ester The title compound was prepared according to the procedure in Example 17, step 1, using 4-[4-(2,3-dimethyl-naphtho[2,3-b]thiophen-4-yl)-2,6-dimethyl-phenoxysulfonyl]-2-hydroxy-benzoic acid tert-butyl ester (0.362 g, 0.615 mmol), pyridine (0.298 mL, 3.69 mmol) and 4-chlorobenzoyl chloride (0.156 mL, 1.23 mmol) to give the title compound. $^1$H NMR (DMSO-d6) δ 1.35 (s, 9 H), 1.57 (s, 3 H), 2.17 (s, 6 H), 2.33 (s, 3 H), 7.17 (s, 2 H), 7.35–7.40 (m, 2 H), 7.43 –7.48 (m, 1 H), 7.72 (d, 2 H), 7.98 (d, 1 H), 8.13–8.24 (m, 5 H), 8.50 (s, 1 H).

Step 2
2-(4-Chloro-benzoyl)oxy-4-[4-(2,3-dimethyl-naphtho[2,3-b]thiophen-4-yl)-2,6-dimethyl-phenoxysulfonyl]-benzoic acid The title compound was prepared according to the procedure in Example 17, step 2, using 2-(4-chloro-benzoyl)oxy-4-[4-(2,3-dimethyl-naphtho[2,3-b]thiophen-4-yl)-2,6-dimethyl-phenoxysulfonyl]-benzoic acid tert-butyl ester to give 0.282 g (68% two steps) of the title compound as a yellow solid, mp 186–193° C. $^1$H NMR (DMSO-d6) δ 1.56 (s, 3 H), 2.15 (s, 6 H), 2.32 (s, 3 H), 7.15 (s, 2 H), 7.34–7.37 (m, 2 H), 7.4 (ddd, 1 H), 7.68 (d, 2 H), 7.96 (d, 1 H), 8.08–8.13 (m, 4 H), 8.29 (d, 1 H), 8.48 (s, 1 H) 13.6–14.0 (br s, 1 H). IR (KBr) 3400, 2900, 1740, 1210 and 840 cm$^{-1}$. mass spectrum (+APCI) mn/z 671 (M+H). Anal. Calcd. for $C_{36}H_{27}ClO_7S_2.0.7H_2O$: C, 63.23; H, 4.19; N, 0.00. Found: C, 63.26; H, 3.89; N, 0.09.

EXAMPLE 25

Nicotinic acid 2-carboxy-5-[4-(2,3-dimethyl-naphtho[2,3-b]thiophen-4-yl)-2,6-dimethyl-phenoxysulfonyl]-phenyl ester Step 1
2-(Pyrid-3-ylcarbonyl)oxy-4-[4-(2,3-dimethyl-naphtho[2,3-b]thiophen-4-yl)-2,6-dimethyl-phenoxysulfonyl]-benzoic acid tert-butyl ester A stirred solution containing 4-[4-(2,3-dimethyl-naphtho[2,3-b]thiophen-4-yl)-2,6-dimethyl-phenoxysulfonyl]-2-hydroxy-benzoic acid tert-butyl ester (0.508 g, 0.863 mmol), nicotinic acid (0.108 g, 0.863 mmol), 2-chloro-1-methylpyridinium iodide (0.272 g, 1.04 mmol) and triethylamine (0.288 mL, 2.07 mmol) in $CH_2Cl_2$ (8.63 mL) was heated at 75° C. in a sealed tube for 3 days. The reaction was cooled to ambient temperature and concentrated. The crude product was purified on Biotage KP-Sil eluting with a 10 & 15% acetone/hexane step gradient to give 0.446 g (74%) of the title compound. $^1$H NMR (DMSO-d6) δ 1.35 (s, 9 H), 1.58 (s, 3 H), 2.18 (s, 6 H), 2.35 (s, 3 H), 7.18 (s, 2 H), 7.36–7.46 (m, 3 H), 7.68–7.72 (m, 1 H), 7.98 (d, 1 H), 8.15 (dd, 1 H), 8.22–8.26 (m, 2 H), 8.50–8.53 (m, 2 H), 8.95 (dd, 1 H), 9.30 (d, 1 H).

Step 2
Nicotinic acid 2-carboxy-5-[4-(2,3-dimethyl-naphtho[2,3-b]thiophen-4-yl)-2,6-dimethyl-phenoxysulfonyl]-phenyl ester The title compound was prepared according to the procedure in Example 17, step 2, using 2-(pyrid-3-ylcarbonyl)oxy-4-[4-(2,3-dimethyl-naphtho[2,3-b]thiophen-4-yl)-2,6-dimethyl-phenoxysulfonyl]-benzoic acid tert-butyl ester (0.436 g, 0.628 mmol). Purification on Biotage KP-Sil eluting with a 900:66:34, 850:100:50 & 800:133:67 (EtOAc:EtOH:$H_2O$) step gradient gave 59 mg (15%) of the title compound as a yellow solid, mp 161–171° C. $^1$H NMR (DMSO-d6) δ 1.57 (s, 3 H), 2.16 (s, 6 H), 2.33 (s, 3 H), 7.16 (s, 2 H), 7.35–7.37 (m, 2 H), 7.44 (ddd, 1 H), 7.67 (dd, 1 H), 7.96 (d, 1 H), 8.12–8.17 (m, 2 H), 8.30 (d, 1 H), 8.46–8.48 (m, 2 H), 8.92 (s, 1 H), 9.26 (s, 1 H), 13.7–14.1 (br s, 1 H). mass spectrum (–APCI) m/z 636 (M–H). Anal. Calcd. for $C_{35}H_{27}NO_7S_2$ 1.3$H_2O$: C, 63.58; H, 4.51; N, 2.12. Found: C, 63.59; H, 4.33; N, 1.89.

EXAMPLE 26

Nicotinic acid 2-carboxy-5-[4-(9-bromo-2,3-dimethyl-naphtho[2,3-b]thiophen-4-yl)-2,6-dimethyl-phenoxysulfonyl]-phenyl ester Step 1
2-(Pyrid-3-ylcarbonyloxy-4-[4-(9-bromo-2,3-dimethyl-naphtho[2,3-b]thiolphen-4-yl)-2,6-dimethyl-phenoxysulfonyl]-benzoic acid tert-butyl ester The title compound was prepared according to the procedure in Example 25, step 1, using 4-[4-(9-bromo-2,3- dimethyl-naphtho[2,3-b]thiophen-4-yl)-2,6-dimethyl-phenoxysulfonyl]-2-hydroxy-benzoic acid tert-butyl ester (0.500 g, 0.749 mmol), nicotinic acid (0.092 g, 0.749 mmol), 2-chloro-1-methylpyridinium iodide (0.230 g, 0.899 mmol) and triethylamine (0.251 mL, 1.80 mmol). Purification on Biotage KP-Sil eluting with 20% EtOAc/hexane gave 0.460 g, (80%) of the title compound. $^1$H NMR (DMSO-d6) 6 1.34 (s, 9 H), 1.55 (s, 3 H), 2.16 (s, 6 H), 2.36 (s, 3 H), 7.19 (s, 2 H), 7.45–7.46 (m, 2 H), 7.61–7.71 (m, 2 H), 8.12–8.25 (m, 4 H), 8.50 (ddd, 1 H), 8.94 (d, 1 H), 9.29 (s, 1 H).

Step 2

Nicotinic acid 2-carboxy-5-[4-(9-bromo-2,3-dimethyl-naphtho[2,3-b]thiophen-4-yl)-2,6-dimethyl-phenoxysulfonyl]-phenyl ester The title compound was prepared according to the procedure in Example 17, step 2, using 2-(pyrid-3-ylcarbonyl)oxy-4-[4-(9-bromo-2,3-dimethyl-naphtho[2,3-b]thiophen-4-yl)-2,6-dimethyl-phenoxysulfonyl]-benzoic acid tert-butyl ester (0.391 g, 0.506 mmol). Purification by triturating with ether gave 0.215 g (48%) of the title compound as a yellow solid, mp 235–238°C.; $^1$H NMR (DMSO-d6)δ 1.55 (s, 3 H), 2.16 (s, 6 H), 2.35 (s, 3 H), 7.19 (s, 2 H), 7.45–7.47 (m, 2 H), 7.61–7.68 (m, 2 H), 8.11 (m, 3 H), 8.30 (d, 1 H), 8.45 (ddd, 1 H), 8.91 (dd, 1 H), 9.24 (d, 1 H), 13.9 (br s, 1 H). mass spectrum (+APCI) m/z 714 (M+H). Anal. Calcd. for $C_{35}H_{26}BrNO_7S_2$: C, 58.66; H, 3.66; N, 1.95. Found: C, 58.50; H, 3.80; N, 1.77.

EXAMPLE 27

4-[4-(9-Bromo-2,3-dimethyl-naphtho[2,3-b]thiophen-4-yl)-2, 6-dimethyl-phenoxysulfonyl]-2-phenylacetoxy-benzoic acid Step 1

4-[4-(9-Bromo-2,3-dimethyl-naphtho[2,3-b]thiophen-4-yl)-2, 6-dimethyl-phenoxysulfonyl]-2-phenylacetoxy-benzoic acid tert butyl ester The title compound was prepared according to the procedure in Example 17, step 1, using 4-[4-(9-bromo-2,3-dimethyl-naphtho[2,3-b]thiophen-4-yl)-2, 6-dimethyl-phenoxysulfonyl]-2-hydroxy-benzoic acid tert-butyl ester (0.500 g, 0.691 mmol), pyridine (0.335 mL, 4.15 mmol) and phenylacetylchloride (0.183 mL, 1.38 mmol). Purification on Biotage KP-Sil eluting with 3% EtOAc/pet. ether gave 0.272 g (51%) of the title compound. $^1$H NMR (DMSO-d6) δ 1.51 (s, 9 H), 1.56 (s, 3 H), 2.14 (s, 6 H), 2.43 (s, 3 H), 4.04 (s, 2 H), 7.18 (s, 2H), 7.27–7.37 (m, 5 H), 7.46–7.49 (m, 2 H), 7.66 (ddd, 1 H), 8.01–8.07 (m, 2 H), 8.13–8.21 (m, 2 H).

Step 2

4-[4-(9-Bromo-2,3-dimethyl-naphtho[2,3-b]thiophen-4-yl)-2, 6-dimethyl-phenoxysulfonyll-2-phenylacetoxy-benzoic acid The title compound was prepared according to the procedure in Example 17, step 2, using 4-[4-(9-bromo-2,3-dimethyl-naphtho[2,3-b]thiophen-4-yl)-2, 6-dimethyl-phenoxysulfonyl]-phenoxysulfonyl]-2-phenylacetoxy-benzoic acid tert butyl ester (0.272 g, 0.352 mmol). Purification on 2% $H_3PO_4$/MeOH treated silica gel eluting with 20% acetone/hexane gave 0.207 g (81%) of the title compound as a yellow solid, mp 35–238° C. $^1$H NMR (DMSO-d6) δ 1.56 (s, 3 H), 2.13 (s, 6 H), 2.43 (s, 3 H), 4.00 (s, 2 H), 7.17 (s, 2 H), 7.25–7.34 (m, 5 H), 7.44–7.51 (m, 2 H), 7.65 (ddd, 1 H), 7.96 (d, 1 H), 8.04 (dd, 1 H), 8.19 (d, 1 H), 8.23 (d, 1 H), 13.8–14.1 (br s, 1 H). mass spectrum (–ESI) m/z 727 (M–H). Anal. Calcd. for $C_{37}H_{29}BrNO_7S_2$: C, 60.91; H, 4.01; N, 0.00. Found: C, 60.61; H, 4.19; N, –0.36.

EXAMPLE 28

2-(4-Cyano-benzoyloxy-4-[4-(9-bromo-2,3-dimethyl-naphthod2,3-b]thiophen-4-yl)-2,6-dimethyl-phenoxysulfonyl]-benzoic acid Step 1

2-(4-Cyano-benzoyloxy-4-1 4-(9-bromo-2,3-dimethyl-naphtho[2,3-b]thiophen-4-2,6-dimethyl-phenoxysulfonyl]-benzoic acid tert-butyl ester The title compound was prepared according to the procedure in Example 17, step 1, using 4-[4-(9-bromo-2,3-dimethyl-naphtho[2,3-b]thiophen-4-yl)-2,6-dimethyl-phenoxysulfonyl]-2-hydroxy-benzoic acid tert-butyl ester (0.400 g, 0.599 mmol), pyridine (0.291 mL, 3.59 mmol) and 4-cyanobenzoyl chloride (0.199 g, 1.20 mmol). Purification on Biotage KP-Sil eluting with a 7 & 15% EtOAc/pet. ether step gradient gave 0.324 g (68%) of the title compound as a yellow solid. $^1$H NMR (DMSO-d6) δ 1.34 (s, 9 H), 1.54 (s, 3 H), 2.16 (s, 6 H), 2.36 (s, 3 H), 7.19 (s, 2 H), 7.45–7.46 (m, 2 H), 7.62–7.66 (m, 1 H), 8.11–8.25 (m, 6 H), 8.30 (d, 2 H).

Step 2

2-(4-Cyano-benzoyl)oxy-4-[4-(9-bromo-2,3-dimethyl-naphtho[2,3-b]thiophen-4-yl)-2,6-dimethyl-phenoxysulfonyl]-benzoic acid The title compound was prepared according to the procedure in Example 17, step 2, using 2-(4-cyano-benzoyl)oxy-4-[4-(9-bromo-2,3-dimethyl-naphtho[2,3-b]thiophen-4-yl)-2,6-dimethyl-phenoxysulfonyl]-benzoic acid tert-butyl ester (0.440 g, 0.551 mmol). Purification on 2% $H_3PO_4$/MeOH treated silica gel eluting with 25% EtOAc/hexane gave 0.188 g (46%) of the title compound as a yellow solid. $^1$H NMR (DMSO-d6)δ 1.54 (s, 3 H), 2.16 (s, 6 H), 2.36 (s, 3 H), 7.19 (s, 2 H), 7.45–7.46 (m, 2 H), 7.62–7.66 (m, 1 H), 8.08–8.14 (m, 3 H), 8.17–8.20 (m, 2 H), 8.25–8.31 (m, 3 H), 13.7–14.0 (br s, 1 H). mass spectrum (–APCI) m/z 738 (M–H). Anal. Calcd. for $C_{37}H_{26}BrNO_7S_2$: C, 60.00; H, 3.54; N, 1.89. Found: C, 60.16; H, 3.58; N, 1.83.

EXAMPLE 29

2-(3-Methoxy-benzoyl)oxy-4-[4-(9-bromo-2,3-dimethyl-naphtho[2,3-b]thiophen-4-yl)-2,6-dimethyl-phenoxysulfonyl]-benzoic acid Step 1

2-(4-Methoxy-benzoyl)oxy-4-[4-(9-bromo-2,3-dimethyl-naphtho[2,3-b]thiophen-4-yl)-2,6-dimethyl-phenoxysulfonyl]-benzoic acid tert-butyl ester The title compound was prepared according to the procedure in Example 17, step 1, using 4-[4-(9-bromo-2,3-dimethyl-naphtho[2,3-b]thiophen-4-yl)-2,6-dimethyl-phenoxysulfonyl]-2-hydroxy-benzoic acid tert-butyl ester (0.500 g, 0.691 mnol), pyridine (0.335 mL, 4.15 mmol) and m-anisoyl chloride (0.194 mL, 1.38 mmol). Purification on Biotage KP-Sil eluting with a 5 & 7% EtOAc/pet. ether step gradient gave 0.504 g (68%) of the title compound as a white solid. $^1$H NMR (DMSO-d6) δ 1.33 (s, 9 H), 1.53 (s, 3 H), 2.15 (s, 6 H), 2.33 (s, 3 H), 3.82 (s, 3 H), 7.19 (s, 2 H), 7.36 (dd, 1 H), 7.45–7.46 (m, 2 H), 7.55 (t, 1 H), 7.61–7.65 (m, 2 H), 7.75 (d, 1 H), 8.08 (d, 1 H), 8.13 (dd, 1 H), 8.18–8.22 (m, 2 H). mass spectrum (+APCI) m/z 818 (M+H).

Step 2

2-(3-Methoxy-benzoyl)oxy-4-[4-(9-bromo-2,3-dimethl-naphtho[2,3-b]thiophen-4-yl)-2,6-dimethyl-phenoxysulfonyl]-benzoic acid The title compound was prepared according to the procedure in Example 17, step 2, using 2-(4-methoxy-benzoyl)

oxy-4-[4-(9-bromo-2,3-dimethyl-naphtho[2,3-b]thiophen-4-yl)-2,6-dimethyl-phenoxysulfonyl]-benzoic acid tert-butyl ester (0.470 g, 0.595 mmol). Purification on 2% $H_3PO_4$/MeOH treated silica gel eluting with 20% acetone/hexane gave 0.443 g (98%) of the title compound as a yellow solid, mp 126–150° C. $^1$H NMR (DMSO-d6) δ 1.53 (s, 3 H), 2.14 (s, 6 H), 2.32 (s, 3 H), 3.81 (s, 3 H), 7.18 (s, 2 H), 7.34 (dd, 1 H), 7.44–7.46 (m, 2 H), 7.52 (m, 1 H), 7.57–7.58 (m, 1 H), 7.61–7.66 (m, 1 H), 7.70 (d, 1 H), 8.03 (d, 1 H), 8.11 (dd, 1 H), 8.18 (d, 1 H), 8.28 (d, 1 H), 13.7–13.9 (br s, 1 H). mass spectrum (–APCI) m/z 743 (M–H).

Anal. Calcd. for $C_{37}H_{29}BrNO_8S_2$: C, 59.60; H, 3.92; N, 0.00. Found: C, 59.42; H, 3.97; N, –0.02.

EXAMPLE 30

Isonicotinic acid 5-[4-(9-bromo-2,3-dimethyl-naphtho[2,3-b]thiophen-4-yl)-2,6-dimethyl-phenoxysulfonyl]-2-carboxy-phenyl ester Step 1

2-(Pyrid-4-ylcarbonyl)oxy-4-[4-(9-bromo-2,3-dimethyl-naphtho[2, 3-b]thiophen-4-yl)-2,6-dimethyl-phenoxysulfonyl]-benzoic acid tert-butyl ester The title compound was prepared according to the procedure in Example 25, step 1, using 4-[4-(9-bromo-2,3-dimethyl-naphtho[2,3-b]thiophen-4-yl)-2, 6-dimethyl-phenoxysulfonyl]-2-hydroxy-benzoic acid tert-butyl ester (0.500 g, 0.691 mmol), isonicotinic acid (0.0851 g, 0.691 mmol), 2-chloro-1-methylpyridinium iodide (0.212g, 0.829 mmol) and triethylamine (0.327 mL, 2.35 mmol). Purification on Biotage KP-Sil eluting with 25% EtOAc/hexane gave 0.461 g (86%) of the title compound. $^1$H NMR (DMSO-d6) δ 1.35 (s, 9 H), 1.54 (s, 3 H), 2.17 (s, 6 H), 2.36 (s, 3 H), 7.19 (s, 2 H0, 7.45–7.47 (m, 2 H), 7.61–7.66 (m, 1 H), 8.04 (dd, 2 H), 8.13–8.25 (m, 4 H), 8.92 (dd, 2 H). mass spectrum (+ESI) m/z 772/774 (M+H).

Step 2

Isonicotinic acid 5-[4-(9-bromo-2,3-dimethyl-naphtho[2,3-b]thiophen-4-yl)-2, 6-dimethyl-phenoxysulfonyl]-2-carboxy-phenyl ester The title compound was prepared according to the procedure in Example 17, step 2, using 2-(pyrid-4-ylcarbonyl) oxy-4-[4-(9-bromo-2,3-dimethyl-naphtho[2, 3-b]thiophen-4-yl)-2,6-dimethyl-phenoxysulfonyl]-benzoic acid tert-butyl ester (0.445 g, 0.576 mmol). Purification by crystallization from acetone gave 0.365 g (88%) of the title compound as a white solid, mp 231–240° C. $^1$H NMR (DMSO-d6) δ 1.54 (s, 3 H), 2.16 (s, 6 H), 2.35 (s, 3 H), 7.19 (s, 2 H), 7.44–7.47 (m, 2 H), 7.61–7.65 (m, 1 H), 7.99 (dd, 2 H), 8.13 (dd, 1 H), 8.18–8.20 (m, 2 H), 8.30 (d, 1 H), 8.89 (dd, 2 H), 13.8–14.1 (br s, 1 H). mass spectrum (–APCI) m/z 714/716 (M–H). Anal. Calcd. for $C_{35}H_{26}NBrO_7S_2 \cdot 0.4H_2O$: C, 58.08; H, 3.73; N, 1.94. Found: C, 58.15; H, 3.98; N, 1.85.

What is claimed is:

1. A compound of formula I having the structure

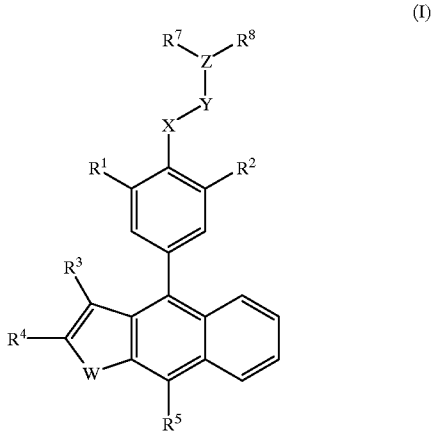

(I)

wherein $R^1$ and $R^2$ are each, independently, hydrogen, nitrile, nitro, amino, alkylamino of 1–6 carbon atoms, dialkyl amino of 1–6 carbon atoms per alkyl group, cycloalkylamino of 3–8 carbon atoms, alkyl of 1–6 carbon atoms, perfluoroalkyl of 1–6 carbon atoms, halogen, cycloalkyl of 3–8 carbon atoms, thienyl, furyl, phenyl or phenyl mono-, di-, or tri- substituted with halogen, hydroxy, alkyl of 1–6 carbon atoms, perfluoroalkyl of 1–6 carbon atoms, alkoxy of 1–6 carbon atoms, or perfluoroalkoxy of 1–6 carbon atoms;

$R^3$ and $R^4$ are each, independently, hydrogen, alkyl of 1–6 carbon atoms, perfluoroalkyl of 1–6 carbon atoms, hydroxyalkyl of 1–6 carbon atoms, aminoalkyl of 1–6 carbon atoms, acyl of 2–7 carbon atoms;

$R^5$ is hydrogen, halogen, alkyl of 1–6 carbon atoms, perfluoroalkyl of 1–6 carbon atoms, nitrile, alkoxy of 1–6 carbon atoms, aryloxy, arylalkoxy of 6–12 carbon atoms, arylsulfanyl;

W is S, O, or $NR^9$;

$R^9$ is hydrogen or alkyl of 1–6 carbon atoms,

X is O, —$NR^6$—, or —$(CH_2)_pNR^6$—;

$R^6$ is hydrogen, or alkyl of 1–6 carbon atoms;

p is 1 to 4;

Y is methylene, carbonyl, —$SO_2$—, or —SO—;

Z is phenyl, heteroaryl, or naphthyl;

$R^7$ and $R^8$ are each, independently, hydrogen, carboxyl, acyl of 2–7 carbon atoms, hydroxyl, hydroxyalkyl of 1–6 carbon atoms, hydroxyalkanoyl of 1–6 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aryl of 6–12 carbon atoms, aryloxycarbonyl of 7–13 carbon atoms, heteroaryloxycarbonyl, heteroaryl, tetrazolyl, mercapto, alkylsulfanyl of 1–6 carbon atoms, nitrile, amino, carbamoyl, aminoalkyl of 1–6 carbon atoms, alkylamino of 1–6 carbon atoms, dialkylamino of 1–6 carbon atoms per alkyl group, —$NHSO_2CF_3$, carboxyaldehyde, halogen, nitro, acylamino of 1–6 carbon atoms, 3-hydroxy-cyclobut-3-ene-4-yl-1,2-dione, or tetronic acid, —$OCOR^{10}$, —$OR^{10}$ R¹⁰ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

or a pharmaceutically acceptable salt thereof.

2. The compound according to claim 1, wherein $R^1$ and $R^2$ are each, independently, hydrogen, alkyl of 1–6 carbon atoms, perfluoroalkyl of 1–6 carbon atoms, bromo, iodo, cycloalkyl of 3–8 carbon atoms, phenyl or phenyl substituted with trifluoromethyl, chloro, methoxy, —$OCF_3$, thienyl, or furyl;

$R^3$ and $R^4$ are each, independently, alkyl of 1–6 carbon atoms, or perfluoroalkyl of 1–6 carbon atoms;

$R^5$ is hydrogen, halogen, alkyl of 1–6 carbon atoms, perfluoroalkyl of 1–6 carbon atoms, nitrile, alkoxy of 1–6 carbon atoms, aryloxy, arylalkoxy, or arylsulfanyl;

W is S, or O;

X is O, —$NR^6$—, or —$(CH_2)_p NR^6$—;

$R^6$ is hydrogen or, alkyl of 1–6 carbon atoms;

p is 1 to4;

Y is methylene, carbonyl, —$SO_2$ —, or —SO—;

Z is phenyl, pyridyl, naphthyl, thienyl, furyl, pyrrolyl, pyrazolyl, isoxazolyl, or isothiazolyl;

$R^7$ and $R^8$ are, each independently, hydrogen, halogen, carboxyl, acyl of 1–6 carbon atoms, acylamino of 1–6 carbon atoms, hydroxyl, hydroxyalkyl of 1–6 carbon atoms, hydroxyalkanoyl of 1–6 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aryl of 6–12 carbon atoms, aryloxy of 7–13 carbon atoms, aryloxycarbonyl of 7–13 carbon atoms, heteroaryloxycarbonyl, pyridyl, tetrazolyl, pyrazolyl, oxazolyl, isoxazolyl, mercapto, alkylsulfanyl of 1–6 carbon atoms, nitrile, amino, —$NHSO_2CF_3$, carbamoyl, aminoalkyl of 1–6 carbon atoms, alkylamnino of 1–6 carbon atoms, dialkylamino in which each of the alkyl groups is of 1–6 carbon atoms, carboxyaldehyde, halogen, nitro, or pyrimidyl or pyrimidyl substituted with alkylsulfanyl of 1–6 carbon atoms, 3-hydroxy-cyclobut-3-ene-4-yl-1,2-dione, —$OR^{10}$,—$OCOR^{10}$ or a pharmaceutically acceptable salt thereof.

3. The compound according to claim 2, wherein $R^1$ and $R^2$ are, each independently, hydrogen, alkyl of 1–6 carbon atoms, bromo, or cyclopentyl;

$R^3$ and $R^4$ are alkyl of 1–6 carbon atoms;

$R^5$ is hydrogen or bromine;

W is S, or O;

X is O, —$NR^6$—, or —$CH_2 NR^6$—;

$R^6$ is hydrogen or alkyl of 1–6 carbon atoms;

Y is methylene, carbonyl, or —$SO_2$—;

Z is phenyl, thienyl, pyrazolyl, or thiazolyl;

$R^7$ and $R^8$ are each, independently, hydrogen, halogen, acyl of 1–6 carbon atoms, carboxyl, hydroxyl, alkoxycarbonyl of 2–7 carbon atoms, alkyl of 1–6 carbon atoms, pyridyl, isoxazolyl, nitrile, or pyrimidyl or pyrimidyl substituted with alkylsulfamyl of 1–6 carbon atoms, —$OCOR^{10}$, or $OR^{10}$;

$R^{10}$ is aryl of 6–12 carbon atoms, monocyclic heteroaryl, or alkyl of 1–6 carbon atoms; or a pharmaceutically acceptable salt thereof.

4. The compound according to claim 1, which is 4-[4-(9-bromo-2, 3-dimethyl-naphtho[2,3-b]thiophen-4-yl)-2-isopropyl-phenoxysulfonyl]-2-hydroxy-benzoic acid or a pharmaceutically acceptable salt thereof.

5. The compound according to claim 1, which is 4-[4-(9-bromo-2,3-dimethyl-naphtho[2,3-b]thiophen-4-yl)-2,6-dimethyl-phenoxysulfonyl]-2-hydroxy-benzoic acid or a pharmaceutically acceptable salt thereof.

6. The compound according to claim 1, which is 4-[4-(9-bromo-2,3-dimethyl-naphtho[2,3-b]thiophen-4-yl)-2-cyclopentyl-phenoxysulfonyl]-2-hydroxy-benzoic acid or a pharmaceutically acceptable salt thereof.

7. The compound according to claim 1, which is 4-[4-(9-bromo-2,3-dimethyl-naphtho[2,3-b]thiophen-4-yl)-2,6-diisopropyl-phenoxysulfonyl]-2-hydroxy-benzoic acid or a pharmaceutically acceptable salt thereof.

8. The compound according to claim 1, which is 2-acetoxy-4-[4-(9-bromo-2,3-dimethyl-naphtho[2,3-b]thiophen-4-yl)-2,6-dimethyl-phenoxysulfonyl]-benzoic acid or a pharmaceutically acceptable salt thereof.

9. The compound according to claim 1, which is 2-acetoxy-4-[4-(9-bromo-2,3-dimethyl-naphtho[2,3-b]thiophen-4-yl)-2-cyclopentyl-phenoxysulfonyl]-benzoic acid or a pharmaceutically acceptable salt thereof.

10. The compound according to claim 1, which is 2-butyryloxy-4-[4-(9-bromo-2,3-dimethyl-naphtho[2,3-b]thiophen-4-yl)-2,6-dimethyl-phenoxysulfonyl]-benzoic acid or a pharmaceutically acceptable salt thereof.

11. The compound according to claim 1, which is 2-benzoyloxy-4-[4-(9-bromo-2,3-dimethyl-naphtho[2,3-b]thiophen-4-yl)-2,6-dimethyl-phenoxysulfonyl]-benzoic acid or a pharmaceutically acceptable salt thereof.

12. The compound according to claim 1, which is 2-propionyloxy-4-[4-(9-bromo-2,3-dimethyl-naphtho[2,3-b]thiophen-4-yl)-2,6-dimethyl-phenoxysulfonyl]-benzoic acid or a pharmaceutically acceptable salt thereof.

13. The compound according to claim 1, which is 5-[4-(9-bromo-2,3-dimethyl-naphtho[2,3-b]thiophen-4-yl)-2-cyclopentyl-phenoxysulfonyl]-4-methoxy-thiophene-3-carboxylic acid or a pharmaceutically acceptable salt thereof.

14. The compound according to claim 1, which is 5-[4-(9-bromo-2,3-dimethyl-naphtho[2,3-b]thiophen-4-yl)-2-cyclopentyl-phenoxysulfonyl]-4-hydroxy-thiophene-3-carboxylic acid or a pharmaceutically acceptable salt thereof.

15. The compound according to claim 1, which is 4-[2-cyclopentyl-4-(2,3-dimethyl-naphtho[2,3-b]thiophen-4-yl)-phenoxysulfonyl]-2-hydroxy-benzoic acid or a pharmaceutically acceptable salt thereof.

16. The compound according to claim 1, which is 4-[2-cyclopentyl-4-(2,3-dimethyl-naphtho[2,3-b]furan-4-yl)-phenoxysulfonyl]-2-hydroxy-benzoic acid or a pharmaceutically acceptable salt thereof.

17. The compound according to claim 1, which is 4-[2-bromo-4-(2,3-dimethyl-naphtho[2,3-b]furan-4-yl)-6-ethyl-phenoxysulfonyl]-2-hydroxy-benzoic acid or a pharmaceutically acceptable salt thereof.

18. The compound according to claim 1, which is 4-[4-(2,3-dimethyl-naphtho[2,3-b]furan-4-yl)-2,6-diethyl-phenoxysulfonyl]-2-hydroxy-benzoic acid or a pharmaceutically acceptable salt thereof.

19. The compound according to claim 1, which is 4-[4-(9-bromo-2,3-dimethyl-naphtho[2,3-b]thiophen-4-yl)-2,6-dimethyl-phenoxysulfonyl]-2-hydroxy-benzoic acid tert-butyl ester or a pharmaceutically acceptable salt thereof.

20. The compound according to claim 1, which is 2-(4-methoxy-benzoyl)oxy-4-[4-(9-bromo-2,3-dimethyl-naphtho

[2,3-b]thiophen-4-yl)-2,6-dimethyl-phenoxysulfonyl]-benzoic acid or a pharmaceutically acceptable salt thereof.

21. The compound according to claim 1, which is 5-[4-(2,3-dimethyl-naphtho[2,3-b]thiophen-4-yl)-2,6-diethyl-phenoxysulfonyl]-4-methoxy-thiophene-3-carboxylic acid or a pharmaceutically acceptable salt thereof.

22. The compound according to claim 1, which is 5-pyridin-2-yl-thiophene-2-sulfonic acid 2-cyclopentyl-4-(2,3-dimethyl-naphtho[2,3-b]thiophen-4-yl)-phenyl ester or a pharmaceutically acceptable salt thereof.

23. The compound according to claim 1, which is 4-benzoyloxy-5-[4-(2,3-dimethyl-naphtho[2,3-b]thiophen-4-yl)-2,6-diethyl-phenoxysulfonyl]-thiophene-3-carboxylic acid or a pharmaceutically acceptable salt thereof.

24. The compound according to claim 1, which is 3-[2-cyclopentyl-4-(2,3-dimethyl-naphtho[2,3-b]thiophen-4-yl)-phenoxysulfonyl]-benzoic acid or a pharmaceutically acceptable salt thereof.

25. The compound according to claim 1, which is 5-(2-methylsulfanyl-pyrimidin-4-yl)-thiophene-2-sulfonic acid 2-cyclopentyl-4-(2,3-dimethyl-naphtho[2,3-b]thiophen-4-yl)-phenyl ester or a pharmaceutically acceptable salt thereof.

26. The compound according to claim 1, which is 2-benzoyloxy-4-[4-(2,3-dimethyl-naphtho[2,3-b]thiophen-4-yl)-2,6-dimethyl-phenoxysulfonyl]-benzoic acid or a pharmaceutically acceptable salt thereof.

27. The compound according to claim 1, which is 2-(4-chloro-benzoyl)oxy-4-[4-(2,3-dimethyl-naphtho[2,3-b]thiophen-4-yl)-2,6-dimethyl-phenoxysulfonyl]-benzoic acid or a pharmaceutically acceptable salt thereof.

28. The compound according to claim 1, which is nicotinic acid 2-carboxy-5-[4-(2,3-dimethyl-naphtho[2,3-b]thiophen-4-yl)-2,6-dimethyl-phenoxysulfonyl]2-phenyl ester or a pharmaceutically acceptable salt thereof.

29. The compound according to claim 1, which is nicotinic acid 2-carboxy-5-[4-(9-bromo-2,3-dimethyl-naphtho[2,3-b]thiophen-4-yl)-2,6-dimethyl-phenoxysulfonyl]-phenyl ester or a pharmaceutically acceptable salt thereof.

30. The compound according to claim 1, which is 4-[4-(9-bromo-2,3-dimethyl-naphtho[2,3-b]thiophen-4-yl)-2,6-dimethyl-phenoxysulfonyl]-2-phenylacetoxy-benzoic acid or a pharmaceutically acceptable salt thereof.

31. The compound according to claim 1, which is 2-(4-cyano-benzoyl)oxy-4-[4-(9-bromo-2,3-dimethyl-naphtho[2,3-b]thiophen-4-yl)-2,6-dimethyl-phenoxysulfonyl]-benzoic acid or a pharmaceutically acceptable salt thereof.

32. The compound according to claim 1, which is 2-(3-methoxy-benzoyl)oxy-4-[4-(9-bromo-2,3-dimethyl-naphtho[2,3-b]thiophen-4-yl)-2,6-dimethyl-phenoxysulfonyl]-benzoic acid or a pharmaceutically acceptable salt thereof.

33. The compound according to claim 1, which is isonicotinic acid 5-[4-(9-bromo-2,3 -dimethyl-naphtho[2,3-b]thiophen-4-yl)-2,6-dimethyl-phenoxysulfonyl]-2-carboxy-phenyl ester or a pharmaceutically acceptable salt thereof.

34. A method of treating metabolic disorders mediated by insulin resistance or hyperglycemia in a mammal in need thereof which comprises administering to said mammal, a compound of formula I having the structure

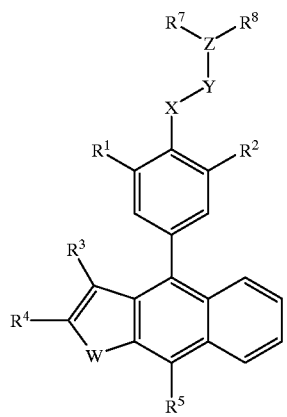

(I)

wherein
$R^1$ and $R^2$ are each, independently, hydrogen, nitrile, nitro, amino, alkylamino of 1–6 carbon atoms, dialkylamino of 1–6 carbon atoms per alkyl group, cycloalkylamino of 3–8 carbon atoms, alkyl of 1–6 carbon atoms, perfluoroalkyl of 1–6 carbon atoms, halogen, cycloalkyl of 3–8 carbon atoms, thienyl, furyl, phenyl or phenyl mono-, di-, or tri- substituted with halogen, hydroxy, alkyl of 1–6 carbon atoms, perfluoroalkyl of 1–6 carbon atoms, alkoxy of 1–6 carbon atoms, or perfluoroalkoxy of 1–6 carbon atoms;

$R^3$ and $R^4$ are each, independently, hydrogen, alkyl of 1–6 carbon atoms, perfluoroalkyl of 1–6 carbon atoms, hydroxyalkyl of 1–6 carbon atoms, aminoalkyl of 1–6 carbon atoms, acyl of 2–7 carbon atoms;

$R^5$ is hydrogen, halogen, alkyl of 1–6 carbon atoms, perfluoroalkyl of 1–6 carbon atoms, nitrile, alkoxy of 1–6 carbon atoms, aryloxy, arylalkoxy of 6–12 carbon atoms, arylsulfanyl;

W is S, O, or $NR^9$;

$R^9$ is hydrogen or alkyl of 1–6 carbon atoms,

X is O, —$NR^6$—, or —$(CH_2)_p NR^6$—;

$R^6$ is hydrogen, or alkyl of 1–6 carbon atoms;

p is 1 to 4;

Y is methylene, carbonyl, —$SO_2$—, or —SO—;

Z is phenyl, heteroaryl, or naphthyl;

$R^7$ and $R^8$ are each, independently, hydrogen, carboxyl, acyl of 2–7 carbon atoms, hydroxyl, hydroxyalkyl of 1–6 carbon atoms, hydroxyalkanoyl of 1–6 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aryl of 6–12 carbon atoms, aryloxycarbonyl of 7–13 carbon atoms, heteroaryloxycarbonyl, heteroaryl, tetrazolyl, mercapto, alkylsulfanyl of 1–6 carbon atoms, nitrile, amino, carbamoyl, aminoalkyl of 1–6 carbon atoms, alkylamino of 1–6 carbon atoms, dialkylamino of 1–6 carbon atoms per alkyl group, —$NHSO_2CF_3$, carboxyaldehyde, halogen, nitro, acylamino of 1–6 carbon atoms, 3-hydroxy-cyclobut-3-ene-4-yl-1,2-dione, or tetronic acid, —$OCOR^{10}$, —$OR^{10}$ $R^{10}$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

or a pharmaceutically acceptable salt thereof.

35. A method of treating or inhibiting type II diabetes in a mammal in need thereof which comprises administering to said mammal, a compound of formula I having the structure

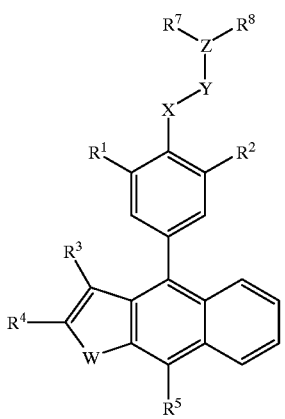

(I)

wherein
- $R^1$ and $R^2$ are each, independently, hydrogen, nitrile, nitro, amino, alkylamino of 1–6 carbon atoms, dialkylamino of 1–6 carbon atoms per alkyl group, cycloalkylamino of 3–8 carbon atoms, alkyl of 1–6 carbon atoms, perfluoroalkyl of 1–6 carbon atoms, halogen, cycloalkyl of 3–8 carbon atoms, thienyl, furyl, phenyl or phenyl mono-, di-, or tri- substituted with halogen, hydroxy, alkyl of 1–6 carbon atoms, perfluoroalkyl of 1–6 carbon atoms, alkoxy of 1–6 carbon atoms, or perfluoroalkoxy of 1–6 carbon atoms;
- $R^3$ and $R^4$ are each, independently, hydrogen, alkyl of 1–6 carbon atoms, perfluoroalkyl of 1–6 carbon atoms, hydroxyalkyl of 1–6 carbon atoms, aminoalkyl of 1–6 carbon atoms, acyl of 2–7 carbon atoms;
- $R^5$ is hydrogen, halogen, alkyl of 1–6 carbon atoms, perfluoroalkyl of 1–6 carbon atoms, nitrile, alkoxy of 1–6 carbon atoms, aryloxy, arylalkoxy of 6–12 carbon atoms, arylsulfanyl;
- W is S, O, or $NR^9$;
- $R^9$ is hydrogen or alkyl of 1–6 carbon atoms,
- X is O, —$NR^6$—, or —$(CH_2)_pNR^6$—;
- $R^6$ is hydrogen, or alkyl of 1–6 carbon atoms;
- p is 1 to 4;
- Y is methylene, carbonyl, —$SO_2$—, or —SO—;
- Z is phenyl, heteroaryl, or naphthyl;
- $R^7$ and $R^8$ are each, independently, hydrogen, carboxyl, acyl of 2–7 carbon atoms, hydroxyl, hydroxyalkyl of 1–6 carbon atoms, hydroxyalkanoyl of 1–6 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aryl of 6–12 carbon atoms, aryloxycarbonyl of 7–13 carbon atoms, heteroaryloxycarbonyl, heteroaryl, tetrazolyl, mercapto, alkylsulfanyl of 1–6 carbon atoms, nitrile, amino, carbamoyl, aminoalkyl of 1–6 carbon atoms, alkylamino of 1–6 carbon atoms, dialkylamino of 1–6 carbon atoms per alkyl group, —$NHSO_2CF_3$, carboxyaldehyde, halogen, nitro, acylamino of 1–6 carbon atoms, 3-hydroxy-cyclobut-3-ene-4-yl-1,2-dione, or tetronic acid, —$OCOR^{10}$, —$OR^{10}$
- $R^{10}$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

or a pharmaceutically acceptable salt thereof.

36. A method of modulating glucose levels in a mammal in need thereof which comprises administering to said mammal, a compound of formula I having the structure

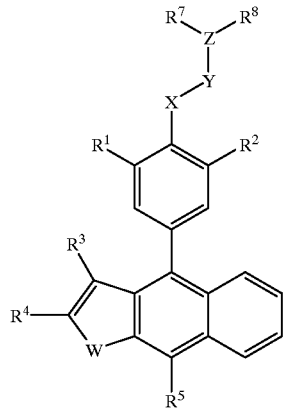

(I)

wherein
- $R^1$ and $R^2$ are each, independently, hydrogen, nitrile, nitro, amino, alkylamiino of 1–6 carbon atoms, dialkylarnino of 1–6 carbon atoms per alkyl group, cycloalkylamino of 3–8 carbon atoms, alkyl of 1–6 carbon atoms, perfluoroalkyl of 1–6 carbon atoms, halogen, cycloalkyl of 3–8 carbon atoms, thienyl, furyl, phenyl or phenyl mono-, di-, or tri- substituted with halogen, hydroxy, alkyl of 1–6 carbon atoms, perfluoroalkyl of 1–6 carbon atoms, alkoxy of 1–6 carbon atoms, or perfluoroalkoxy of 1–6 carbon atoms;
- $R^3$ and $R^4$ are each, independently, hydrogen, alkyl of 1–6 carbon atoms, perfluoroalkyl of 1–6 carbon atoms, hydroxyalkyl of 1–6 carbon atoms, aminoalkyl of 1–6 carbon atoms, acyl of 2–7 carbon atoms;
- $R^5$ is hydrogen, halogen, alkyl of 1–6 carbon atoms, perfluoroalkyl of 1–6 carbon atoms, nitrile, alkoxy of 1–6 carbon atoms, aryloxy, arylalkoxy of 6–12 carbon atoms, arylsulfanyl;
- W is S, O, or $NR^9$;
- $R^9$ is hydrogen or alkyl of 1–6 carbon atoms,
- X is O, —$NR^6$—, or —$(CH_2)_pNR^6$—;
- $R^6$ is hydrogen, or alkyl of 1–6 carbon atoms;
- p is 1 to 4;
- Y is methylene, carbonyl, —$SO_2$—, or —SO—;
- Z is phenyl, heteroaryl, or naphthyl;
- $R^7$ and $R^8$ are each, independently, hydrogen, carboxyl, acyl of 2–7 carbon atoms, hydroxyl, hydroxyalkyl of 1–6 carbon atoms, hydroxyalkanoyl of 1–6 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aryl of 6–12 carbon atoms, aryloxycarbonyl of 7–13 carbon atoms, heteroaryloxycarbonyl, heteroaryl, tetrazolyl, mercapto, alkylsulfanyl of 1–6 carbon atoms, nitrile, amino, carbamoyl, aminoalkyl of 1–6 carbon atoms, alkylamino of 1–6 carbon atoms, dialkylamino of 1–6 carbon atoms per alkyl group, —$NHSO_2CF_3$, carboxyaldehyde, halogen, nitro, acylamino of 1–6 carbon atoms, 3-hydroxy-cyclobut-3-ene-4-yl-1,2-dione, or tetronic acid, —$OCOR^{10}$, —$OR^{10}$ $R^{10}$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

or a pharmaceutically acceptable salt thereof.

37. A pharmaceutical composition which comprises a compound of formula I having the structure

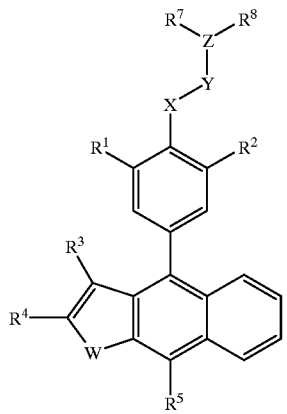

(I)

wherein $R^1$ and $R^2$ are each, independently, hydrogen, nitrile, nitro, amino, alkylamino of 1–6 carbon atoms, dialkylamino of 1–6 carbon atoms per alkyl group, cycloalkylamino of 3–8 carbon atoms, alkyl of 1–6 carbon atoms, perfluoroalkyl of 1–6 carbon atoms, halogen, cycloalkyl of 3–8 carbon atoms, thienyl, furyl, phenyl or phenyl mono-, di-, or tri- substituted with halogen, hydroxy, alkyl of 1–6 carbon atoms, perfluoroalkyl of 1–6 carbon atoms, alkoxy of 1–6 carbon atoms, or perfluoroalkoxy of 1–6 carbon atoms;

$R^3$ and $R^4$ are each, independently, hydrogen, alkyl of 1–6 carbon atoms, perfluoroalkyl of 1–6 carbon atoms, hydroxyalkyl of 1–6 carbon atoms, aminoalkyl of 1–6 carbon atoms, acyl of 2–7 carbon atoms;

$R^5$ is hydrogen, halogen, alkyl of 1–6 carbon atoms, perfluoroalkyl of 1–6 carbon atoms, nitrile, alkoxy of 1–6 carbon atoms, aryloxy, arylalkoxy of 6–12 carbon atoms, arylsulfanyl;

W is S, O, or $NR^9$;

$R^9$ is hydrogen or alkyl of 1–6 carbon atoms,

X is O, —$NR^6$—, or —$(CH_2)_pNR^6$—;

$R^6$ is hydrogen, or alkyl of 1–6 carbon atoms;

p is 1 to 4;

Y is methylene, carbonyl, —$SO_2$—, or —SO—;

Z is phenyl, heteroaryl, or naphthyl;

$R^7$ and $R^8$ are each, independently, hydrogen, carboxyl, acyl of 2–7 carbon atoms, hydroxyl, hydroxyalkyl of 1–6 carbon atoms, hydroxyalkanoyl of 1–6 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aryl of 6–12 carbon atoms, aryloxycarbonyl of 7–13 carbon atoms, heteroaryloxycarbonyl, heteroaryl, tetrazolyl, mercapto, alkylsulfanyl of 1–6 carbon atoms, nitrile, amino, carbamoyl, aminoalkyl of 1–6 carbon atoms, alkylamino of 1–6 carbon atoms, dialkylamino of 1–6 carbon atoms per alkyl group, —$NHSO_2CF_3$, carboxyaldehyde, halogen, nitro, acylamino of 1–6 carbon atoms, 3-hydroxy-cyclobut-3-ene-4-yl-1,2-dione, or tetronic acid, —$OCOR^{10}$, —$OR^{10}$ $R^{10}$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

or a pharmaceutically acceptable salt thereof, and a pharmaceutical carrier.

* * * * *